(12) United States Patent
Sloat et al.

(10) Patent No.: US 11,260,033 B2
(45) Date of Patent: *Mar. 1, 2022

(54) COMPOSITIONS FOR THE DELIVERY OF THERAPEUTIC AGENTS AND METHODS OF USE AND MAKING THEREOF

(71) Applicant: DISRUPTION LABS INC., Wilmington, DE (US)

(72) Inventors: Brian R. Sloat, Austin, TX (US); Michael A. Sandoval, Austin, TX (US); Tyler B. West, Austin, TX (US)

(73) Assignee: DISRUPTION LABS INC., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/211,616

(22) Filed: Mar. 24, 2021

(65) Prior Publication Data
US 2021/0251917 A1    Aug. 19, 2021

Related U.S. Application Data

(63) Continuation of application No. PCT/US2019/065288, filed on Dec. 9, 2019.
(Continued)

(51) Int. Cl.
*A61K 31/05* (2006.01)
*A61K 9/00* (2006.01)
(Continued)

(52) U.S. Cl.
CPC .......... *A61K 31/05* (2013.01); *A61K 9/0095* (2013.01); *A61K 9/10* (2013.01); *A61K 9/1075* (2013.01); *A61K 9/127* (2013.01); *A61K 9/1277* (2013.01); *A61K 47/14* (2013.01); *A61K 47/24* (2013.01); *A61K 47/28* (2013.01); *Y10S 977/773* (2013.01)

(58) Field of Classification Search
None
See application file for complete search history.

(56) References Cited

U.S. PATENT DOCUMENTS

| | | | |
|---|---|---|---|
| 5,180,713 | A | 1/1993 | Abra et al. |
| 5,496,811 | A | 3/1996 | Aviv et al. |

(Continued)

FOREIGN PATENT DOCUMENTS

| | | |
|---|---|---|
| CA | 2970917 | 6/2016 |
| EP | 3417846 A1 | 12/2018 |

(Continued)

OTHER PUBLICATIONS

Sabina King. "Liposomal vs Nano-Emulsified CBD: What is the Best CBD Delivery Method." https://www.hempurecbd.com/liposomal-vs-nanoemulsified-cbd/ accessed Jun. 3, 2021, 9 printed pages. (Year: 2021).*

(Continued)

*Primary Examiner* — Isaac Shomer
(74) *Attorney, Agent, or Firm* — Norton Rose Fulbright US LLP

(57) ABSTRACT

Some embodiments pertain to nanoparticle-based compositions and their use in methods for the delivery of CBD to subjects. In some embodiments, the compositions are stable for prolonged periods of time and provide enhanced bioavailability.

15 Claims, 14 Drawing Sheets

Related U.S. Application Data

(60) Provisional application No. 62/916,754, filed on Oct. 17, 2019, provisional application No. 62/889,824, filed on Aug. 21, 2019, provisional application No. 62/857,567, filed on Jun. 5, 2019, provisional application No. 62/846,474, filed on May 10, 2019, provisional application No. 62/778,132, filed on Dec. 11, 2018.

(51) Int. Cl.
*A61K 9/10* (2006.01)
*A61K 47/14* (2017.01)
*A61K 47/24* (2006.01)
*A61K 9/107* (2006.01)
*A61K 47/28* (2006.01)
*A61K 9/127* (2006.01)

(56) References Cited

U.S. PATENT DOCUMENTS

| | | | |
|---|---|---|---|
| 5,576,016 A * | 11/1996 | Amselem | A61K 9/5123 424/450 |
| 5,662,932 A | 9/1997 | Amselem et al. | |
| 5,716,637 A | 2/1998 | Amselem et al. | |
| 5,989,583 A | 11/1999 | Amselem | |
| 8,119,967 B2 | 2/2012 | O | |
| 8,758,826 B2 | 6/2014 | Bevier | |
| 8,808,734 B2 | 8/2014 | Winnicki | |
| 8,898,734 B2 | 11/2014 | Singh et al. | |
| 8,911,751 B2 | 12/2014 | Touitou et al. | |
| 9,095,555 B2 | 8/2015 | Winnicki | |
| 9,326,967 B2 | 5/2016 | Perry | |
| 9,549,906 B2 | 1/2017 | Lynch et al. | |
| 9,622,971 B2 | 4/2017 | Farber | |
| 9,675,656 B2 | 6/2017 | Crowley | |
| 9,849,108 B2 | 12/2017 | Perry | |
| 9,861,611 B2 | 1/2018 | Bromley | |
| 10,016,363 B2 | 7/2018 | Bromley | |
| 10,028,919 B2 | 7/2018 | Kaufman | |
| 10,052,303 B2 | 8/2018 | Winnicki | |
| 10,071,053 B2 | 9/2018 | Victor et al. | |
| 10,195,149 B2 | 2/2019 | Farber | |
| 10,265,362 B2 | 4/2019 | Schaneville | |
| 2001/0016196 A1 | 8/2001 | Benz et al. | |
| 2003/0096000 A1 | 5/2003 | Solis et al. | |
| 2003/0225156 A1 | 12/2003 | Mechoulam et al. | |
| 2005/0266067 A1 | 12/2005 | Sengupta et al. | |
| 2006/0100288 A1 | 5/2006 | Bague | |
| 2007/0049645 A1 | 3/2007 | Mechoulam et al. | |
| 2007/0072939 A1 | 3/2007 | Kupper | |
| 2007/0116829 A1 | 5/2007 | Prakash et al. | |
| 2007/0207173 A1 | 9/2007 | Chen | |
| 2008/0078317 A1 | 4/2008 | Furuya et al. | |
| 2008/0113031 A1 | 5/2008 | Moodley | |
| 2008/0253960 A1 | 10/2008 | Zheng et al. | |
| 2008/0262079 A1 | 10/2008 | Mach et al. | |
| 2008/0279927 A1 | 11/2008 | Daftary et al. | |
| 2009/0010976 A1 | 1/2009 | Lintner | |
| 2009/0028931 A1 | 1/2009 | Wasan et al. | |
| 2009/0047234 A1 | 2/2009 | Touitou et al. | |
| 2009/0074824 A1 | 3/2009 | Vila Pena et al. | |
| 2010/0266675 A1 | 10/2010 | Gerwick et al. | |
| 2011/0002982 A1 | 1/2011 | Tardi et al. | |
| 2011/0071118 A1 | 3/2011 | Lichtengerber | |
| 2012/0093931 A9 | 4/2012 | McGinnis et al. | |
| 2012/0321670 A1 | 12/2012 | Doshi et al. | |
| 2013/0011484 A1 | 1/2013 | Bevier | |
| 2013/0052259 A1 | 2/2013 | Barenholz et al. | |
| 2013/0089600 A1 * | 4/2013 | Winnicki | A61K 9/107 424/450 |
| 2013/0095032 A1 | 4/2013 | Margalit et al. | |
| 2014/0033023 A1 | 1/2014 | Yang et al. | |
| 2014/0302121 A1 | 10/2014 | Bevier | |
| 2014/0302148 A1 | 10/2014 | Winnicki | |
| 2014/0311146 A1 | 10/2014 | Fayemi et al. | |
| 2014/0312570 A1 | 10/2014 | Foster | |
| 2014/0348926 A1 | 11/2014 | Hoffman et al. | |
| 2015/0057341 A1 | 2/2015 | Perry | |
| 2015/0103850 A1 | 4/2015 | Wang et al. | |
| 2015/0216799 A1 | 8/2015 | Farber | |
| 2015/0258040 A1 | 9/2015 | Lynch et al. | |
| 2015/0258114 A1 | 9/2015 | Friedhoff | |
| 2015/0313868 A1 | 11/2015 | Morgan | |
| 2015/0342902 A1 | 12/2015 | Vangara et al. | |
| 2015/0343071 A1 | 12/2015 | Vangara et al. | |
| 2015/0374770 A1 | 12/2015 | Crowley | |
| 2016/0022711 A1 | 1/2016 | Choung et al. | |
| 2016/0030387 A1 | 2/2016 | Winnicki | |
| 2016/0051510 A1 | 2/2016 | Allen et al. | |
| 2016/0081927 A1 | 3/2016 | Bromley | |
| 2016/0081975 A1 | 3/2016 | Bromley | |
| 2016/0081976 A1 | 3/2016 | Bromley | |
| 2016/0103850 A1 | 4/2016 | Gupta et al. | |
| 2016/0144039 A1 | 5/2016 | Shah et al. | |
| 2016/0256435 A1 | 9/2016 | Perry | |
| 2016/0263047 A1 | 9/2016 | Kaufman | |
| 2016/0271252 A1 | 9/2016 | Vangara et al. | |
| 2016/0279073 A1 | 9/2016 | Donsky et al. | |
| 2016/0287152 A1 | 10/2016 | Schwartz et al. | |
| 2016/0324777 A1 | 11/2016 | Victor et al. | |
| 2016/0349245 A1 | 12/2016 | Zhang et al. | |
| 2016/0367480 A1 | 12/2016 | Jeung | |
| 2016/0367496 A1 | 12/2016 | Kumar et al. | |
| 2017/0000744 A1 * | 1/2017 | Kaufman | A61K 47/36 |
| 2017/0224634 A1 | 8/2017 | Vangara et al. | |
| 2017/0274030 A1 | 9/2017 | Crowley | |
| 2017/0368020 A1 | 12/2017 | Estey et al. | |
| 2018/0000727 A1 | 1/2018 | Willinsky | |
| 2018/0004004 A1 | 1/2018 | Tamasanis et al. | |
| 2018/0015179 A1 | 1/2018 | Polakis et al. | |
| 2018/0028489 A1 | 2/2018 | Vangara et al. | |
| 2018/0042845 A1 | 2/2018 | Sinai et al. | |
| 2018/0042890 A1 | 2/2018 | Sinai et al. | |
| 2018/0098962 A1 | 4/2018 | Bromley | |
| 2018/0116998 A1 | 5/2018 | Sinai et al. | |
| 2018/0185324 A1 | 7/2018 | Sinai et al. | |
| 2018/0221306 A1 | 8/2018 | Borgstrom | |
| 2018/0228731 A1 | 8/2018 | Singh | |
| 2018/0255801 A1 | 9/2018 | Victor | |
| 2018/0289665 A1 | 10/2018 | Turner et al. | |
| 2018/0296493 A1 | 10/2018 | Kaufman | |
| 2018/0303791 A1 | 10/2018 | Sinai et al. | |
| 2018/0311205 A1 | 11/2018 | Morgan | |
| 2018/0325861 A1 | 11/2018 | Domb et al. | |
| 2018/0333355 A1 | 11/2018 | Victor et al. | |
| 2018/0353463 A1 | 12/2018 | Winnicki | |
| 2018/0360757 A1 * | 12/2018 | Doroudian | A61K 31/485 |
| 2019/0078086 A1 | 3/2019 | Rincon et al. | |
| 2020/0037638 A1 | 2/2020 | Farad | |
| 2020/0121616 A1 * | 4/2020 | Gedo | A61K 9/0019 |
| 2021/0298340 A1 * | 9/2021 | Alsayar | A23L 2/52 |

FOREIGN PATENT DOCUMENTS

| | | |
|---|---|---|
| KR | 2019/0084035 A | 7/2019 |
| WO | WO 94/05298 | 3/1994 |
| WO | WO 94/26252 | 11/1994 |
| WO | WO 94/26255 | 11/1994 |
| WO | WO 97/36577 | 10/1997 |
| WO | WO 2000/027359 A1 | 5/2000 |
| WO | WO 2001/003668 A1 | 1/2001 |
| WO | WO 2001/049268 | 7/2001 |
| WO | WO 2003/070232 A1 | 8/2003 |
| WO | WO 2006/024958 A2 | 3/2006 |
| WO | WO 2006/073419 A2 | 7/2006 |
| WO | WO 07/061796 | 5/2007 |
| WO | WO 2007/043057 A3 | 11/2007 |
| WO | WO 2008/010788 | 1/2008 |
| WO | WO 2008/120207 A3 | 1/2009 |
| WO | WO 2010/008762 | 1/2010 |
| WO | WO 2012/066334 | 5/2012 |
| WO | WO 2012/104655 A3 | 8/2012 |
| WO | WO 2012/003003 A2 | 10/2012 |

(56) References Cited

FOREIGN PATENT DOCUMENTS

| | | |
|---|---|---|
| WO | WO 2013/009928 A1 | 1/2013 |
| WO | WO 2013/105101 A1 | 7/2013 |
| WO | WO 2013/108254 A1 | 7/2013 |
| WO | WO 14/028796 | 2/2014 |
| WO | WO 2013/006729 A3 | 5/2014 |
| WO | WO 2014/100231 A1 | 6/2014 |
| WO | WO 2015/057751 A1 | 4/2015 |
| WO | WO 15/068052 | 5/2015 |
| WO | WO 2015/068052 A3 | 5/2015 |
| WO | WO 15/117011 | 8/2015 |
| WO | WO 15/184127 | 12/2015 |
| WO | WO 16/044805 | 3/2016 |
| WO | WO 16/044813 | 3/2016 |
| WO | WO 2016/084075 A1 | 6/2016 |
| WO | WO 2016/092539 A1 | 6/2016 |
| WO | WO 2016/100228 A3 | 6/2016 |
| WO | WO 2016/103254 A1 | 6/2016 |
| WO | WO 2016/144376 A1 | 9/2016 |
| WO | WO 2016/147186 A1 | 9/2016 |
| WO | WO 2016/181394 A1 | 11/2016 |
| WO | WO 16/191651 | 12/2016 |
| WO | WO 2016/199148 A1 | 12/2016 |
| WO | WO 2017/054071 A1 | 4/2017 |
| WO | WO 2017/072762 A1 | 5/2017 |
| WO | WO-2017072762 A1 * 5/2017 ............ A61K 31/05 |  |
| WO | WO 2017/177261 A1 | 10/2017 |
| WO | WO 17/204986 | 11/2017 |
| WO | WO 2017/203529 A1 | 11/2017 |
| WO | WO 17/223309 | 12/2017 |
| WO | WO 2018/061007 | 4/2018 |
| WO | WO 2018/112479 A1 | 6/2018 |
| WO | WO 18/200024 | 11/2018 |
| WO | WO 2018/204326 A1 | 11/2018 |
| WO | WO 2018/205038 A1 | 11/2018 |
| WO | WO 2018/213932 A1 | 11/2018 |
| WO | WO 2018/237109 | 12/2018 |
| WO | WO 2019/005830 A1 | 1/2019 |
| WO | WO 2019/135224 A1 | 7/2019 |
| WO | WO 2019/135225 A1 | 7/2019 |
| WO | WO 2020/123407 A1 | 6/2020 |

OTHER PUBLICATIONS

Exelead. "Liposomes and Lipid Nanoparticles as Delivery Vehicles for Personalized Medicine." https://www.exeleadbiopharma.com/news/liposomes-and-lipid-nanoparticles-as-delivery-vehicles-for-personalized-medicine originally published Nov. 16, 2018, downloaded Jun. 3, 2021, 18 pages. (Year: 2018).*

Ida's Soap Box. "How Does Soap Work?" https://www.chagrinvalleysoapandsalve.com/blog/posts/how-does-soap-work/ accessed Nov. 15, 2021, originally published Apr. 18, 2015, pp. 1-8. (Year: 2015).*

Susanna Lauren. "Evaluation of Emulsion Stability by Interfacial Rheology Measurements." https://www.biolinscientific.com/blog/evaluation-of-emulsion-stability-by-interfacial-rheology-measurements accessed Nov. 16, 2021, originally published Nov. 10, 2020, pp. 1-10. (Year: 2020).*

Microfluidics. Accessed at https://analytik.co.uk/wp-content/uploads/2017/03/application-note-use-of-microfluidizer-technology-for-cannabis-products.pdf on Dec. 2, 2021, 2 printed pages. (Year: 2021).*

"CBD Tincture with BioPrime™ Nanoparticle CBD." Vitality Health CBD, vitalityhealthcbd.com/cbd-tincture/. Nov. 8, 2019.

Atsmon, Jacob et al., "PTL401, a New Formulation Based on Pro-Nano Dispersion Technology, Improves Oral Cannabinoids Bioavailability in Healthy Volunteers." Journal of Pharmaceutical Sciences, (May 2018) vol. 107, No. 5, pp. 1423-1429. ).

Bruni, N.; Della Pepa, C.; Oliaro-Bosso, S.; Pessione, E.; Gastaldi, D.; Dosio, F. Cannabinoid Delivery Systems for Pain and Inflammation Treatment. Molecules 2018, 23, 2478.

Cannabis Global, Inc. "MCTC—Achieves Sub-Micron Polymeric Particles of Cannabidiol (CBD) and TPGS—Files Cannabinoid Nanoparticle Patent." GlobeNewswire News Room, "GlobeNewswire", Sep. 25, 2019, www.globenewswire.com/news-release/2019/09/25/1920579/0/en/MCTC-Achieves-Sub-Micron-Polymeric-Particles-of-Cannabidiol-CBD-and-TPGS-Files-Cannabinoid-Nanoparticle-Patent.html.

Cosco, D et al., "Colloidal carriers for the enhanced delivery through the skin." expert Opinion on Drug Delivery, (Jul. 2008) vol. 5, No. 7, pp. 737-755.

International Search Report and Written Opinion, dated Feb. 13, 2020 in PCT/US19/65288.

Kaufman, "Nanosphere Delivery Systems, Methods for Overcoming Bioavailability Limitations." Aug. 2013, Life Enhancement Magazine, 7 pages. [old.life-enhancement.com/magazine/article/2910-nanosphere-delivery-systems].

Kulkarni, Sunisha, Dr. et al., "Ethosomes—A promising way for transdermal drug delivery." International Journal of Pharmaceutical Sciences and Research, (2015) vol. 6, No. 9, pp. 3663-3670.

Lawrence, D.K. et al., "The effects of 1 tetrahydrocannabinol and other cannabinoids on spin labeled liposomes and their relationship to mechanisms of general anesthesia." Molecular Pharmacology, (1975) vol. 11, No. 5, pp. 595-602.

Santos, Pauline S. et al., "-caryophyllene Delivery Systems: Enhancing the Oral Pharmacokinetic and Stability." Current pharmaceutical design, (Dec. 8, 2018) vol. 24, No. 29, pp. 3440-3453.

Verma et al., "Therapeutic and cosmeceutical potential of ethosomes: An overview." Journal of Advanced Pharmaceutical Technology and Research, (Jul.-Sep. 2010) vol. 1, No. 3, pp. 274-282.

Wahid, Ambekar Abdul et al., "Ethosomes: A tool for transdermal drug delivery." Current Trends in Biotechnology and Pharmacy, (2011) vol. 5, No. 1, pp. 972-981.

Astruc-Diaz, Jul. 9, 2012, Cannabinoids delivery systems based on supramolecular inclusion complexes and polymeric nanocapsules for treatment of neuropathic pain, Diplome de Doctoral, Universite de Lyon, https://tel.archives-ouvertes.fr/tel-00935 5 8 8, 277 pp.

International Search Report & Opinion, dated Sep. 15, 2021, issued in related application No. PCT/US2021/036393.

International Search Report and Written Opinion issued in Corresponding PCT application No. PCT/US2021/37461, dated Nov. 3, 2021.

Aparicio-Blanco et al., "Lipid nanocapsules decorated and loaded with cannabidiol as targeted prolonged release carriers for glioma therapy: In vitroscreening of critical parameters" *European Journal of Pharmaceutics and Biopharmaceutics* 2019, 134, 126-137.

Extended European Search Report issued in Corresponding European Application No. 19897051.9, dated Nov. 19, 2021.

* cited by examiner

FIG. 5A-E

COMPOSITIONS FOR THE DELIVERY OF THERAPEUTIC AGENTS AND METHODS OF USE AND MAKING THEREOF

CROSS REFERENCE TO RELATED APPLICATIONS

This application is a continuation of PCT/US2019/065288, filed Dec. 9, 2019, which claims the benefit of priority to U.S. Provisional Application No. 62/916,754, filed Oct. 17, 2019, U.S. Provisional Application No. 62/889,824, filed Aug. 21, 2019, U.S. Provisional Application No. 62/857,567, filed Jun. 5, 2019, U.S. Provisional Application No. 62/846,474, filed May 10, 2019, and U.S. Provisional Application No. 62/778,132, filed Dec. 11, 2018, the disclosures of each of which are hereby incorporated by reference in their entireties. Any and all applications for which a priority claim is identified in the Application Data Sheet as filed with the present application are also hereby incorporated by reference in their entireties under 37 CFR 1.57.

FIELD

This disclosure relates generally to lipid, nanoparticle-based compositions (e.g., liposomal, solid lipid particles, oil-in-water emulsions, etc.) and their use in methods for the delivery of hydrophobic therapeutic agents (e.g., vitamins, nutrients, plant extracts, nutraceuticals, pharmaceuticals, or other beneficial agents for delivery) to subjects. In some embodiments, the lipid compositions comprise cannabidiol ("CBD") as a therapeutic agent. In some embodiments, the compositions are stable (e.g., at room temperature) for prolonged periods of time.

BACKGROUND

Description of the Related Art

CBD is a phytocannabinoid used in the treatment of a variety of ailments. For example, CBD can be used for alleviating pain (e.g., from multiple sclerosis), treating epilepsy, and the treatment of certain neurological disorders. CBD can be taken into the body in multiple different ways, including by inhalation of cannabis smoke or vapor, as an aerosol spray into the cheek, and by mouth. CBD may be supplied as an oil (e.g., CBD-dominant hemp extract oil), capsules, dried cannabis, or as a prescription liquid solution.

SUMMARY

Some embodiments disclosed herein pertain to a particle composition and/or a lipid-based particle composition for the delivery of an active agent. In some embodiments, the particle is a lipid particle. In some embodiments, the particle is a nanoscale particle. In some embodiments, the particle is a microscale particle. In some embodiments, the particle is liposomal (e.g., is a liposome). In some embodiments, the particle comprises one or more of a phospholipid component, a non-phospholipid lipid component (e.g., a medium and/or long chain triglyceride component), a sterol component, and/or water. In some embodiments, the particle further comprises the active ingredient (e.g., a therapeutic agent). In some embodiments, the active ingredient is a phytocannabinoid. In some embodiments, the phytocannabinoid is CBD. In some embodiments, the lipid constituents of the particle allow it to solubilize CBD of high purity. In some embodiments, the CBD in the particle is of sufficient purity to provide a crystalline and/or solid (e.g., an amorphous or crystalline powder). In some embodiments, the CBD not an oil.

In some embodiments, the phytocannabinoid of a lipid-based particle composition as disclosed herein is a single phytocannabinoid (e.g., CBD). In some embodiments, the phytocannabinoid (e.g., CBD) has a purity by weight % of equal to or greater than about: 95%, 97%, 98%, 99%, 100%, or ranges including and/or spanning the aforementioned values. In some embodiments, the phytocannabinoid (e.g., CBD) is present in the lipid-based particle composition at dry weight % of equal to or greater than about: 5%, 8%, 10%, 15%, 20%, or ranges including and/or spanning the aforementioned values. In some embodiments, the phytocannabinoid is free of or essentially free of THC. In some embodiments, the phytocannabinoid (e.g., CBD) has a THC content by weight % of equal to or less than about: 1%, 0.5%, 0.25%, 0.1%, 0%, or ranges including and/or spanning the aforementioned values. In some embodiments, where present, THC is present below the limit of quantitation (LOQ) (e.g., when analyzed by high pressure liquid chromatography (HPLC) with standard detectors, such as UV/Vis, photodiode array, refractive index, fluorescence, light scattering, conductivity, and the like).

In some embodiments, the phospholipid component comprises one or more of phosphatidic acid, phosphatidylethanolamine, phosphatidylcholine, phosphatidylserine, phosphatidylinositol, phosphatidylinositol phosphate, phosphatidylinositol bisphosphate, and phosphatidylinositol trisphosphate. In some embodiments, the phospholipid component comprises phosphatidylcholine. In some embodiments, the phospholipid component is a single phospholipid. In some embodiments, the phospholipid component is phosphatidylcholine. In some embodiments, the phosphatidylcholine is highly pure. In some embodiments, the phosphatidylcholine has a purity by weight % of equal to or greater than about: 97%, 98%, 99%, 100%, or ranges including and/or spanning the aforementioned values. In some embodiments, the phosphatidylcholine is present in the lipid-based particle composition at dry weight % of equal to or greater than about: 10%, 20%, 30,%, 35%, 40%, 45%, 50%, or ranges including and/or spanning the aforementioned values.

In some embodiments, the lipid component comprises a triglyceride. In some embodiments, the lipid component comprises a medium chain triglyceride (MCT). In some embodiments, the medium chain triglyceride comprises a fatty acid selected from one or more of caprioc acid, octanoic acid, capric acid, caprylic acid, and/or lauric acid (e.g., is formed from). In some embodiments, the medium chain triglyceride comprises a fatty acid 6-12 carbons in length (e.g., 6, 7, 8, 9, 10, 11, or 12). In some embodiments, the lipid component comprises a long chain triglyceride. In some embodiments, the long chain triglyceride comprises a fatty acid greater than 12 carbons in length (e.g., greater than or equal to 13, 14, 15, 16, 17, 18, 19, or 20 carbons in length, or ranges including and/or spanning the aforementioned values). In some embodiments, the lipid component is a single lipid. In some embodiments, the lipid component is MCT. In some embodiments, the MCT is highly pure. In some embodiments, the MCT has a purity by weight % of equal to or greater than about: 90%, 95%, 97%, 98%, 99%, 100%, or ranges including and/or spanning the aforementioned values. In some embodiments, the MCT (or LCT) is present in the lipid-based particle composition at dry weight % of equal to or greater than about: 10%, 20%, 30%, 35%, 40%, 45%, 50%, or ranges including and/or spanning the aforementioned values.

In some embodiments, the sterol component comprises cholesterol. In some embodiments, the sterol component is a single sterol. In some embodiments, the sterol component is cholesterol. In some embodiments, the cholesterol (or other sterol) is highly pure. In some embodiments, the cholesterol (or other sterol) has a purity by weight % of equal to or greater than about: 97%, 98%, 99%, 100%, or ranges including and/or spanning the aforementioned values. In some embodiments, the cholesterol (or other sterol) is present in the lipid-based particle composition at dry weight % of equal to or greater than about: 1%, 2%, 4%, 5%, 8%, or ranges including and/or spanning the aforementioned values.

In some embodiments, the lipid-based particle composition is aqueous while in other embodiments the composition may be provided as a dry or substantially dry solid (e.g., having a water content in weight % of less than or equal to 20%, 15%, 10%, 5%, 2%, 1%, 0.5%, or ranges including and/or spanning the aforementioned values). In some embodiments, where the lipid-based particle composition is aqueous, water may be present at a wet weight percent of equal to or less than about: 70%, 75%, 77%, 80%, 85%, or ranges including and/or spanning the aforementioned values. In some embodiments of the aqueous composition, the phytocannabinoid (e.g., CBD) is present in the composition at wet weight % of equal to or greater than about: 1%, 2%, 5%, 8%, 10%, 15%, 20%, or ranges including and/or spanning the aforementioned values. In some embodiments, the phosphatidylcholine is present in the aqueous composition at wet weight % of equal to or greater than about: 5%, 10%, 15%, 20%, or ranges including and/or spanning the aforementioned values. In some embodiments, the MCT is present in the aqueous composition at wet weight % of equal to or greater than about: 5%, 10%, 15%, 20%, or ranges including and/or spanning the aforementioned values. In some embodiments, the cholesterol is present in the aqueous composition at wet weight % of equal to or greater than about: 0.5%, 1.0%, 2.0%, 3.0%, 5.0%, or ranges including and/or spanning the aforementioned values.

In some embodiments, as disclosed elsewhere herein, the particle comprises CBD, phosphatidylcholine, cholesterol, a lipid component other than a phospholipid (e.g., one or more of a medium chain triglyceride, a long chain triglyceride, and/or hemp oil), and/or water. In some embodiments, the CBD is present in an amount of less than or equal to about 25 mg/ml. In some embodiments, the phosphatidylcholine is present in an amount of less than or equal to about 100 mg/ml. In some embodiments, the cholesterol is present in an amount of less than or equal to about 25 mg/ml. In some embodiments, the medium chain triglyceride is present in an amount of less than or equal to about 100 mg/ml.

In some embodiments, the lipid-based particle composition further comprises a preservative. In some embodiments, the preservative comprises one or more of malic acid, citric acid, potassium sorbate, sodium benzoate, and Vitamin E. In some embodiments, malic acid is present in an amount of less than or equal to about 0.85 mg/ml. In some embodiments, citric acid is present in an amount of less than or equal to about 0.85 mg/ml. In some embodiments, potassium sorbate is present in an amount of less than or equal to about 1 mg/ml. In some embodiments, sodium benzoate is present in an amount of less than or equal to about 1 mg/ml. In some embodiments, the composition further comprises a flavoring agent.

Some embodiments pertain to a lipid-based particle composition, comprising: a nanoparticle comprising: cannabidiol (CBD) that is of sufficient purity that it exists in a solid and/or powdered state prior to formulation in the nanoparticle composition at a weight percent in the composition ranging from 1% to 10%; a phosphatidylcholine at a weight percent in the composition ranging from 2.5% to 15%; a sterol at a weight percent in the composition ranging from 0.5% to 5%; and a medium chain triglyceride at a weight percent in the composition ranging from 2.5% to 15%. In some embodiments, the composition comprises water at a weight percent in the composition ranging from 60% to about 80%. In some embodiments, the nanoparticles have an average size ranging from about 75 nm to about 175 nm. In some embodiments, upon storage for a period of one month, the average size of the nanoparticles changes by less than about 20%.

In some embodiments, the lipid-based particle composition is in the form of liposomes and/or an oil-in-water nano-emulsion. In some embodiments, an appreciable amount of the nanoparticle composition does not settle and/or separate from the water upon standing for a period of at least about 12 hours. In some embodiments, the composition is configured such that when concentrated to dryness to afford a powder formulation of nanoparticles, the nanoparticle powder can be reconstituted to provide the nanoparticle composition. In some embodiments, the composition has a Tmax for CBD of less than 4.5 hours. In some embodiments, upon storage for a period of one month, the average size of the nanoparticles changes by less than about 20%. In some embodiments, the polydispersity of the nanoparticles in the composition is less than or equal to 0.15. In some embodiments, upon 90 days of storage at 25° C. and 60% relative humidity, the polydispersity of the nanoparticles changes by less than or equal to 10%. In some embodiments, upon 90 days of storage at 25° C. and 60% relative humidity, the polydispersity of the nanoparticles changes by less than or equal to 0.1. In some embodiments, the composition has a shelf life of greater than 18 months at 25° C. and 60% relative humidity. In some embodiments, upon 90 days of storage at 25° C. and 60% relative humidity, the D90 of the nanoparticles changes less than or equal to 10%. In some embodiments, the composition has a concentration max (Cmax) of 80 ng/ml after an oral dose of 15 mg/kg.

Some embodiments, pertain to a lipid-based particle composition, comprising a particle comprising cannabidiol (CBD) that is of sufficient purity that it exists in a solid and/or powdered state prior to formulation in the nanoparticle composition at a weight percent in the composition ranging from 5% to 15%, a phosphatidylcholine at a weight percent in the composition ranging from 35% to 60%, a sterol at a weight percent in the composition ranging from 2.5% to 10%, and a medium chain triglyceride at a weight percent in the composition ranging from 35% to 50%. In some embodiments, the composition further comprising a preservative. In some embodiments, the preservative comprises one or more of malic acid, citric acid, potassium sorbate, sodium benzoate, and Vitamin E. In some embodiments, the sterol is cholesterol. In some embodiments, the composition further comprises a flavoring agent.

In some embodiments, the composition has a Cmax of 80 ng/ml after an oral dose of 15 mg/kg. In some embodiments, the lipid-based particle composition is provided as a dry powder. In some embodiments, the powder is configured to be reconstituted in water to provide an aqueous solution. In some embodiments, wherein, upon reconstitution, nanoparticles within the aqueous solution have an average size ranging from about 75 nm to about 175 nm.

In some embodiments, the composition further comprising a preservative. In some embodiments, the preservative comprises one or more of malic acid, citric acid, potassium sorbate, sodium benzoate, and Vitamin E. In some embodiments, the sterol is cholesterol. In some embodiments, the composition further comprises a flavoring agent.

In some embodiments, as disclosed elsewhere herein, the lipid-based particle composition is in the form and/or comprises one or more of liposomes, an oil-in-water nanoemulsion (and/or microparticle emulsion), and/or solid lipid particles. In some embodiments, when suspended in water, an appreciable amount of the particles in the composition do not settle and/or do not separate (e.g., upon visual inspection) from the water upon standing for a period of at least about 12 hours. In some embodiments, when suspended in water, the particles remain substantially homogenously distributed in the water upon standing for a period of at least about 12 hours. In some embodiments, the nanoparticles have an average size ranging from about 10 nm to about 500 nm. In some embodiments, the composition comprises nanoparticles having an average size of less than or equal to about: 10 nm, 50 nm, 100 nm, 250 nm, 500 nm, 1000 nm, or ranges including and/or spanning the aforementioned values. In some embodiments, the composition comprises microparticles having an average size of less than or equal to about: 1000 nm, 1.5 µm, 2 µm, 3 µm, 5 µm, 10 µm or ranges including and/or spanning the aforementioned values. In some embodiments, the dried powder composition comprises microparticles that form nanoparticles (as disclosed herein) when reconstituted. In some embodiments, these dried powder compositions comprise particles having an average size of less than or equal to about: 250 nm, 500 nm, 1000 nm, 1.5 µm, 2 µm, 3 µm, 5 µm, 10 µm, 50 µm, or ranges including and/or spanning the aforementioned values. In some embodiments, upon storage for a period of one month, the average size of the nanoparticles (or microparticles) increases by less than about 10%.

In some embodiments, the lipid-based particle composition is configured such that when concentrated to dryness to afford dry particles (e.g., from any one of the oil-in-water emulsion (e.g., a nanoemulsion or microemulsion), liposome solution, and/or solid lipid particle) as a powder, the dry nanoparticles can be reconstituted to provide a reconstituted particle based solution (e.g., the nanoparticle composition). In some embodiments, when reconstituted, the average size of the nanoparticles increases or decreases by less than about 15% and/or by less than about 100%. In some embodiments, to form powders, excipients (and/or additives as disclosed elsewhere herein) may be added to the liposomes, oil-in-water nano-emulsions (and/or microparticle emulsions), and/or a solid lipid particle. In some embodiments, the excipient comprises trehalose.

Some embodiments, as disclosed elsewhere herein, pertain to a method of manufacturing a lipid-based particle composition. In some embodiments, one or more phytocannabinoids (e.g., CBD) is mixed with one or more lipophilic components of the composition to provide a solution. In some embodiments, one or more lipid components (that are not phospholipids) are added. In some embodiments, one or more sterols are added. In some embodiments, one or more phospholipids are added. In some embodiments, one or more flavoring and/or preservatives are added. In some embodiments, water is added. In some embodiments, the lipophilic ingredients are combined and the hydrophilic ingredients are combined separately. In some embodiments the lipophilic ingredients are then added to the hydrophilic ingredients. In some embodiments, the solution is passed through a microfluidizer and/or a high sheer homogenizer. In some embodiments, the process affords a particle composition.

In some embodiments, a method of manufacturing the particle composition of a phytocannabinoid is disclosed. In some embodiments, the phytocannabinoid is added to solvent. In some embodiments, one or more phospholipids are added to the solvent. In some embodiments, one or more sterols are added to the solvent. In some embodiments, one or more lipids is added to the solvent. In some embodiments, the solvent is removed to provide a substantially solid product. In some embodiments, the product is mixed with water to provide an emulsion. In some embodiments, the emulsion is passed through a microfluidizer and/or a high sheer homogenizer. In some embodiments, the process affords a nanoparticle composition.

Some embodiments pertain to a method of treating a patient in need of treatment comprising administering an effective amount therapeutic agent provided as a lipid-based particle composition as disclosed herein to the patient. Some embodiments pertain to a method of treating a patient in need of treatment comprising administering an effective amount of the composition to the patient. In some embodiments, the patient in need of treatment is a patient suffering from one or more of pain, anxiety & stress, seizures, malaise, inflammation, mood disorders, and insomnia. In some embodiments, the condition is treated by administering an effective amount of a composition as disclosed herein to the patient.

In some embodiments, the Cmax is increased relative to CBD alone or comparator embodiments (e.g., CBD oil-based products) by equal to or at least about: 15%, 20%, 50%, 100%, 150%, 200%, or ranges including and/or spanning the aforementioned values. In some embodiments, the Cmax is increased (relative to an oil-based product) by equal to or at least about: 10 ng/mL, 20 ng/mL, 30 ng/mL, 40 ng/mL, 50 ng/mL, 60 ng/mL, 70 ng/mL, 80 ng/mL, 90 ng/mL, or ranges including and/or spanning the aforementioned values.

In some embodiments, the Tmax for CBD is decreased (relative to CBD alone or a CBD in oil mixture) by equal to or at least about: 15%, 20%, 50%, 100%, 150%, 200%, or ranges including and/or spanning the aforementioned values. In some embodiments, the Tmax for CBD in a disclosed embodiment is decreased (relative to CBD alone or a CBD in oil mixture) by equal to or at least about: 15 minutes, 30 minutes, 45 minutes, 1 hour, 2 hours, or ranges including and/or spanning the aforementioned values.

In some embodiments, the AUC for CBD using a disclosed embodiment is increased (relative to CBD alone or a CBD in oil mixture) by equal to or at least about: 100 ng/mL*hr, 200 ng/mL*hr, 300 ng/mL*hr, 400 ng/mL*hr, or ranges including and/or spanning the aforementioned values. In some embodiments, the AUC is improved (relative to CBD alone or a CBD in oil mixture) by equal to or at least about: 25%, 50%, 100%, 150%, 200%, or ranges including and/or spanning the aforementioned values.

BRIEF DESCRIPTION OF THE DRAWINGS

FIG. 9A shows CBD plasma concentration data for an embodiment as disclosed herein, including for a lipid nanoparticle solution and a lipid nanoparticle powder. FIG. 9B provides a comparison of the lipid nanoparticle powder of FIG. 9A compared to commercial comparators comprising CBD oil. FIG. 9C provides a comparison of the lipid nanoparticle solution of FIG. 9A compared to commercial comparators comprising CBD oil. FIG. 9D provides an expanded view of the data in FIG. 9C.

DETAILED DESCRIPTION

Figure 1:
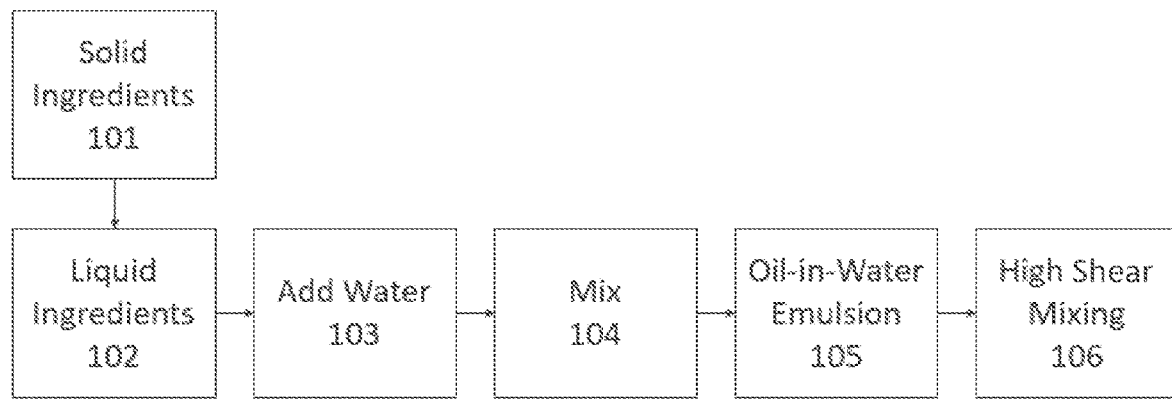
FIG. 1 is a flow chart showing an embodiment of a method of preparing a lipid-based particle composition as disclosed herein.

Some embodiments disclosed herein pertain to formulations and/or lipid-based particle compositions for the delivery of therapeutic agents to subjects. In some embodiments, the lipid-based particle compositions are nanoparticle compositions. In some embodiments, the nanoparticles comprise liposomes. Some embodiments pertain to methods of use and making the composition. In some embodiments, the therapeutic agent is a phytocannabinoid. In some embodiments, the phytocannabinoid is cannabidiol (CBD). In some embodiments, the composition is comprised of high grade ingredients (e.g., highly pure) that yield a well-characterized, reproducible delivery system. In some embodiments, the compositions as disclosed herein are stable for long periods of time. In some embodiments, the composition confers water solubility to hydrophobic therapeutic agents. In some embodiments, the composition imparts apparent solubility to a molecule that is otherwise considered practically insoluble in water (e.g., >10 liters of water needed to dissolve 1 gram of CBD) and/or practically water insoluble according to the biopharmaceutical classification system. In some embodiments, the composition comprises a liposomal and/or nano-emulsion composition of a CBD isolate. In some embodiments, the composition is configured for oral ingestion. In some embodiments, the CBD formulation is provided as a drinkable solution, such as a beverage, elixir, tonic, or the like. While some embodiments are disclosed herein in relation to CBD, it is to be understood that other hydrophobic therapeutic agents or nutrients can be employed using the delivery systems disclosed herein (e.g., fish oils, vitamin D and other lipid soluble vitamins). In some embodiments, hydrophilic therapeutic agents may also be used. Advantageously, the compositions disclosed herein may enhance the delivery of and/or slow or lessen the degradation of hydrophilic or hydrophobic therapeutic agents. Additionally, while some embodiments are disclosed in relation to nanoparticles, as disclosed elsewhere herein, microparticles are also envisioned.

Unless otherwise defined, all technical and scientific terms used herein have the same meaning as commonly understood by one of ordinary skill in the art to which this subject matter belongs. The terminology used in the description of the subject matter herein is for the purpose of describing particular embodiments only and is not intended to be limiting of the subject matter.

As used herein, "and/or" refers to and encompasses any and all possible combinations of one or more of the associated listed items, as well as the lack of combinations when interpreted in the alternative ("or").

The term "effective amount," as used herein, refers to that amount of a recited compound and/or composition that imparts a modulating effect, which, for example, can be a beneficial effect, to a subject afflicted with a disorder, disease or illness, including improvement in the condition of the subject (e.g., in one or more symptoms), delay or reduction in the progression of the condition, prevention or delay of the onset of the disorder, and/or change in clinical parameters, disease or illness, etc., as would be well known in the art. For example, an effective amount can refer to the amount of a composition, compound, or agent that improves a condition in a subject by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. In some embodiments, an improvement in a condition can be a reduction in disease symptoms or manifestations (e.g., pain, anxiety & stress, seizures, malaise, inflammation, mood disorders, insomnia, etc.). Actual dosage levels of active ingredients in an active composition of the presently disclosed subject matter can be varied so as to administer an amount of the active compound(s) that is effective to achieve the desired response for a particular subject and/or application. The selected dosage level will depend upon a variety of factors including, but not limited to, the activity of the composition, composition, route of administration, combination with other drugs or treatments, severity of the condition being treated, and the physical condition and prior medical history of the subject being treated. In some embodiments, a minimal dose is administered, and dose is escalated in the absence of dose-limiting toxicity to a minimally effective amount. Determination and adjustment of an effective dose, as well as evaluation of when and how to make such adjustments, are contemplated herein.

"Treat" or "treating" or "treatment" refers to any type of action that imparts a modulating effect, which, for example, can be a beneficial effect, to a subject afflicted with a disorder, disease or illness, including improvement in the condition of the subject (e.g., in one or more symptoms), delay or reduction in the progression of the condition, and/or change in clinical parameters, disease or illness, curing the illness, etc.

The "patient" or "subject" treated as disclosed herein is, in some embodiments, a human patient, although it is to be understood that the principles of the presently disclosed subject matter indicate that the presently disclosed subject matter is effective with respect to all vertebrate species, including mammals, which are intended to be included in the terms "subject" and "patient." Suitable subjects are generally mammalian subjects. The subject matter described herein finds use in research as well as veterinary and medical applications. The term "mammal" as used herein includes, but is not limited to, humans, non-human primates, cattle, sheep, goats, pigs, mini-pigs (a mini-pig is a small breed of swine weighing about 35 kg as an adult), horses, cats, dog, rabbits, rodents (e.g., rats or mice), monkeys, etc. Human subjects include neonates, infants, children, juveniles, adults and geriatric subjects. The subject can be a subject "in need of" the methods disclosed herein can be a subject that is experiencing a disease state and/or is anticipated to experience a disease state, and the methods and compositions of the invention are used for therapeutic and/or prophylactic treatment.

As used herein, the term "weight percent" (or wt %, weight %, percent by weight, etc.), when referring to a component, is the weight of the component divided by the weight of the composition that includes the component, multiplied by 100%. For example the weight percent of component A when 5 grams of component A is added to 95 grams of component B is 5% (e.g., 5 g A/(5 g A+95 g B)×100%). As used herein, the "dry weight %" (e.g., "dry wt %", "dry weight percent", etc.) of an ingredient is the weight percent of that ingredient in the composition where the weight of water has not been included in the calculation of the weight percent of that ingredient. A dry weight % can be calculated for a composition that does not include water or for a composition that includes water. As used herein, the "wet weight %" (e.g., "wet wt %", "wet weight percent", etc.) of an ingredient is the weight percent of that ingredient in a composition where the weight of water is included in the calculation of the weight percent of that ingredient. For example, the dry weight percent of component A when 5 grams of component A is added to 95 grams of component B and 100 grams of water is 5% (e.g., 5 g A/(5 g A+95 g B)×100%). Alternatively, the wet weight percent of component A when 5 grams of component A is added to 95 grams of component B and 100 grams of water is 2.5% (e.g., 5 g A/(5 g A+95 g B+100 g water)×100%).

As used herein, the term "phytocannabinoid" refers to a group of cannabinoids that occur naturally in the cannabis plant, including but not limited to, THC (tetrahydrocannabinol), THCA (tetrahydrocannabinolic acid), CBD (cannabidiol), CBDA (cannabidiolic acid), CBN (cannabinol), CBG (cannabigerol), CBC (cannabichromene), CBL (cannabicyclol), CBV (cannabivarin), THCV (tetrahydrocannabivarin), CBDV (cannabidivarin), CBCV (cannabichromevarin), CBGV (cannabigerovarin), CBGM (cannabigerol monomethyl ether), CBE (cannabielsoin), and CBT (cannabicitran).

As used herein, the term "phospholipid" refers to a lipid having two hydrophobic fatty acid tails and a hydrophilic head comprising of a phosphate group.

As used herein, the term "medium chain triglyceride" refers to tri-substituted triglycerides with fatty acids having aliphatic tails of 6 to 12 carbon atoms (6, 7, 8, 9, 10, 11, 12) and mixtures thereof.

As used herein, the term "long chain triglyceride" refers to tri-substituted triglycerides with fatty acids having an aliphatic tail of greater than 13 carbon atoms (13, 14, 15, 16, 17, 18, 19, 20, or more) and mixtures thereof.

As used herein, the term "sterol" refers to a subgroup of steroids with a hydroxyl group at the 3-position of the A-ring.

As used herein, the term "Cmax" is given its plain and ordinary meaning and refers to the maximum (or peak) plasma concentration of an agent after it is administered.

As used herein, the term "Tmax" is given its plain and ordinary meaning and refers to the length of time required for an agent to reach maximum plasma concentration after the agent is administered.

As used herein, the term "AUC" is given its plain and ordinary meaning and refers to the calculated area under the curve, referring to a plasma concentration-time curve (e.g., the definite integral in a plot of drug concentration in blood plasma vs. time.).

As used herein, "polydispersity" or "PDI" is used to describe the degree of non-uniformity of a size distribution of particles. Also known as the heterogeneity index, PDI is a number calculated from a two-parameter fit to the correlation data (the cumulants analysis). This index is dimensionless and scaled such that values smaller than 0.05 are mainly seen with highly monodisperse standards.

When referring to an amount present for one or more ingredients, the term "collectively or individually" (and variations thereof) means that the amount is intended to signify that the ingredients combined may be provided in the amount disclosed, or each individual ingredient may be provided in the amount disclosed. For example, if agents A and B are referred to as collectively or individually being present in a composition at a wt % of 5%, that means that A may be at 5 wt % in the composition, B may be at 5 wt % in the composition, or the combination of A and B may be present at a total of 5 wt % (A+B=5 wt %). Alternatively, where both A and B are present, A may be at 5 wt % and B may be at 5 wt %, totaling 10 wt %.

CBD is a prominent phytocannabinoid constituent of *Cannabis sativa* (Cannabis) that lacks the psychoactive effects of Δ9-tetrahydrocannabinol. CBD was first isolated from Cannabis in 1940 and structurally characterized in 1963. CBD may have broad therapeutic properties across a range of disorders including anxiety, depression, inflammation, pain, and seizure disorders either when administered alone or with THC. Evidence of CBD's therapeutic properties is largely limited to preclinical studies. However, in June 2018 the FDA granted approval of Epidiolex, a CBD isolated from marijuana for the treatment of pediatric seizure disorders, proving CBD's benefit in a controlled clinical trial setting.

With CBD's rise in popularity, consumers are exploring its purported benefits in high numbers. Retail sales of hemp-derived CBD products in the United States reached more than $350 million in 2018 and are expected to reach over $1.3 billion within the next 5 years. As the CBD market flourishes, many CBD manufacturers have come under government scrutiny for making unsubstantiated claims of its health benefits or reporting inaccurate lab test results. Being that CBD (or other phytocannabinoids) is currently available as an unregulated supplement, the quality and safety of consumer CBD products lacks sufficient characterization and laboratory testing. In 2017 survey, 69% of consumer CBD products (n=84) in the categories of oils, tinctures, and vaporizing liquids were found to be reported inaccurately (more than ±10% than label claim), underscoring the need of regulatory agencies to take steps to ensure CBD products are sufficiently characterized and tested. Additionally, the variations in purities of ingredients used to prepare these products make give them disperse efficacies and impurity profiles.

For instance, current available compositions for the delivery of CBD to a subject employ CBD as an oil extract. These CBD oils are disadvantageous for a variety of reasons. First, CBD oils exist in an oil state because they include impurities (e.g., agents that prevent the solidification of CBD). Second, those impurities vary from batch-to-batch, making the quality of CBD variable. Additionally, because CBD supplementation thus far has been largely unregulated, variations in CBD concentration and its impurity profile go largely unchecked. Some CBD oils may include THC or other agents. THC is the psychoactive agent in *Cannabis sativa*. It would be advantageous to use CBD that was highly pure to avoid such impurities (such as THC), because those impurities could result in patients avoiding CBD therapies altogether.

Exacerbating the issue, current CBD formulations use CBD oils to sufficiently disperse the compound and to form particles. Further compounding the issues with CBD impurities, the ingredients used to form lipophilic particles comprising CBD also have a wide variety of impurities and variations batch-to-batch. Moreover, the lipophilic compositions using CBD oil often rely, at least in part, on a distribution and/or variety of lipophilic impurities in each of the liposomal ingredients to aid in dispersing CBD. Because current delivery systems must use CBD oils and lipophilic ingredients with a distribution of compounds in order to sufficiently solubilize the compound and because CBD oils and the lipophilic ingredients used to solubilize them comprise impurities, delivery and stability of these mixtures is unpredictable. These impurities may also lead to side effects. Thus, new delivery systems that are able to utilize highly pure CBD forms and pure and/or uniform ingredients are needed.

Causing additional issues, CBD oils also have low bioavailability (due to poor absorption and due to their variable purity profile). Highly pure isolate forms of CBD perform even worse because they have poorer bioavailability. For instance, CBD isolate forms have low oral bioavailability due to low solubility in aqueous systems (e.g., and in the gut, etc.). Highly purified CBD exists as a solid isolate (e.g., a powder or crystalline form). These highly purified powders heretofore have not been formulated for oral delivery due to their prohibitively high aqueous insolubility (e.g., hydrophobicity). Indeed, to the knowledge of the inventors, prior to the lipid-based particle compositions and methods disclosed in the present disclosure, solid CBD isolate powder had not been provided in any delivery system to facilitate solubility and absorption. This is apparent from the impurity profile for commercial CBD products. As noted above, available CBD delivery systems make use of CBD oil. These systems have been shown to be ineffective for high purity CBD (such as a CBD crystalline composition or powder).

Some embodiments disclosed herein solve these or other problems by providing a lipid-based particle composition that can delivery highly pure CBD in a solubilizing particle delivery system (e.g., a liposomal system, oil-in-water emulsions, dry liposome particles, etc.). For example, in some embodiments, the disclosed lipid-based particle compositions achieve one or more of the following: they include less impurities, they have less variations batch-to-batch (e.g., stability, degradation profiles, efficacy), they have more delivery predictability, they less side effects when treating a patient, they have higher bioavailability, they have faster onset of activity, they have better efficacy, etc. Disclosed herein are CBD products prepared using the thoroughness and diligence of pharmaceutical drug development to consumer products. In some embodiments, a nano-lipid delivery system is utilized to impart apparent aqueous solubility and deliverability to an otherwise practically water insoluble molecule (e.g., CBD or other similar and/or hydrophobic phytocannabinoids and therapeutic molecules). In some embodiments, as disclosed herein, quality attributes of some embodiments disclosed herein have been determined to be high quality and reproducible. Such reproducibility and low variations may allow the products to generate a certificate of analysis for different batches. In some embodiments, the systems disclosed herein increase the bioavailability of CBD, decrease the time for absorption of CBD, increase the stability of CBD or the particles comprising the CBD, increase the consistency of delivery (e.g., by limiting batch-to-batch variation), and/or increase the efficacy of CBD (higher dosing and/or faster onset of activity). In some embodiments, the carriers disclosed herein are able to deliver CBD that has a purity of greater than or equal to about: 90%, 95%, 98%, 99%, 99.5%, 99.9%, 99.99%, or ranges including and/or spanning the aforementioned values. In some embodiments, the lipid-based particle compositions disclosed herein make use of CBD that is of sufficient purity that the CBD exists as a solid (e.g., a powder, a crystalline compound, etc.). In some embodiments, the solid CBD is solid due to its purity and lacks other agents that would cause it to solidify when impure. For example, in some embodiments, the CBD powder lacks maltodextrin or other additive agents that cause the solidification of CBD.

As disclosed elsewhere herein, some embodiments relate delivery systems that improve the absorption of the highly insoluble forms of CBD. In some embodiments, the CBD form used to prepare the lipid-based particle compositions disclosed herein (e.g., the CBD starting material) has an aqueous solubility of less than or equal to about: 0.05 mg/ml, 0.01 mg/ml, 0.012 mg/ml, 0.001 mg/ml, or ranges including and/or spanning the aforementioned values. In some embodiments, the aqueous solubility of the CBD starting material (and/or the amount of CBD that can be provided in an aqueous solution) can be improved to equal to or greater than about: 1 mg/ml, 5 mg/ml, 20 mg/ml, 30 mg/ml, 50 mg/ml, 100 mg/ml, or ranges including and/or spanning the aforementioned values.

In some embodiments, the hydrophobic therapeutic agent used to prepare the lipid-based particle compositions disclosed herein (e.g., a phytocannabinoid, vitamin, or other therapeutic agent, etc.) has an aqueous solubility of less than or equal to about: 0.05 mg/ml, 0.01 mg/ml, 0.012 mg/ml, 0.001 mg/ml, or ranges including and/or spanning the aforementioned values. In some embodiments, the solubility of the hydrophobic therapeutic agent (and/or the amount of the therapeutic that can be provided in an aqueous solution) used to prepare the compositions disclosed herein (e.g., a cannabinoid, etc.) can be improved to equal to or greater than about: 1 mg/ml, 5 mg/ml, 20 mg/ml, 30 mg/ml, 50 mg/ml, 100 mg/ml, or ranges including and/or spanning the aforementioned values. In some embodiments, the solubility of the hydrophobic therapeutic agent (including CBD) can be improved by at least about: 50%, 100%, 150%, 200%, 500%, 1000%, 10,000%, or ranges including and or spanning the aforementioned values.

In some embodiments, as disclosed elsewhere herein, a lipid, nanoparticle-based composition (e.g., a liposomal, solid lipid particles, oil-in-water emulsions, etc.) is provided to aid in the delivery of therapeutic agents. In some embodiments, when formulated, the dry weight % of CBD present in the compositions is equal to or at least about: 0.5%, 1%, 5%, 7.5%, 10%, 15%, 20%, 25%, 50%, or ranges including and/or spanning the aforementioned values. In some embodiments, the wet weight % of CBD present in the composition (with water included) is equal to or at least about: 0.5%, 1%, 2%, 3%, 4%, 5%, 7.5%, 10%, or ranges including and/or spanning the aforementioned values. In some embodiments, the CBD may be provided in the wet composition at a concentration of greater than or equal to about: 1 mg/ml, 5 mg/ml, 20 mg/ml, 30 mg/ml, 50 mg/ml, 100 mg/ml, or ranges including and/or spanning the aforementioned values.

In some embodiments, as disclosed elsewhere herein, the CBD used in the lipid-based particle compositions as disclosed herein has high purity as indicated by its existing in a solid form (e.g., powder) prior to processing (e.g., formulation into a composition as disclosed herein). In some embodiments, using the combinations disclosed herein, a composition comprising CBD in water is provided. In some embodiments, as disclosed elsewhere herein, the delivery system may be lipid-based and forms an oil-in-water emulsion (e.g., a nanoemulsion), a liposome, and/or solid lipid particle (e.g., nanoparticle). In some embodiments, the lipid-based delivery system provides particles in the nano-measurement range (as disclosed elsewhere herein). In some embodiments, a solid lipid nanoparticle is spherical or substantially spherical nanoparticle. In some embodiments, a solid lipid nanoparticle possesses a solid lipid core matrix that can solubilize lipophilic molecules. In some embodiments, the lipid core is stabilized by surfactants and/or emulsifiers as disclosed elsewhere herein, while in other embodiments, surfactants are absent. In some embodiments, the size of the particle is measured as a mean diameter. In some embodiments, the size of the particle is measured by dynamic light scattering. In some embodiments, the size of the particle is measured using a zeta-sizer. In some embodiments, the size of the particle can be measured using Scanning Electron Microscopy (SEM). In some embodiments, the size of the particle is measured using a cyrogenic SEM (cryo-SEM). Where the size of a nanoparticle is disclosed elsewhere herein, any one or more of these instruments or methods may be used to measure such sizes.

In some embodiments, as disclosed elsewhere herein, the lipid/nanoparticle-based composition (e.g., a liposomal composition as disclosed herein, a solid lipid particle composition as disclosed herein, an oil-in-water emulsion composition as disclosed herein, etc.), or simply the composition for brevity, comprises a phytocannabinoid and one or more of a phospholipid, a lipid other than a phospholipid (e.g., a lipid that is not a phospholipid), and a sterol. In some embodiments, as disclosed elsewhere herein, the composition comprises one or more of a phytocannabinoid, a phospholipid, a lipid other than a phospholipid (e.g., a lipid that is not a phospholipid), and a sterol. In some embodiments, the composition is aqueous (e.g., contains water) while in other embodiments, the composition is dry (lacks water or substantially lacks water). In some embodiments, the composition comprises nanoparticles in water (e.g., as a solution, suspension, or emulsion). In other embodiments, the composition is provided as a powder (e.g., that can be constituted or reconstituted in water). In some embodiments, as disclosed elsewhere herein, the water content (in wt %) of the composition is less than or equal to about: 10%, 5%, 2.5%, 1%, 0.5%, 0.1%, or ranges including and/or spanning the aforementioned values.

In some embodiments, as disclosed elsewhere herein, the one or more phytocannabinoid(s) is CBD. In other embodiments, the one or more phytocannabinoid(s) comprises one or more of CBD, THCa, 9-THC, 8-THC, CBDa, CBC, CBG, CBN, THCV, and/or CBGa. In some embodiments, the total potential THC does not to exceed 0.3 weight % of the phytocannabinoid, where the total potential THC is defined as THCa×0.877+9-THC+8-THC. In some embodiments, the only phytocannabinoid used as an ingredient and/or present is CBD. In some embodiments, the one or more phytocannabinoids (e.g., CBD), collectively or individually, are present in the aqueous lipid-based particle composition at a concentration of less than or equal to about: 100 mg/ml, 75 mg/ml, 50 mg/ml, 25 mg/ml, 20 mg/ml, 10 mg/ml, 5 mg/ml, 2.5 mg/ml or ranges including and/or spanning the aforementioned values. In some embodiments, the one or more phytocannabinoid(s) (e.g., CBD), collectively or individually, are present in the aqueous composition at a concentration of greater than or equal to about: 100 mg/ml, 75 mg/ml, 50 mg/ml, 25 mg/ml, 20 mg/ml, 10 mg/ml, 5 mg/ml, or ranges including and/or spanning the aforementioned values. In some embodiments, the one or more phytocannabinoid(s) (e.g., CBD), collectively or individually, are present in the composition at a dry wt % of equal to or at least about: 0.5%, 1%, 5%, 7.5%, 10%, 15%, 20%, 25%, or ranges including and/or spanning the aforementioned values. In some embodiments, the one or more phytocannabinoid(s) (e.g., CBD), collectively or individually, are present in the composition at a wet wt % of equal to or at least about: 0.1%, 0.25%, 0.5%, 1%, 2%, 3%, 4%, 5%, 7.5%, 10%, or ranges including and/or spanning the aforementioned values.

In some embodiments, instead of a phytocannabinoid(s) or in addition to phytocannabinoid(s), the lipid-based particle composition comprises a different therapeutic agent or active agents. In some embodiments, the therapeutic agent is one or more of a vitamin, a nutrient, a plant extract, a nutraceutical, a pharmaceutical, or another beneficial agent. In some embodiments, the therapeutic agent is hydrophilic. In some embodiments, the therapeutic agent is hydrophobic. In some embodiments, the therapeutic agent is amphiphilic. In some embodiments, the one or more therapeutic agent(s), collectively or individually, are present in the aqueous composition at a concentration of greater than or equal to about: 100 mg/ml, 75 mg/ml, 50 mg/ml, 25 mg/ml, 20 mg/ml, 10 mg/ml, 5 mg/ml, or ranges including and/or spanning the aforementioned values. In some embodiments, the one or more therapeutic agent(s) (collectively or individually) are present in the composition at a dry wt % of equal to or at least about: 0.5%, 1%, 5%, 7.5%, 10%, 15%, 20%, 25%, or ranges including and/or spanning the aforementioned values. In some embodiments, the one or more therapeutic agent(s) (collectively or individually) are present in the composition at a wet wt % of equal to or at least about: 0.1%, 0.25%, 0.5%, 1%, 2%, 3%, 4%, 5%, 7.5%, 10%, or ranges including and/or spanning the aforementioned values. In some embodiments, the therapeutic agent is selected from the group consisting of Noopept (N-phenylacetyl-L-prolyglygice ethyl ester), melatonin, gamma-aminobutyric acid (GABA), others, combinations thereof, or combinations with phytocannabinoids as disclosed herein. In some embodiments, when a hydrophilic composition is used, it is mixed with the aqueous soluble ingredients before mixing with the lipid ingredients.

In some embodiments, as disclosed elsewhere herein, the CBD is a purified form of CBD. As disclosed elsewhere herein, in some embodiments, the CBD used to prepare the lipid-based particle composition is a solid (e.g., is a CBD of sufficiently high purity that it exists as a solid). In some embodiments, the CBD (or other non-THC cannabinoid) is an isolate having a THC (including all THC isomers and stereoisomers) content (in weight %) of less than or equal to about: 0.01%, 0.1%, 0.3%, 0.5%, 1.0%, 3.0%, 4.0%, 5.0%, or ranges including and/or spanning the aforementioned values. In some embodiments, the CBD (or other non-THC cannabinoid) has a total potential THC content (in weight %) of less than or equal to about: 0.01%, 0.1%, 0.3%, 0.5%, 1.0%, 3.0%, 4.0%, 5.0%, or ranges including and/or spanning the aforementioned values. In some embodiments, the CBD (or other non-THC cannabinoid) is substantially THC free, lacks THC, or lacks a detectable amount of THC. In some embodiments, the CBD (or other non-THC cannabinoid) is isolated from hemp and/or marijuana. In some embodiments, the CBD (or other non-THC cannabinoid) is isolated from hemp and not marijuana. In some embodiments, the CBD (or other non-THC cannabinoid) is isolated from marijuana and not hemp. In some embodiments, the CBD (or other cannabinoid) has a terpene impurity content (in weight percent) of less than or equal to about: 0.01%, 0.1%, 0.3%, 0.5%, 1.0%, 2.0%, 5.0% or ranges including and/or spanning the aforementioned values.

As disclosed elsewhere herein, in some embodiments, the lipid-based particle composition comprises one or more phospholipids. In some embodiments, the one or more phospholipids comprises one or more of phosphatidic acid, phosphatidylethanolamine, phosphatidylcholine, phosphatidylserine, phosphatidylinositol, phosphatidylinositol phosphate, phosphatidylinositol bisphosphate, and phosphatidylinositol trisphosphate. In some embodiments, the phospholipid is phosphatidylcholine. In some embodiments, the only phospholipid present is phosphatidylcholine (e.g., the phospholipid lacks phospholipids other than phosphatidylcholine or is substantially free of other phospholipids). In some embodiments, the one or more phospholipid components (e.g., phosphatidylcholine, and/or others), collectively or individually, are present in the aqueous composition at a concentration of less than or equal to about: 400 mg/ml, 300 mg/ml, 200 mg/ml, 150 mg/ml, 100 mg/ml, 75 mg/ml, 50 mg/ml, 25 mg/ml, or ranges including and/or spanning the aforementioned values. For instance, as disclosed elsewhere herein, where two phospholipids are present (e.g., phosphatidylcholine and phosphatidylethanolamine), those phospholipids may be present collectively at a concentration of 50 mg/ml (e.g., 30 g/ml phosphatidylcholine and 20 g/ml phosphatidylethanolamine=50 mg/ml total) or individually at a concentration of 50 mg/ml (e.g., 50 g/ml phosphatidylcholine and 50 g/ml phosphatidylethanolamine). In some embodiments, the one or more phospholipid(s) (collectively or individually) are present in the composition at a dry wt % of equal to or less than about: 5%, 10%, 15%, 20%, 30%, 40%, 50%, 60%, or ranges including and/or spanning the aforementioned values. In some embodiments, the one or more phospholipid(s) (collectively or individually) are present in the composition at a wet wt % of equal to or less than about: 2.5%, 5%, 7.5%, 10%, 12.5%, 15%, 20%, 30%, 40%, or ranges including and/or spanning the aforementioned values. In some embodiments, the phosphatidylcholine is synthetic, derived from sunflower, soy, egg, or mixtures thereof. In some embodiments, the one or more phospholipids (and/or lipids) can be hydrogenated or non-hydrogenated.

In some embodiments, the phosphatidylcholine is high purity. For example, in some embodiments, the phosphatidylcholine is H100-3 grade (from Lipoid) and includes over 96.3% phosphatidylcholine (hydrogenated) or over 99% phosphatidylcholine (hydrogenated). In some embodiments, the phosphatidylcholine has a purity of greater than or equal to about: 92.5%, 95%, 96%, 96.3%, 98%, 99%, 100%, or ranges including and/or spanning the aforementioned values. In some embodiments, the phosphatidylcholine has a total % impurity content by weight of less than or equal to about: 8.5%, 5%, 4%, 3.7%, 2%, 1%, 0%, or ranges including and/or spanning the aforementioned values. In some embodiments, the phosphatidylcholine comprises less than or equal to about 8.5%, 5%, 4%, 3.7%, 2%, 1%, or 0.1% (or ranges including and/or spanning the aforementioned values) of any one or more of saturated fatty acids, monounsaturated fatty acids, polyunsaturated fatty acids (C 18), arachidonic acid (ARA) (C 20:4), docosahexaenoic acid DHA (C 22:6), phosphatidic acid, phosphatidylethanolamine, and/or lysophosphatidylcholine by weight. In some embodiments, the phosphatidylcholine has less than about 1.1% lysophosphatidylcholine and less than about 2.0% triglycerides by weight.

As disclosed elsewhere herein, in some embodiments, the lipid-based particle composition comprises one or more sterols. In some embodiments, the one or more sterols comprises one or more cholesterols, ergosterols, hopanoids, hydroxysteroids, phytosterols (e.g., vegapure), ecdysteroids, and/or steroids. In some embodiments, the sterol comprises cholesterol. In some embodiments, the sterol is cholesterol. In some embodiments, the only sterol present is cholesterol (e.g., the sterol lacks or substantially lacks sterols other than cholesterol). In some embodiments, the one or more sterol(s) (e.g., cholesterol, and/or other sterols), collectively or individually, are present in the aqueous composition at a concentration of less than or equal to about: 50 mg/ml, 40 mg/ml, 20 mg/ml, 10 mg/ml, 5 mg/ml, or ranges including and/or spanning the aforementioned values. In some embodiments, the one or more sterol(s) are present in the composition at a dry wt % of equal to or less than about: 0.25%, 0.5%, 1%, 5%, 7.5%, 10%, 15%, 20%, 25%, or ranges including and/or spanning the aforementioned values. In some embodiments, the one or more sterol(s) (collectively or individually) are present in the composition at a wet wt % of equal to or less than about: 0.1%, 0.25%, 0.5%, 1%, 2%, 3%, 4%, 5%, 7.5%, 10%, or ranges including and/or spanning the aforementioned values. In some embodiments, the cholesterol used in the composition comprises cholesterol from one or more of sheep's wool, synthetic cholesterol, or semisynthetic cholesterol from plant origin. In some embodiments, the sterol has a purity of greater than or equal to about: 92.5%, 95%, 96%, 98%, 99%, 99.9%, 100.0%, or ranges including and/or spanning the aforementioned values. In some embodiments, the sterol has a total % impurity content by weight of less than or equal to about: 8.5%, 5%, 4%, 3.7%, 2%, 1%, 0%, or ranges including and/or spanning the aforementioned values. In some embodiments, the sterol is cholesterol. In some embodiments, the sterol is not cholesterol. In some embodiments, the sterol is phytosterol.

As disclosed elsewhere herein, in some embodiments, the lipid-based particle composition comprises a lipid (e.g., a lipid that is not a phospholipid). In some embodiments, the lipid (or mixture of lipids) used in the composition is a liquid at room temperature. In some embodiments, the lipid(s) is one in which CBD is soluble. In some embodiments, the lipid(s) comprises one or more of a triglyceride(s) and/or one or more oils. In some embodiments, where the lipid is an oil, the oil may be hemp oil and/or marijuana oil. In some embodiments, the lipid (e.g., the triglyceride) comprises one or more medium chain triglycerides (MCTs). In some embodiments, the lipid comprises one or more medium chain triglycerides that can be an ester of glycerol and any one or more medium chain fatty acids. For instance, in some embodiments, the medium chain triglyceride comprises a fatty acid with an aliphatic tail 6-12 carbons in length (e.g., 6, 7, 8, 9, 10, 11, or 12) or combinations of different chain length fatty acids. Thus, in some embodiments, the MCT could comprise a tri-ester of glycerol and one fatty acid having an aliphatic chain length of 8, one fatty acid having an aliphatic chain length of 9, and one fatty acid having an aliphatic chain length of 10. In some embodiments, the MCT could comprise a tri-ester of glycerol and three fatty acid having an aliphatic chain that is the same length (e.g., each having a length of 8). In some embodiments, the medium chain fatty acids of the MCT include one or more of caprioc acid, heptanoic acid, octanoic acid, nonanoic acid, capric acid, undecanoic acid, and/or lauric acid, or any combination thereof. In some embodiments, the lipid comprises tristearin. In some embodiments, the lipid component comprises one or more long chain triglycerides. In some embodiments, the long chain triglyceride comprises a fatty acid having a tail that is greater than 12 carbons in length (e.g., greater than or equal to 13, 14, 15, 16, 17, 18, 19, or 20 carbons in length, or ranges including and/or spanning the aforementioned values) and glycerol. In some embodiments, the lipid is a triglyceride that is a tri-ester of fatty acids having aliphatic chain lengths 6 to 20 carbons in length. In some embodiments, the composition lacks long chain triglycerides. In some embodiments, the lipid comprises one or more of tricaprin, trilaurin, trimyristin, tripalmitin, and tristearin. In some embodiments, the one or more lipid(s) (e.g., MCT, LCT, or both), collectively or individually, are present in the aqueous composition at a concentration of less than or equal to about: 400 mg/ml, 300 mg/ml, 200 mg/ml, 150 mg/ml, 100 mg/ml, 93 mg/ml, 75 mg/ml, 50 mg/ml, 25 mg/ml, or ranges including and/or spanning the aforementioned values. In some embodiments, the one or more lipids are present in the composition (collectively or individually) at a dry wt % of equal to or less than about: 2.5%, 5%, 10%, 15%, 20%, 30%, 40%, 50%, 60%, or ranges including and/or spanning the aforementioned values. In some embodiments, the one or more lipids (collectively or individually) are present in the composition at a wet wt % of equal to or less than about: 2.5%, 5%, 7.5%, 10%, 12.5%, 15%, 20%, 30%, 40%, or ranges including and/or spanning the aforementioned values. In some embodiments, the lipid has a purity of greater than or equal to about: 92.5%, 95%, 96%, 98%, 99%, 99.9%, or ranges including and/or spanning the aforementioned values. In some embodiments, the lipid has a total % impurity content by weight of less than or equal to about: 8.5%, 5%, 4%, 3.7%, 2%, 1%, 0%, or ranges including and/or spanning the aforementioned values.

In some embodiments, the lipid that is not a phospholipid is not an MCT or LCT but is an MCT-substitute. In some embodiments, the MCT-substitute lipid (e.g., the non-phospholipid lipid) is selected from one or more of oleic acid, capric acid, caprylic acid, and triglycerides of such (Captex 8000, Captex GTO, Captex 1000), glycerol monooleate, glycerol monostearate (Geleol™ Mono and Diglyceride NF), omega-3 fatty acids (α-linolenic acid (ALA), eicosapentaenoic acid (EPA), docosahexaenoic acid (DHA), Tonalin, Pronova Pure® 46:38, free fatty acid Tonalin FFA 80), conjugated linoleic acid, alpha glycerylphosphorylcholine (alpha GPC), palmitoylethanolamide (PEA), cetyl alcohol, or emulsifying wax. In some embodiments, the one or more MCT-substitute lipids are present in the lipid-based particle composition (collectively or individually) at a dry wt % of equal to or less than about: 0.5%, 1.0%, 2.5%, 5%, 10%, 15%, 20%, 30%, 40%, 50%, 60%, 80% or ranges including and/or spanning the aforementioned values. In some embodiments, the one or more MCT-substitute lipids (collectively or individually) are present in the composition at a wet wt % of equal to or less than about: 0.5%, 1.0% 2.5%, 5%, 7.5%, 10%, 12.5%, 15%, 20%, 30%, 40%, 60% or ranges including and/or spanning the aforementioned values. In some embodiments, the MCT-substitute lipid has a purity of greater than or equal to about: 70%, 80%, 85%, 92.5%, 95%, 96%, 98%, 99%, 99.9%, 100%, or ranges including and/or spanning the aforementioned values. In some embodiments, the MCT-substitute lipid has a total % impurity content by weight of less than or equal to about: 8.5%, 5%, 4%, 3.7%, 2%, 1%, 0%, or ranges including and/or spanning the aforementioned values.

In some embodiments, a lipid that, when mixed with the CBD at a wt % of equal to or less than about: 1%, 2.5%, 5%, 7.5%, 10%, 15%, 18%, 20%, 25%, (or ranges including and/or spanning the aforementioned values), the CBD isolate is soluble and stable for a period of less than about 30 days (e.g., has degradation of less than or equal to about: 0.5%, 1%, 2%, 10%, 15%, or ranges including and/or spanning the aforementioned values). In some embodiments, as disclosed elsewhere herein, the non-phospholipid lipid is an MCT.

In some embodiments, the lipid-based particle composition comprises a preservative. In some embodiments, the preservative includes one or more benzoates (such as sodium benzoate or potassium benzoate), nitrites (such as sodium nitrite), sulfites (such as sulfur dioxide, sodium or potassium sulphite, bisulphite or metabisulphite), sorbates (such as sodium sorbate, potassium sorbate), ethylenediaminetetraacetic acid (EDTA) (and/or the disodium salt thereof), polyphosphates, organic acids (e.g., citric, succinic, malic, tartaric, benzoic, lactic and propionic acids), and/or antioxidants (e.g., vitamins such as vitamin E and/or vitamin C, butylated hydroxytoluene). In some embodiments, the one or more preservatives, collectively or individually, are present in the aqueous composition at a concentration of less than or equal to about: 10 mg/ml, 5 mg/ml, 1 mg/ml, 0.85 mg/ml, 0.5 mg/ml, 0.1 mg/ml, or ranges including and/or spanning the aforementioned values. In some embodiments, the one or more preservatives (collectively or individually) are present in the composition at a dry wt % of equal to or at less than about: 0.01%, 0.1%, 0.25%, 0.5%, 1%, 5%, 7.5%, 10%, 15%, 20%, 25%, or ranges including and/or spanning the aforementioned values. In some embodiments, the one or more preservatives (collectively or individually) are present in the composition at a wet wt % of equal to or less than about: 0.001%, 0.01%, 0.025%, 0.05%, 0.1%, 0.5%, 0.75%, 1.0%, 1.5%, 2.0%, 2.5%, 5%, or ranges including and/or spanning the aforementioned values. In some embodiments, the aqueous composition comprises one or more of malic acid at about 0.85 mg/ml, citric acid at about 0.85 mg/ml, potassium sorbate at about 1 mg/ml, and sodium benzoate at about 1 mg/ml. In some embodiments, the preservatives inhibit or prevent growth of mold, bacteria, and fungus. In some embodiments, Vitamin E is added at 0.5 mg/ml to act as an antioxidant in the oil phase. In some embodiments, the preservative concentrations may be changed depending on the flavored oil used.

In some embodiments, the lipid-based particle composition comprises one or more flavoring agents. In some embodiments, the one or more flavoring agent(s), collectively or individually, are present in the aqueous composition at a concentration of less than or equal to about: 5 mg/ml, 1.5 mg/ml, 1.2 mg/ml, 1 mg/ml, 0.9 mg/ml, 0.5 mg/ml, 0.1 mg/ml, or ranges including and/or spanning the aforementioned values. In some embodiments, the one or more flavoring agent(s) (collectively or individually) are present in the composition at a dry wt % of equal to or less than about: 0.01%, 0.1%, 0.25%, 0.5%, 1%, 5%, 7.5%, 10%, 15%, 20%, 25%, or ranges including and/or spanning the aforementioned values. In some embodiments, the one or more flavoring agents (collectively or individually) are present in the composition at a wet wt % of equal to or less than about: 0.001%, 0.01%, 0.025%, 0.05%, 0.1%, 0.5%, 0.75%, 1.0%, 1.5%, 2.0%, 2.5%, 5.0%, or ranges including and/or spanning the aforementioned values. In some embodiments, the one or more flavoring agents of the composition comprise monk fruit extract (e.g., MonkGold50), stevia, peppermint oil, lemon oil, vanilla, or the like, or combinations thereof. In some embodiments, the composition contains MonkGold50 at 0.9 mg/ml and flavored oils as flavoring. Examples of flavored oils are peppermint and lemon at 1.2 mg/ml. Chemicals that are not oil may also be used for flavor, for example, such as dry powders that replicate a flavor such as vanilla.

In some embodiments, the aqueous lipid-based particle composition comprises phosphatidylcholine in a range from about 8% to about 12%, MCT in a range from about 8% to about 12%, CBD in a range from about 1% to about 5%, cholesterol in a range from about 0.5% to about 4%, and water in a range from about 60% to about 90%. In some embodiments, the aqueous composition further comprises one or more of vitamin E in a range from about 0.01% to about 1.0%, malic acid in a range from about 0.01% to about 1.0%, citric acid in a range from about 0.01% to about 1.0%, potassium sorbate in a range from about 0.01% to about 2.0%, sodium benzoate in a range from about 0.01% to about 2.0%, and/or monk fruit extract in a range from about 0.01% to about 2.0%. In some embodiments, as disclosed elsewhere herein, the composition is aqueous and includes CBD at about 20 mg/ml, phosphatidylcholine at about 100 mg/ml, cholesterol at about 10 mg/ml, and MCT at about 93 mg/ml.

In some embodiments, the aqueous lipid-based particle composition comprises phosphatidylcholine in a range from about 9% to about 11%, MCT in a range from about 8% to about 10%, CBD in a range from about 1% to about 3%, cholesterol in a range from about 0.5% to about 2%, and water in a range from about 70% to about 80%. In some embodiments, the aqueous composition further comprises one or more of vitamin E in a range from about 0.01% to about 1.0%, malic acid in a range from about 0.01% to about 1.0%, citric acid in a range from about 0.01% to about 1.0%, potassium sorbate in a range from about 0.01% to about 2.0%, sodium benzoate in a range from about 0.01% to about 2.0%, and/or monk fruit extract in a range from about 0.01% to about 2.0%.

In some embodiments, the lipid-based particle composition comprises (in dry wt %) phosphatidylcholine in a range from about 40% to about 50%, MCT in a range from about 35% to about 45%, CBD in a range from about 5% to about 25%, and cholesterol in a range from about 2.5% to about 10%. In some embodiments, the composition further comprises (in dry weight) one or more of vitamin E in a range from about 0.01% to about 2.0%, malic acid in a range from about 0.01% to about 2.0%, citric acid in a range from about 0.01% to about 2.0%, potassium sorbate in a range from about 0.01% to about 2.0%, sodium benzoate in a range from about 0.01% to about 2.0%, and/or monk fruit extract in a range from about 0.01% to about 2.0%.

In some embodiments, the lipid-based particle composition comprises (in dry wt %) phosphatidylcholine in a range from about 42% to about 46%, MCT in a range from about 39% to about 43%, CBD in a range from about 5% to about 15%, and cholesterol in a range from about 2.5% to about 7%. In some embodiments, the composition further comprises (in dry weight) one or more of vitamin E in a range from about 0.01% to about 2.0%, malic acid in a range from about 0.01% to about 2.0%, citric acid in a range from about 0.01% to about 2.0%, potassium sorbate in a range from about 0.01% to about 2.0%, sodium benzoate in a range from about 0.01% to about 2.0%, and/or monk fruit extract in a range from about 0.01% to about 2.0%. As disclosed elsewhere herein, the composition can be varied such that the different ratios of the components yield a nanoparticle containing CBD that is stable.

In some embodiments, a solid lipid nanoparticle of the lipid-based particle compositions comprises a lipid core matrix. In some embodiments, the lipid core matrix is solid. In some embodiments, the solid lipid comprises one or more ingredients as disclosed elsewhere herein. In some embodiments, the core of the solid lipid comprises one or more triglycerides (e.g., tristearin), diglycerides (e.g. glycerol bahenate), monoglycerides (e.g. glycerol monostearate), fatty acids (e.g. stearic acid), steroids (e.g. cholesterol), and waxes (e.g. cetyl palmitate). In some embodiments, emulsifiers can be used to stabilize the lipid dispersion (with respect to charge and molecular weight). In some embodiments, the core ingredients and/or the emulsifiers are present in the composition (collectively or individually) at a dry wt % of equal to or less than about: 0.5%, 1.0%, 2.5%, 5%, 10%, 15%, 20%, 30%, 40%, 50%, 60%, 80% or ranges including and/or spanning the aforementioned values. In some embodiments, the core ingredients and/or the emulsifiers (collectively or individually) are present in the composition at a wet wt % of equal to or less than about: 0.5%, 1.0% 2.5%, 5%, 7.5%, 10%, 12.5%, 15%, 20%, 30%, 40%, 60% or ranges including and/or spanning the aforementioned values. In some embodiments, the core ingredients and/or the emulsifiers have a purity of greater than or equal to about: 70%, 80%, 85%, 92.5%, 95%, 96%, 98%, 99%, 99.9%, 100%, or ranges including and/or spanning the aforementioned values.

In some embodiments, the lipid-based particle composition (e.g., when in water or dried) comprises multilamellar nanoparticle vesicles, unilamellar nanoparticle vesicles, multivesicular nanoparticles, emulsion particles, irregular particles with lamellar structures and bridges, partial emulsion particles, combined lamellar and emulsion particles, and/or combinations thereof. In some embodiments, the composition is characterized by having multiple types of particles (e.g., lamellar, emulsion, irregular, etc.). In other embodiments, a majority of the particles present are emulsion particles. In several embodiments, a majority of the particles present are lamellar (multilamellar and/or unilamellar). In other embodiments, a majority of the particles present are irregular particles. In still other embodiments, a minority of the particles present are emulsion particles. In some embodiments, a minority of the particles present are lamellar (multilamellar and/or unilamellar). In other embodiments, a minority of the particles present are irregular particles.

In some embodiments, of the particles present in the composition (e.g., the aqueous composition), equal to or at least about 5%, 8%, 9%, 10%, 15%, 25%, 50%, 75%, 85%, 95%, or 100% (or ranges spanning and/or including the aforementioned values) are multilamellar nanoparticle vesicles. In some embodiments, of the particles present in the composition (e.g., the aqueous composition), equal to or at least about 5%, 8%, 9%, 10%, or 15% (or ranges spanning and/or including the aforementioned values) are multilamellar nanoparticle vesicles. In some embodiments, about 8.6% of the particles present are multilamellar.

In some embodiments, of the particles present in the composition (e.g., the aqueous composition), equal to or at least about 5%, 8%, 9%, 10%, 15%, 25%, 50%, 75%, 85%, 95%, or 100% (or ranges spanning and/or including the aforementioned values) are unilamellar nanoparticle vesicles. In some embodiments, of the particles present in the composition (e.g., the aqueous composition), equal to or at least about 5%, 8%, 9%, 10%, 15%, or 20% (or ranges spanning and/or including the aforementioned values) are unilamellar nanoparticle vesicles. In some embodiments, 12.88% of the particles present are unilamellar.

In some embodiments, of the particles present in the composition (e.g., the aqueous composition), equal to or at least about 5%, 8%, 9%, 10%, 15%, 25%, 50%, 75%, 85%, 95%, or 100% (or ranges spanning and/or including the aforementioned values) are emulsion particles. In some embodiments, of the particles present in the composition (e.g., the aqueous composition), equal to or at least about 60%, 65%, 70%, 75%, 85%, 95%, or 100% (or ranges spanning and/or including the aforementioned values) are emulsion particles. In some embodiments, 69.7% of the particles present are emulsion particles.

In some embodiments, of the particles present in the composition (e.g., the aqueous composition), equal to or at least about 1%, 2%, 3%, 5%, 8%, 9%, 10%, 15%, 25%, 50%, 75%, 85%, 95%, or 100% (or ranges spanning and/or including the aforementioned values) are irregular particles (e.g., with lamellar structures and/or bridges). In some embodiments, of the particles present in the composition (e.g., the aqueous composition), equal to or at least about 1%, 2%, 3%, 5%, 8%, 9%, or 10% (or ranges spanning and/or including the aforementioned values) are irregular particles. In some embodiments, 2.73% are irregular particles.

In some embodiments, of the particles present in the composition (e.g., the aqueous composition), equal to or at least about 5%, 8%, 9%, 10%, 15%, 25%, 50%, 75%, 85%, 95%, or 100% (or ranges spanning and/or including the aforementioned values) are combined lamellar and emulsion particles. In some embodiments, of the particles present in the composition (e.g., the aqueous composition), equal to or at least about 5%, 8%, or 9% (or ranges spanning and/or including the aforementioned values) are combined lamellar and emulsion particles. In some embodiments, 6.06% of the particles are combined lamellar and emulsion particles.

In some embodiments, the composition (e.g., the aqueous composition) comprises between 60% and 80% emulsion particles. In some embodiments, the composition (e.g., the aqueous composition) comprises between 7.5% and 20% small unilamellar vesicles. In some embodiments, the composition (e.g., the aqueous composition) comprises between 5% and 15% multilamellar vesicles. In some embodiments, the composition (e.g., the aqueous composition) comprises between 3% and 10% combined lamellar and emulsion particles. In some embodiments, the composition (e.g., the aqueous composition) comprises between 1% and 6% irregular particles. In some embodiments, the composition (e.g., the aqueous composition) comprises between 65% and 75% emulsion particles. In some embodiments, the composition (e.g., the aqueous composition) comprises between 10% and 15% small unilamellar vesicles. In some embodiments, the composition (e.g., the aqueous composition) comprises between 5% and 12% multilamellar vesicles. In some embodiments, the composition (e.g., the aqueous composition) comprises between 4% and 8% combined lamellar and emulsion particles. In some embodiments, the composition (e.g., the aqueous composition) comprises between 1% and 4% irregular particles.

In some embodiments, the composition (e.g., the aqueous composition) comprises between 60% and 80% emulsion particles, between 7.5% and 20% small unilamellar vesicles, between 5% and 15% multilamellar vesicles, between 3% and 10% combined lamellar and emulsion particles, and between 1% and 6% irregular particles. In some embodiments, the composition (e.g., the aqueous composition) comprises between 65% and 75% emulsion particles, between 10% and 15% small unilamellar vesicles, between 5% and 12% multilamellar vesicles, between 4% and 8% combined lamellar and emulsion particles, and between 1% and 4% irregular particles. In some embodiments, the composition (e.g., the aqueous composition) comprises 69.7% emulsion particles, 12.88% small unilamellar vesicles, 8.64% multilamellar vesicles, 6.06% combined lamellar and emulsion particles, and 2.73% irregular particles.

In some embodiments, at ambient temperature an aqueous lipid-based composition as disclosed herein has a viscosity (in centipoise (cP)) of equal to or less than about: 1.0, 1.05, 1.1, 1.2, 1.5, 2.0, 5.0, 10.0, 20, 30, 50, 100, or ranges including and/or spanning the aforementioned values. In some embodiments, at about 25° C. or 26° C. and a concentration of 20 mg/ml in water, the lipid-based particle composition has a viscosity (in centipoise (cP)) of equal to or less than about: 1.0, 1.05, 1.1, 1.2, 1.5, 2.0, 5.0, 10.0, 20, 30, 50, 100, or ranges including and/or spanning the aforementioned values. In some embodiments, the viscosity of the CBD lipid nanoparticle aqueous solution is equal to or less than 5.0 Cp.

In some embodiments, the liposomes and/or a liquid (e.g., aqueous) composition comprising the nanoparticles as disclosed herein are lyophilized. In some embodiments, where lyophilization is used to prepare a liposomal and/or nanoparticle based powder, one or more lyoprotectant agents may be added. In some embodiments, an individual lyoprotectant agent may be present at a dry wt % equal to or less than the dry weight of the lipophilic ingredients. In some embodiments, the lyoprotectant agent(s) (collectively or individually) may be present at a dry wt % equal to or less than about: 5%, 10%, 15%, 20%, 30%, 40%, 50%, 60%, or ranges including and/or spanning the aforementioned values. In some embodiments, the lyoprotectant agent(s) (collectively or individually) may be present at a wet wt % of equal to or less than about: 2.5%, 5%, 7.5%, 10%, 12.5%, 15%, 20%, 30%, or ranges including and/or spanning the aforementioned values. In some embodiments, the lyoprotectant is selected from the group consisting of lactose, dextrose, trehalose, arginine, glycine, histidine, and/or combinations thereof.

As disclosed elsewhere herein, some embodiments pertain to methods of preparing lipid-based particle compositions comprising nanoparticles and/or liposomes. In some embodiments, the composition is prepared by forming a lipid-in-oil emulsion. In some embodiments, an oil-in-water emulsion can be prepared without the use of organic solvents as shown in FIG. 1 (e.g., in an organic solvent-free method). In some embodiments, solid ingredients 101 are added and dissolved into liquid ingredients 102. In some embodiments, for example, one or more of the sterol (e.g., cholesterol) and/or therapeutic agent (e.g., phytocannabinoid, CBD, etc.) can be dissolved in lipid oil (e.g., a medium chain triglyceride) and/or vitamin E. In some embodiments, the phospholipid (e.g., phosphatidylcholine) can be added with mixing. In some embodiments, when a well dispersed lipid phase is formed after mixing, the addition of water 103 (e.g., having a temperature of equal to or at least about: 10° C., 20° C., 30° C., 40° C., 50° C., 60° C., 80° C., or ranges including and/or spanning the aforementioned values) and additional mixing 104 achieves an oil-in-water emulsion 105. In some embodiments, the oil-in-water emulsion is then subject to high-shear mixing to form nanoparticles (e.g., CBD liposomes). In some embodiments, high-shear mixing 106 is performed using a high shear dispersion unit or an in-line mixer can be used to prepare the emulsions. In some embodiments, the particles can be made by solvent evaporation and/or solvent precipitation.

Figure 2:
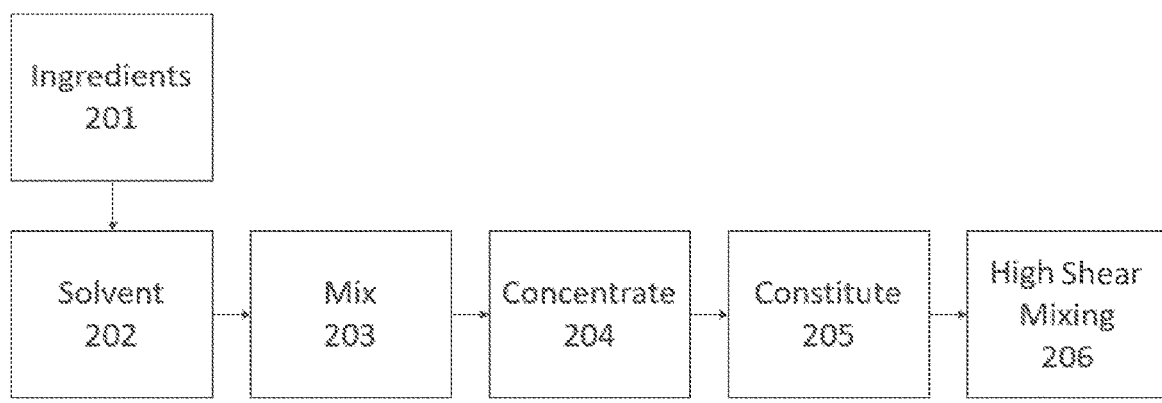
FIG. 2 is a flow chart showing another embodiment of a method for preparing a lipid-based particle composition as disclosed herein.

In some embodiments, as shown in FIG. 2, the lipid-in-oil emulsion is formed by dissolving ingredients 201, such as, one or more of a phospholipid (e.g., phosphatidylcholine), a sterol (e.g., cholesterol), a therapeutic agent (e.g., phytocannabinoid, CBD, etc.), a lipid (e.g., a medium chain triglyceride), and/or a preservative (e.g., vitamin E) in a solvent 202. In some embodiments, the solvent can include one or more organic solvents, including but not limited to, ethanol, chloroform, and/or ethyl acetate. In some embodiments, the solvents are class II solvents, class III solvents (e.g., at least class II and/or class III by the ICH Q3C standard), or mixtures thereof. In some embodiments, the solution of ingredients and solvent is dried 203. In some embodiments, after drying, the ingredients are provided as lipids and or liposomes as a thin film. In some embodiments, the solvent is removed from the composition by subjecting the solution to heat under vacuum to promote evaporation. In some embodiments, the film may further be dried under nitrogen gas. In some embodiments, the lipid film is hydrated 205 with warm aqueous solution to form an oil-in-water emulsion. In some embodiments, high-shear mixing is performed 206 using a high shear dispersion unit or an in-line mixer can be used to prepare the emulsions.

In some embodiments, as disclosed elsewhere herein, the lipid-in-water emulsion is subject to high pressure homogenization using a microfluidizer. In some embodiments, high sheer mixing can be used to reduce the particle size. In some embodiments, the oil-in-water emulsion is processed to a nanoparticle (e.g., about 20 to about 500 nm, etc.) using the microfluidizer or other high sheer processes. In some embodiments, the oil-in-water emulsion is processed to a nanoparticle having a size from about 80 nm to 180 nm in diameter or about 100 nm to about 150 nm in diameter.

In some embodiments, the lipid-in-water emulsion is passed through the microfluidizer a plurality of times (e.g., equal to or at least 1 time, 2 times, 3 times, 4 times, 5 times, 10 times, or ranges including and/or spanning the aforementioned values). In some embodiments, the emulsion is passed through the microfluidizer at a pressure of equal to or less than about: 5,000 PSI, 15,000 PSI, 20,000 PSI, 25,000 PSI, 30,000 PSI, or ranges including and/or spanning the aforementioned values. In some embodiments, the emulsion is passed through the microfluidizer at a temperature of equal to or at least about: 30° C., 40° C., 50° C., 65° C., 80° C., or ranges including and/or spanning the aforementioned values. In some embodiments, the emulsion is passed through the microfluidizer at least about room temperature (e.g., about 20° C. or about 25° C.) and/or without any heating and/or temperature control. In some embodiments, the emulsion is passed through the microfluidizer at a temperature of equal to or less than about 80° C. In some embodiments, the microfluidizer includes an interaction chamber consisting of 75 µm to 200 µm pore sizes and the emulsion is passed through this chamber. In some embodiments, the pore size of the microfluidizer are less than or equal to about: 75 µm, 100 µm, 150 µm, 200 µm, 250 µm, 300 µm, or ranges including and/or spanning the aforementioned values. In some embodiments, the nanoparticle composition is prepared by high shear mixing, sonication, or extrusion.

In some embodiments, after preparation, the lipid-based particle composition is characterized by an ability to pass through a 0.2 µm filter while preserving the nanoparticle structure (e.g., a change in average nanoparticle size of no greater than 10 nm, 20 nm, or 30 nm). In some embodiments, after passage through a 0.2 µm there is a change in average diameter of the particles of equal to or at less than about: 1%, 5%, 10%, 20%, or ranges including and/or spanning the aforementioned values. In some embodiments, after passage through a 0.2 µm there is a change in PDI of the particles of equal to or at less than about: 1%, 5%, 10%, 20%, or ranges including and/or spanning the aforementioned values.

In some embodiments, as disclosed elsewhere herein, the lipid-based particle composition is composed of highly pure ingredients, including GMP manufactured CBD isolate. In some embodiments, the CBD is triple checked for potency and purity, and has negligible concentrations of THC. In some embodiments, the composition (and/or one or more ingredients constituting the compositions) is manufactured with high purity, multicompendial ingredients to be at the same standards as pharmaceutical products. In some embodiments, the composition is manufactured using pharmaceutical equipment and documentation to ensure the product is of high quality and consistent from batch to batch.

In some embodiments, as disclosed elsewhere herein, the CBD nanoparticle composition imparts solubility to CBD (or another phytocannabinoid), which is highly insoluble, in a delivery system that is easily dispersible in aqueous solutions. CBD oils do not disperse well in aqueous solutions and have poor oral absorption. CBD particle formulations made using methods other than those disclosed herein have inconsistent particle size and may not be stable with storage over time.

In some embodiments, advantageously, the nanoparticle delivery systems of CBD disclosed herein are reproducibly manufacturable. In some embodiments, the method of manufacture of the compositions avoids the introduction of contaminants (such as metal contamination). In some embodiments, over 50%, 75%, 95% (or ranges spanning and or including the aforementioned values) of the nanoparticles prepared by the methods disclosed herein have a particle size of between about 20 to about 500 nm (as measured by zeta sizing (e.g., refractive index). In some embodiments, over 50%, 75%, 95% (or ranges spanning and or including the aforementioned values) of the nanoparticles prepared by the methods disclosed herein have a particle size of between about 50 nm to about 200 nm (as measured by zeta sizing (e.g., refractive index). In some embodiments, over 50%, 75%, 95% (or ranges spanning and or including the aforementioned values) of the nanoparticles prepared by the methods disclosed herein have a particle size of between about 90 nm to about 150 nm (as measured by zeta sizing (e.g., refractive index). In some embodiments, this consistency in size allows predictable delivery to subjects. In some embodiments, the D90 particle size measurement varies between 150 and 500 nm.

In some embodiments, the lipid-based delivery system described herein offers protection to CBD against degradation in an aqueous environment for long-term storage. In some embodiments, the CBD composition is well characterized to ensure a consistent product from batch to batch and with long-term stability. In some embodiments, the product stability is routinely tested for appearance, particle size and distribution, zeta potential, residual solvents, heavy metals, CBD concentration and related compounds, and microbial testing and the values measured using these test methods varies (over a period of at least about 1 month or about 6 months at 25° C. with 60% relative humidity) by less than or equal to about: 1%, 5%, 10%, 20%, 30%, or ranges including and/or spanning the aforementioned values. In some embodiments, the particle size and/or PDI varies over a period of at least about 1 month or about 6 months (at 25° C. with 60% relative humidity) by less than or equal to about: 1%, 5%, 10%, 20%, 30%, or ranges including and/or spanning the aforementioned values. As noted elsewhere herein, PDI and size can be measured using conventional techniques disclosed herein. In some embodiments, the CBD concentration varies over a period of at least about 1 month or about 6 months (at 25° C. with 60% relative humidity) by less than or equal to about: 1%, 5%, 10%, 15%, or ranges including and/or spanning the aforementioned values. As noted elsewhere herein, PDI and size can be measured using conventional techniques disclosed herein.

In some embodiments, the lipid-based particle compositions disclosed herein have a shelf life of equal to or greater than 6 months, 12 months, 14 months, 16 months, 18 months, 19 months, or ranges including and/or spanning the aforementioned values. The shelf-life can be determined as the period of time in which there is 95% confidence that at least 50% of the response (CBD concentration or particle size) is within the specification limit. This refers to a 95% confidence interval and when linear regression predicts that at least 50% of the response is within the set specification limit. For instance, in FIG. 3, the dashed line on the stability plot is the 95% confidence interval and the solid line is the linear regression. The dots are the responses. The response variable is either Z-average particle size or CBD concentration in FIGS. 3 and 4. In some embodiments, the particle size specification is 100 to 200 nm, the CBD concentration specification is 18 to 22 mg/mL. These are shown on the stability plot as the lower specification (LS) and the upper specification (US).

In some embodiments, the lipid-based particle composition contains preservatives that are proven to protect against bacteria, mold, and fungal growth. The product specification is no more than 100 cfu/gram. In some embodiments, over a period of about 1 month, about 6 months, or about 12 months the composition has equal to or not more than: 50 cfu/gram, 10 cfu/gram, 5 cfu/gram, 1 cfu/gram, 0.1 cfu/gram, or ranges including and/or spanning the aforementioned values. In some embodiments, 1 week at 20° C.-25° C. after a $10^5$-$10^7$ CFU/mL challenge with any one of *Staphylococcus aureus, Pseudomonas aeruginosa, Escherichia coli, Candida albicans*, and *Aspergillus brasiliensis* the composition has equal to or not more than: 100 cfu/gram, 50 cfu/gram, 25 cfu/gram, 10 cfu/gram, 5 cfu/gram, 1 cfu/gram, 0.1 cfu/gram, or ranges including and/or spanning the aforementioned values. In some embodiments, 1 week at 20° C.-25° C. after a $10^5$-$10^7$ CFU/mL challenge with any one of *Staphylococcus aureus, Pseudomonas aeruginosa, Escherichia coli, Candida albicans*, and *Aspergillus brasiliensis* the composition has a log reduction for the bacteria of equal to or greater than: 1, 2, 3, 4, 5, 10, or ranges including and/or spanning the aforementioned values.

In some embodiments, unlike other delivery systems, the lipid-based particle composition ingredients provided herein provides a proper ratio and/or combination of ingredients that allow it to maintain stability and efficacy as disclosed elsewhere herein (e.g., during long term storage for example).

In some embodiments, advantageously, the individual particles within the disclosed lipid-based particle compositions may not settle or sediment appreciably. In some embodiments, an appreciable amount of the composition (e.g., as viewed by the naked eye) does not settle and/or separate from an aqueous liquid upon standing. In some embodiments, the composition does not appreciably settle or separate from an aqueous liquid upon standing for equal to or at least about 1 day, at least about 1 month, about 3 months, about 6 months, about 9 months, about 1 year, or ranges including and/or spanning the aforementioned values. In some embodiments, upon standing, the composition remains dispersed in an aqueous liquid for at least about 1 day, at least about 1 month, about 3 months, about 6 months, about 9 months, about 1 year, or ranges including and/or spanning the aforementioned values. In some embodiments, the homogeneity of the disclosed compositions changes by equal to or less than about: 0.5%, 1%, 5%, 7.5%, 10%, or 15% (or ranges including and/or spanning the aforementioned values) after a period of one week or one month. In this case, homogeneity is observed through images by SEM or cyro-SEM (e.g., the average size of the particles and/or the particle types). In some embodiments, the composition remains dispersed in an aqueous liquid and does not appreciably settle or separate from an aqueous liquid after at least about: 1 minute, 5 minutes, 30 minutes, or an hour in a centrifuge at a centripetal acceleration of at least about 100 m/s, at least about 1000 m/s, or at least about 10,000 m/s. In some embodiments, the composition remains dispersed in an aqueous liquid and does not appreciably settle or separate from an aqueous liquid after at least about: 1 minute, 5 minutes, 30 minutes, or an hour in a centrifuge at a centrifuge speed of 5000 RPM, 10,000 RPM, or 15,000 RPM.

In some embodiments, as disclosed elsewhere herein, the nanoparticle delivery system aids in absorption of the CBD molecule when orally ingested. In some embodiments, the compositions disclosed herein allow CBD to be delivered to and/or absorbed through the gut. As disclosed elsewhere herein, some embodiments pertain to the use of the lipid-based nanodelivery system to protect the CBD molecule from degradation and/or precipitation in the aqueous solution it is stored in (e.g., in an aqueous composition for administration to a subject). In some embodiments, use of the delivery systems disclosed herein result in improved bioavailability and/or absorption rate. For instance, in some embodiments, the Cmax of a therapeutic is increased using a disclosed embodiment, the Tmax of is decreased using an embodiment as disclosed herein, and/or the AUC is increased using a disclosed embodiment.

In some embodiments, the pharmacokinetic outcomes disclosed elsewhere herein (Cmax, Tmax, AUC, $t_{1/2}$, etc.) can be achieved using aqueous lipid-based particle compositions or powdered lipid-based particle compositions (e.g., where the powder is supplied by itself, in a gel capsule, as an additive to food, etc.).

In some embodiments, the Cmax of the therapeutic (e.g., CBD) is increased using the disclosed embodiments relative to other delivery vehicles (e.g., after administration to a subject). In some embodiments, the Cmax is increased relative to CBD alone or comparator embodiments (e.g., CBD oil-based products) by equal to or at least about: 15%, 20%, 50%, 100%, 150%, 200%, or ranges including and/or spanning the aforementioned values. In some embodiments, the CBD Cmax is increased (relative to a CBD oil-based product) by equal to or at least about: 5%, 10%, 20%, 30%, 50%, 100%, or ranges including and/or spanning the aforementioned values. In some embodiments, the CBD Cmax is increased (relative to a CBD oil-based product) by equal to or at least about: 10 ng/mL, 20 ng/mL, 30 ng/mL, 40 ng/mL, 50 ng/mL, 60 ng/mL, 70 ng/mL, 80 ng/mL, 90 ng/mL, or ranges including and/or spanning the aforementioned values.

In some embodiments, after a dose of 15 mg CBD provided in an embodiment as disclosed herein to a subject (e.g., a mini-pig, human, etc.), the Cmax of CBD is equal to or at least about: 0.5 µg/L, 1 µg/L, 2 µg/L, 3 µg/L, 4 µg/L, 5 µg/L, 6 µg/L, or ranges including and/or spanning the aforementioned values. In some embodiments, after a dose of 15 mg/kg of CBD provided in an embodiment as disclosed herein to a subject, the Cmax of CBD is equal to or at least about: 40 ng/mL, 50 ng/mL, 60 ng/mL, 70 ng/mL, 80 ng/mL, 90 ng/mL, 100 ng/mL, 150 ng/mL, 200 ng/mL, or ranges including and/or spanning the aforementioned values.

In some embodiments, the Cmax for a disclosed embodiment is increased relative to an equal dose of a CBD oil-based comparator vehicle. In some embodiments, the Cmax for a disclosed embodiment is increased relative to a CBD oil-based comparator vehicle by equal to or at least about: 15%, 20%, 50%, 100%, 150%, 200%, or ranges including and/or spanning the aforementioned values. In some embodiments, these pharmacokinetic results can be achieved using aqueous compositions or powdered compositions (where the powder is supplied by itself, in a gel capsule, as an additive to food, etc.). In some instances, the Cmax using a disclosed embodiment is 1.25 times higher than when using a comparator delivery system (e.g., the Cmax of the comparator×1.25). In some instances, the Cmax using a disclosed embodiment is equal to or at least about 1.25 times higher, 1.5 times higher, 2 times higher, 3 times higher (or ranges including or spanning the aforementioned values) than when using a comparator delivery system.

In some embodiments, the Tmax for CBD using a disclosed embodiment is shortened relative to other vehicles. In some embodiments, after a dose of CBD provided in an embodiment as disclosed herein to a subject as disclosed herein, the Tmax of CBD is equal to or at less than about: 30 minutes, 1 hours, 2 hours, 3 hours, 4 hours, 4.5 hours, 5 hours, 5.5 hours, 6 hours, 6.5 hours, 7 hours, 8 hours, or ranges including and/or spanning the aforementioned values. In some embodiments, after a dose of 15 mg/kg of CBD provided in an embodiment as disclosed herein to a subject, the Tmax of CBD is equal to or at less than about: 30 minutes, 1 hours, 2 hours, 3 hours, 4 hours, 5 hours, 5.5 hours, 6 hours, 6.5 hours, 7 hours, 8 hours, or ranges including and/or spanning the aforementioned values. In some embodiments, after a dose of CBD provided in an embodiment as disclosed herein to a subject, the Tmax of CBD is between about 4 hours and about 6.5 hours or between about 3 hours and about 7 hours. In some embodiments, after a dose of 15 mg of CBD provided in an embodiment as disclosed herein to a human patient, the Tmax of CBD is equal to or less than about: 3 hours, 4 hours, 5 hours, 6 hours, 7 hours, 8 hours, or ranges including and/or spanning the aforementioned values.

In some embodiments, the Tmax for CBD using a disclosed embodiment is improved relative to oil-based CBD vehicles (e.g., has a shorter duration to Tmax). In some embodiments, using an embodiment as disclosed herein, the Tmax for CBD is shortened relative to comparable delivery vehicles (e.g., an oil-based CBD vehicle) by equal to or at least about: 5%, 10%, 15%, 20%, 25%, 50%, or ranges including and/or spanning the aforementioned values. In some embodiments, the Tmax is shortened relative to CBD alone by equal to or at least about: 5%, 10%, 15%, 20%, 25%, or ranges including and/or spanning the aforementioned values. In some embodiments, the Tmax for a disclosed embodiment is decreased relative to a CBD oil-based comparator vehicle by equal to or at least about: 15%, 20%, 50%, 100%, 150%, 200%, or ranges including and/or spanning the aforementioned values. In some embodiments, the Tmax of CBD for a disclosed embodiment is decreased relative to a CBD oil-based comparator vehicle by equal to or at least about: 15 minutes, 30 minutes, 45 minutes, 1 hour, 2 hours, or ranges including and/or spanning the aforementioned values. In some instances, the Tmax is a fraction of that achieved using a comparator delivery system. In some instances, the time to Tmax using a disclosed embodiment is 0.5 times, 0.7 times, 0.8 times, 0.9 times, or 0.95 times the Tmax of a comparator delivery system (or ranges including or spanning the aforementioned values).

In some embodiments, after of a dose of CBD (e.g., a 15 mg/kg dose) provided in an embodiment as disclosed herein to a subject (e.g., a mini-pig, human, etc.), the AUC of CBD is equal to or at least about: 50 ng/mL*hr, 100 ng/mL*hr, 200 ng/mL*hr, 300 ng/mL*hr, 400 ng/mL*hr, 450 ng/mL*hr, 500 ng/mL*hr, 550 ng/mL*hr, 600 ng/mL*hr, 650 ng/mL*hr, 700 ng/mL*hr, 800 ng/mL*hr, 1000 ng/mL*hr, or ranges including and/or spanning the aforementioned values.

In some embodiments, the AUC for CBD using a disclosed embodiment is increased (relative to CBD or a comparator delivery vehicle) by equal to or at least about: 50 ng/mL*hr, 100 ng/mL*hr, 200 ng/mL*hr, 300 ng/mL*hr, 400 ng/mL*hr, or ranges including and/or spanning the aforementioned values. In some embodiments, the AUC using a disclosed embodiment is increased (relative to CBD or a comparator delivery vehicle) by equal to or at least about: 5%, 10%, 20%, 30%, or ranges including and/or spanning the aforementioned values. In some embodiments, the AUC is improved relative to CBD alone or a CBD in oil mixture by equal to or at least about: 5%, 25%, 50%, 100%, 150%, 200%, or ranges including and/or spanning the aforementioned values. In some instances, the AUC using a disclosed embodiment is 1.25 times higher than when using a comparator delivery system. In some instances, the AUC using a disclosed embodiment is equal to or at least about 1.25 times higher, 1.5 times higher, 2 times higher, 3 times higher (or ranges including or spanning the aforementioned values) than when using a comparator delivery system.

In some embodiments, after of a dose of 15 mg/kg of CBD to a subject as disclosed herein, the AUC for the time period from administration to 4 hours post administration using a disclosed embodiment is equal to or at least about: 40 ng/mL*hr, 50 ng/mL*hr, 75 ng/mL*hr, 100 ng/mL*hr, 200 ng/mL*hr, 300 ng/mL*hr, 400 ng/mL*hr, 450 ng/mL*hr, or ranges including and/or spanning the aforementioned values. In some embodiments, after of a dose of 15 mg/kg of CBD to a subject, the AUC for the time period from administration to 4 hours post administration using a disclosed embodiment is increased (e.g., relative to CBD or a comparator delivery vehicle) by equal to or at least about: 15 ng/mL*hr, 25 ng/mL*hr, 50 ng/mL*hr, 75 ng/mL*hr, or ranges including and/or spanning the aforementioned values. In some embodiments, after of a dose of 15 mg/kg of CBD to a subject, the AUC for the time period from administration to 4 hours post administration using a disclosed embodiment is increased (e.g., relative to CBD or a comparator delivery vehicle) by equal to or at least about: 5%, 10%, 20%, 25%, 30%, 50%, 100%, 150%, 200%, or ranges including and/or spanning the aforementioned values. In some embodiments, the AUC for the time period from administration to 4 hours post administration using a disclosed embodiment is double that of a comparator delivery system, triple that of a comparator delivery system, quadruple that of a comparator delivery system, or higher.

In some embodiments, after of a dose of 15 mg/kg of CBD to a subject as disclosed herein, the AUC for the time period from 4 hours post administration to 6 hours post administration using a disclosed embodiment is equal to or at least about: 40 ng/mL*hr, 50 ng/mL*hr, 75 ng/mL*hr, 100 ng/mL*hr, 200 ng/mL*hr, 300 ng/mL*hr, 400 ng/mL*hr, 450 ng/mL*hr, or ranges including and/or spanning the aforementioned values. In some embodiments, after of a dose of 15 mg/kg of CBD to a subject, the AUC for the time period from 4 hours post administration to 6 hours post administration using a disclosed embodiment is increased (e.g., relative to CBD or a comparator delivery vehicle) by equal to or at least about: 15 ng/mL*hr, 25 ng/mL*hr, 50 ng/mL*hr, 75 ng/mL*hr, or ranges including and/or spanning the aforementioned values. In some embodiments, after of a dose of 15 mg/kg of CBD to a subject, the AUC for the time period from 4 hours post administration to 6 hours post administration using a disclosed embodiment is increased (e.g., relative to CBD or a comparator delivery vehicle) by equal to or at least about: 5%, 10%, 20%, 25%, 30%, 50%, 100%, 150%, 200%, or ranges including and/or spanning the aforementioned values. In some embodiments, the AUC for the time period from 4 hours post administration to 6 hours post administration using a disclosed embodiment is double that of a comparator delivery system, triple that of a comparator delivery system, quadruple that of a comparator delivery system, or higher.

In some embodiments, the half-life for CBD ($t_{1/2}$) in vivo using a disclosed embodiment can be shorter relative to other vehicles. In some embodiments, after a dose of CBD provided in an embodiment as disclosed herein to a subject as disclosed herein, the $t_{1/2}$ of CBD is equal to or at less than about: 4 hours, 5 hours, 5.5 hours, 6 hours, 6.5 hours, or ranges including and/or spanning the aforementioned values. In some embodiments, after a dose of CBD provided in an embodiment as disclosed herein to a subject, the $t_{1/2}$ of CBD is between about 4 hours and about 6.5 hours or between about 3 hours and about 7 hours. In some embodiments, the $t_{1/2}$ for a disclosed embodiment is decreased relative to a CBD oil-based comparator vehicle by equal to or at least about: 15%, 20%, 50%, 100%, 150%, 200%, or ranges including and/or spanning the aforementioned values. In some embodiments, the $t_{1/2}$ of CBD for a disclosed embodiment is decreased relative to a CBD oil-based comparator vehicle by equal to or at least about: 15 minutes, 30 minutes, 45 minutes, 1 hour, 2 hours, or ranges including and/or spanning the aforementioned values. In some instances, the $t_{1/2}$ is a fraction of that achieved using a comparator delivery system. In some instances, the time to $t_{1/2}$ using a disclosed embodiment is 0.5 times, 0.7 times, 0.8 times, 0.9 times, or 0.95 times the $t_{1/2}$ of a comparator delivery system (or ranges including or spanning the aforementioned values).

For brevity, the Cmax, Tmax, AUC, and $t_{1/2}$ results provided above are disclosed with specific reference to CBD as the active agent. The above pharmacokinetic results (including Cmax, Tmax, AUC, and $t_{1/2}$) are also expected for other phytocannabinoids and/or other therapeutic agents as disclosed elsewhere herein.

In some embodiments, the lipid-based particle composition comprises nanoparticles having an average size of less than or equal to about: 10 nm, 50 nm, 100 nm, 250 nm, 500 nm, 1000 nm, or ranges including and/or spanning the aforementioned values. In some embodiments, the composition comprises nanoparticles having an average size of between about 50 nm and 150 nm or between about 50 and about 250 nm. In some embodiments, the size distribution of the nanoparticles for at least 50%, 75%, 80%, 90% (or ranges including and/or spanning the aforementioned percentages) of the particles present is equal to or less than about: 20 nm, 40 nm, 60 nm, 80 nm, 100 nm, 110 nm, 120 nm, 130 nm, 140 nm, 160 nm, 180 nm, 200 nm, 300 nm, 400 nm, 500 nm, or ranges including and/or spanning the aforementioned nm values. In some embodiments, the composition comprises nanoparticles having an average size of less than or equal to about: 10 nm, 50 nm, 100 nm, 250 nm, 500 nm, 1000 nm, or ranges including and/or spanning the aforementioned values. In some embodiments, the size distribution of the nanoparticles for at least 90% of the particles present is equal to or less than about: 20 nm, 40 nm, 60 nm, 80 nm, 100 nm, 110 nm, 120 nm, 130 nm, 140 nm, 160 nm, 180 nm, 200 nm, 300 nm, 400 nm, 500 nm, or ranges including and/or spanning the aforementioned nm values. In some embodiments, the size distribution of the nanoparticles for at least 90% of the particles present is equal to or less than about: 100 nm, 110 nm, 120 nm, 130 nm, 140 nm, 160 nm, 180 nm, 200 nm, or ranges including and/or spanning the aforementioned nm values. In some embodiments, the D90 of the particles present is equal to or less than about: 80 nm, 100 nm, 110 nm, 120 nm, 130 nm, 140 nm, 160 nm, 180 nm, 200 nm, 300 nm, 400 nm, 500 nm, or ranges including and/or spanning the aforementioned values. In some embodiments, the size of the nanoparticle is the diameter of the nanoparticle as measured using any of the techniques as disclosed elsewhere herein. For instance, in some embodiments, the size of the nanoparticle is the measured using dynamic light scattering. In some embodiments, the size of the nanoparticle is the measured using a zeta sizer.

In some embodiments, the average size of the nanoparticles of a composition as disclosed herein is substantially constant and/or does not change significantly over time (e.g., it is a stable nanoparticle). In some embodiments, after formulation and storage for a period of at least about 1 month (30 days), about 3 months (90 days), or about 6 months (180 days) (e.g., at ambient conditions, at 25° C. with 60% relative humidity, or under the other testing conditions disclosed elsewhere herein), the average size of nanoparticles comprising the composition changes less than or equal to about: 1%, 5%, 10%, 20%, or ranges including and/or spanning the aforementioned values.

In some embodiments, the polydispersity index (PDI) of the nanoparticles of a composition as disclosed herein is less than or equal to about: 0.05, 0.10, 0.15, 0.20, 0.25, 0.30, 0.40, 0.50, 0.60, 0.70, 0.80, or ranges including and/or spanning the aforementioned values. In some embodiments, the size distribution of the nanoparticles is highly monodisperse with a polydispersity index of less than or equal to about: 0.05, 0.10, 0.15, 0.20, 0.25, or ranges including and/or spanning the aforementioned values.

In some embodiments, the zeta potential of the nanoparticles of a composition as disclosed herein is less than or equal to about: 1 mV, 3 mV, 4 mV, 5 mV, 6 mV, 7 mV, 8 mV, 10 mV, 20 mV, or ranges including and/or spanning the aforementioned values. In some embodiments, the zeta potential of the nanoparticles is greater than or equal to about: −3 mV, −1 mV, 0 mV, 1 mV, 3 mV, 4 mV, 5 mV, 6 mV, 7 mV, 8 mV, 4 mV, 10 mV, 20 mV, or ranges including and/or spanning the aforementioned values. In some embodiments, the zeta potential and/or diameter of the particles (e.g., measured using dynamic light scattering) is acquired using a zetasizer (e.g., a Malvern ZS90 or similar instrument).

In some embodiments, the lipid-based particle composition has a pH of less than or equal to about: 2, 3, 4, 5, 6, 6.5, 7, 8, 9, or ranges including and/or spanning the aforementioned values. In some embodiments, the composition has a pH of greater than or equal to about: 2, 3, 4, 5, 6, 6.5, 7, 8, 9, or ranges including and/or spanning the aforementioned values.

In some embodiments, as disclosed elsewhere herein, the lipid-based particle composition is stable. In some embodiments, for example, after formulation (e.g., in water at concentrations disclosed elsewhere herein) and storage for a period of at least about 1 month, 3 months, or about 6 months, the polydispersity of the nanoparticles changes less than or equal to about: 1%, 5%, 10%, 20%, or ranges including and/or spanning the aforementioned values. In some embodiments, after formulation (e.g., in water at concentrations disclosed elsewhere herein) and storage for a period of at least about 1 month, 3 months, or about 6 months, the soluble fraction of CBD in the formulation changes less than or equal to about: 1%, 5%, 10%, 20%, 30%, or ranges including and/or spanning the aforementioned values. In some embodiments, after formulation and storage for a period of at least about 1 month or about 6 months (e.g., at ambient conditions, at 25° C. with 60% relative humidity, or under the other testing conditions disclosed elsewhere herein), the PDI of nanoparticles comprising the composition changes by less than or equal to about: 1%, 5%, 10%, 20%, or ranges including and/or spanning the aforementioned values. In some embodiments, after formulation and storage for a period of at least about 1 month or about 6 months (e.g., at ambient conditions, at 25° C. with 60% relative humidity, or under the other testing conditions disclosed elsewhere herein), the PDI of nanoparticles comprising the composition changes by less than or equal to about: 0.05, 0.1, 0.2, 0.3, 0.4, or ranges including and/or spanning the aforementioned values.

In some embodiments, when exposed to simulated gastric fluid (e.g., at a concentration of 20 mg/mL), the particle size of the nanoparticles of a composition as disclosed herein does not change and/or changes less than 5% during a period of greater than or equal to about: 1 hour, 2 hours, 3 hours, 4 hours, 5 hours, 6 hours, 10 hours, or ranges including and/or spanning the aforementioned values. In some embodiments, when exposed to simulated intestinal fluid (e.g., at a concentration of 20 mg/mL), the particle size of the nanoparticles disclosed herein does not change and/or changes less than 5% during a period of greater than or equal to about: 1 hour, 2 hours, 3 hours, 4 hours, 5 hours, 6 hours, 10 hours, or ranges including and/or spanning the aforementioned values. In some embodiments, after formulation (e.g., at a concentration of 20 mg/mL) and storage in simulated gastric fluid for a period of at least about 1 hour or about 2 hours (e.g., at 37° C., or under the other testing conditions disclosed elsewhere herein), the average particle size of nanoparticles comprising the composition changes by less than or equal to about: 1%, 5%, 10%, 20%, 50%, or ranges including and/or spanning the aforementioned values. In some embodiments, after formulation (e.g., at a concentration of 20 mg/mL) and storage in simulated gastric fluid for a period of at least about 1 hour, about 2 hours, about 3 hours, or about 4 hours (e.g., at 37° C. or under the other testing conditions disclosed elsewhere herein), the PDI of nanoparticles comprising the composition changes by less than or equal to about: 1%, 5%, 10%, 20%, or ranges including and/or spanning the aforementioned values. In some embodiments, after formulation (e.g., at a concentration of 20 mg/mL) and storage in simulated gastric fluid for a period of at least about 1 hour or about 2 hours (e.g., at 37° C. or under the other testing conditions disclosed elsewhere herein), the PDI of nanoparticles comprising the composition changes by less than or equal to about: 0.01, 0.05, 0.1, 0.2, 0.3, or ranges including and/or spanning the aforementioned values. In some embodiments, after formulation (e.g., at a concentration of 20 mg/mL) and storage in simulated intestinal fluid for a period of at least about 1 hour or about 2 hours (e.g., at 37° C., or under the other testing conditions disclosed elsewhere herein or under the other testing conditions disclosed elsewhere herein), the average particle size of nanoparticles comprising the composition changes by less than or equal to about: 1%, 5%, 10%, 20%, 50%, or ranges including and/or spanning the aforementioned values. In some embodiments, after formulation (e.g., at a concentration of 20 mg/mL) and storage in simulated intestinal fluid for a period of at least about 1 hour, about 2 hours, about 3 hours, or about 4 hours (e.g., at 37° C. or under the other testing conditions disclosed elsewhere herein), the PDI of nanoparticles comprising the composition changes by less than or equal to about: 1%, 5%, 10%, 20%, 100%, 150%, or ranges including and/or spanning the aforementioned values. In some embodiments, after formulation (e.g., at a concentration of 20 mg/mL) and storage in simulated intestinal fluid for a period of at least about 1 hour, about 2 hours (e.g., at 37° C. or under the other testing conditions disclosed elsewhere herein), the PDI of nanoparticles comprising the composition changes by less than or equal to about: 0.01, 0.05, 0.1, 0.2, 0.3, or ranges including and/or spanning the aforementioned values.

In some embodiments, the composition particle size remains consistent (a size change of less than or equal to about: 0%, 0.5%, 1%, 2%, 3%, 5%, or ranges including and/or spanning the aforementioned values) for a period of at least about 30 days when stored at room temperature, refrigeration, and up to 40° C. In some embodiments, the CBD concentration in the composition remains consistent (a loss of less than or equal to about: 0.5%, 1%, 2%, 3%, 5%, or ranges including and/or spanning the aforementioned values) for a period of at least about 30 days, 60 days, 90 days, or 120 days when stored at room temperature, refrigeration, and up to 40° C. In some embodiments, when stored at room temperature, refrigeration, and up to 40° C., the composition is stable (e.g., the particle size or CBD concentration in the nanoparticles remains consistent and/or has a change of less than or equal to about: 0.5%, 1%, 2%, 5%, or ranges including and/or spanning the aforementioned values) for a period of at least about: 2 weeks, 30 days, 2 months, 3 months, 6 months, 9 months, 1 year, or ranges including and/or spanning the aforementioned measures of time.

In some embodiments, the method of using the lipid-based particle composition and/or of treating a subject with the lipid-based particle composition includes administering to a subject in need of treatment (e.g., orally, topically, etc.) an effective amount of the composition. In some embodiments, the composition (e.g., delivery system) improves the stability of CBD after ingestion where the composition is exposed to the stomach and/or intestines in an aqueous environment with harsh pH conditions. In some embodiments, the bioavailability of CBD (e.g., in the blood of a subject) relative to the initial administered dose is greater than or equal to about: 10%, 20%, 50%, 75%, or ranges including and/or spanning the aforementioned values. In some embodiments, using the disclosed compositions, the oral bioavailability of CBD delivered (as measured using AUC) is higher using an embodiment disclosed herein relative to oral delivery of CBD oil alone. In some embodiments, the oral bioavailability is improved over CBD oil alone by greater than or equal to about: 10%, 50%, 75%, 100%, 200%, or ranges including and/or spanning the aforementioned values.

In some embodiments, compositions as described herein may be used to induce at least one effect, e.g. therapeutic effect, that may be associated with at least one cannabinoid (e.g., CBD), which is capable of inducing, enhancing, arresting or diminishing at least one effect, by way of treatment or prevention of unwanted conditions or diseases in a subject. As disclosed elsewhere herein, the at least one active agent may be selected amongst therapeutic agents, i.e. agents capable of inducing or modulating a therapeutic effect when administered in a therapeutically effective amount. In some embodiments, the phospholipid, non-phospholipid lipid, sterol, etc. by themselves do not induce or modulate a therapeutic effect but endow the pharmaceutical composition with a selected desired characteristic.

In some embodiments, the compositions disclosed herein (e.g., those including CBD) can be used in methods of treatment and can be administered to a subject having a condition to be treated. In some embodiments, the subject is treated by administering an effective amount of a composition (e.g., those including CBD) as disclosed herein to the subject. In some embodiments, the disease or condition to be treated via administration of a composition as disclosed herein may include one or more of pain, anxiety, seizures, malaise, etc. In some embodiments, the composition (e.g., those including CBD) is provided for use in treating a condition selected from pain associated disorders (as an analgesic), inflammatory disorders and conditions (as anti-inflammatory), apatite suppression or stimulation (as anoretic or stimulant), symptoms of vomiting and nausea (as antiemetic), intestine and bowl disorders, disorders and conditions associated with anxiety (as anxiolytic), disorders and conditions associated with psychosis (as antipsychotic), disorders and conditions associated with seizures and/or convulsions (as antiepileptic or antispasmodic), sleep disorders and conditions (as anti-insomniac), disorders and conditions which require treatment by immunosuppression, disorders and conditions associated with elevated blood glucose levels (as antidiabetic), disorders and conditions associated with nerve system degradation (as neuroprotectant), inflammatory skin disorders and conditions (such as psoriasis), disorders and conditions associated with artery blockage (as anti-ischemic), disorders and conditions associated with bacterial infections, disorders and conditions associated with fungal infections, proliferative disorders and conditions, disorders and conditions associated with inhibited bone growth, post trauma disorders, and others.

In some embodiments, the lipid-based particle composition (e.g., those including CBD, other phytocannabinoids, or other therapeutics as disclosed elsewhere herein) is provided for use in a method of treating a subject suffering from a condition selected from pain associated disorders, inflammatory disorders and conditions, apatite suppression or stimulation, symptoms of vomiting and nausea, intestine and bowl disorders, disorders and conditions associated with anxiety, disorders and conditions associated with psychosis, disorders and conditions associated with seizures and/or convulsions, sleep disorders and conditions, disorders and conditions which require treatment by immunosuppression, disorders and conditions associated with elevated blood glucose levels, disorders and conditions associated with nerve system degradation, inflammatory skin disorders and conditions, disorders and conditions associated with artery blockage, disorders and conditions associated with bacterial infections, disorders and conditions associated with fungal infections, proliferative disorders and conditions, and disorders and conditions associated with inhibited bone growth, post trauma disorders and others, the method comprising administering to the subject an effective amount of a composition of this disclosure.

In some embodiments, the lipid-based particle compositions (e.g., those including CBD or other phytocannabinoids) described herein may be used as such to induce at least one effect, e.g. therapeutic effect, or may be associated with at least one cannabinoid, which is capable of inducing, enhancing, arresting or diminishing at least one effect, by way of treatment or prevention of unwanted conditions or diseases in a subject. The at least one agent (substance, molecule, element, compound, entity, or a combination thereof) may be selected amongst therapeutic agents, i.e. agents capable of inducing or modulating a therapeutic effect when administered in a therapeutically effective amount, and non-therapeutic agents, i.e. which by themselves do not induce or modulate a therapeutic effect but which may endow the pharmaceutical composition with a selected desired characteristic.

In some embodiments, a lipid-based particle compositions as disclosed herein (e.g., a pharmaceutical composition comprising a therapeutic agent) may be selected to treat, prevent or ameliorate any pathology or condition. In some embodiments, administering of a therapeutic amount of the composition or system described herein, whether in a concentrate form or in a diluted formulation form, is effective to ameliorate undesired symptoms associated with a disease, to prevent the manifestation of such symptoms before they occur, to slow down the progression of the disease, slow down the deterioration of symptoms, to enhance the onset of remission period, slow down the irreversible damage caused in the progressive chronic stage of the disease, to delay the onset of said progressive stage, to lessen the severity or cure the disease, to improve survival rate or more rapid recovery, or to prevent the disease from occurring or a combination of two or more of the above.

Surprisingly and advantageously, several embodiments disclosed herein do not require several ingredients typically used to prepare liposomes and/or nanoparticle formulations. In some embodiments, the lipid-based particle compositions disclosed herein lack, contain less than 2%, and/or less than about 0.5% of one or more of lecithin surfactants, hyaluronic acid, Alcolec S, Alcolec BS, Alcolec XTRA-A, polysorbates (such as Polysorbate 80 and Polysorbate 20), monoglycerides, diglycerides, glyceryl oleate, polaxamers, terpenes, sodium alginate, polyvinylpyrrolidone, L-alginate, chondroitin, poly gamma glutamic acid, gelatin, chitosan, corn starch, polyoxyl 40-hydroxy castor oil, Tween 20, Span 80, or the salts of any of thereof. In some embodiments, the lipid-based particle compositions disclosed herein lack, contain less than 2%, and/or less than about 0.5% of a surfactant. In some embodiments, the CBD lipid-based particle compositions disclosed herein lack, contain less than 2%, and/or less than about 0.5% of one or more of THCa, 9-THC, 8-THC, CBDa, CBC, CBG, CBN, THCV, and/or CBGa. In some embodiments, the lipid-based particle compositions lack unhydrogenated phospholipids. In some embodiments, the lipid-based particle compositions lack hydrogenated phospholipids. In some embodiments, the lipid-based particle compositions comprise one or more unhydrogenated or hydrogenated phospholipids. In some embodiments, the lipid-based particle compositions disclosed herein lack, contain less than 2%, and/or less than about 0.5% of one or more of a buffering agent, a polymeric stabilizing agent, or sodium hydroxide.

In some embodiments, the lipid-based particle compositions disclosed herein lack a nanoparticle structure wherein the structure comprises an outer single layer membrane of essential phospholipids that encapsulates liquid lipids and cannabinoids. As used herein, essential phospholipids are extracts of characteristic fatty acid lipid-based particle composition of the phospholipids distinguished by their particular high content of polyunsaturated fatty acids, predominantly linoleic acid (approx. 70%), linolenic acid and oleic acid and with a high content exceeding 75% of (3-sn-phosphatidyl) choline. Beside phosphatidylcholine molecules, the essential phospholipid fraction includes phosphatidylethanolamine, phosphatidylinositol and other lipids. In some embodiments, the lipid-based particle compositions disclosed herein lack nonnatural ingredients. In some embodiments, the lipid-based particle compositions disclosed are synthetic and not found in nature.

In some embodiments, the lipid-based particle compositions disclosed herein lack, contain less than 2%, and/or less than about 0.5% of one or more organic bases (which may include, but are not limited to: butyl hydroxyl anisole (BHA), butyl hydroxyl toluene (BHT) and sodium ascorbate). In some embodiments, the lipid-based particle compositions disclosed herein lack, contain less than 2%, and/or less than about 0.5% of whey protein isolate. In some embodiments, the lipid-based particle compositions disclosed herein lack, contain less than 2%, and/or less than about 0.5% of ticamulsion 3020, purity gum, gum Arabic, and/or a modified gum Arabic. In some embodiments, the lipid-based particle compositions disclosed herein lack, contain less than 2%, and/or less than about 0.5% one or more of fatty acids, triglycerides triacylglycerols, acylglycerols, fats, waxes, sphingolipids, glycerides, sterides, cerides, glycolipids, sulfolipids, lipoproteins, chylomicrons and the derivatives of these lipids. In some embodiments, the lipid-based particle compositions disclosed herein lack, contain less than 2%, and/or less than about 0.5% of a surfactant. In some embodiments, the lipid-based particle compositions disclosed herein lack, contain less than 2%, and/or less than about 0.5% of one or more of polyglycolized glycerides and polyoxyethylene glycerides of medium to long chain mono-, di-, and triglycerides, such as: almond oil PEG-6 esters, almond oil PEG-60 esters, apricot kernel oil PEG-6 esters (Labrafil® M1944CS), caprylic/capric triglycerides PEG-4 esters (Labrafac® Hydro WL 1219), caprylic/capric triglycerides PEG-4 complex (Labrafac® Hydrophile), caprylic/capric glycerides PEG-6 esters (Softigen® 767), caprylic/capric glycerides PEG-8 esters (Labrasol®), castor oil PEG-50 esters, hydrogenated castor oil PEG-5 esters, hydrogenated castor oil PEG-7 esters, 9 hydrogenated castor oil PEG-9 esters, corn oil PEG-6 esters (Labrafil® M 2125 CS), corn oil PEG-8 esters (Labrafil® WL 2609 BS), corn glycerides PEG-60 esters, olive oil PEG-6 esters (Labrafil® M1980 CS), hydrogenated palm/palm kernel oil PEG-6 esters (Labrafil® M 2130 BS), hydrogenated palm/palm kernel oil PEG-6 esters with palm kernel oil, PEG-6, palm oil (Labrafil® M 2130 CS), palm kernel oil PEG-40 esters, peanut oil PEG-6 esters (Labrafil® M 1969 CS), glyceryl laurate/PEG-32 laurate (Gelucire® 44/14), glyceryl laurate glyccry I/PEG 20 laurate, glyceryl laurate glyceryl/PEG 32 laurate, glyceryl, laurate glyceryl/PEG 40 laurate, glyceryl oleate/PEG-20 glyceryl, glyceryl oleate/PEG-30 oleate, glyceryl palmitostearate/PEG-32 palmitostearate (Gelucire® 50/13), glyceryl stearate/PEG stearate, glyceryl stearate/PEG-32 stearate (Gelucire® 53/10), saturated polyglycolized glycerides (Gelucire® 37/02 and Gelucire® 50/02), triisostearin PEG-6 esters (i.e. Labrafil® Isostearique), triolein PEG-6 esters, trioleate PEG-25 esters, polyoxyl 35 castor oil (Cremophor® EL or Kolliphor® EL), polyoxyl 40 hydrogenated castor oil (Cremophor® RH 40 or Kolliphor® RH40), polyoxyl 60 hydrogenated castor oil (Cremophor® RH60), polyglycolized derivatives and polyoxyethylene esters or ethers derivatives of medium to long chain fatty acids, propylene glycol esters of medium to long chain fatty acids, which can be used including caprylate/caprate diglycerides, glyceryl monooleate, glyceryl ricinoleate, glyceryl laurate, glyceryl dilaurate, glyceryl dioleate, glyceryl mono/dioleate, polyglyceryl-10 trioleate, poly glyceryl-10 laurate, polyglyceryl-10 oleate, and poly glyceryl-10 mono dioleate, propylene glycol caprylate/caprate (Labrafac® PC), propylene glycol dicaprylate/dicaprate (Miglyol® 840), propylene glycol monolaurate, propylene glycol ricinoleate, propylene glycol monooleate, propylene glycol dicaprylate/dicaprate, propylene glycol dioctanoate, sucrose esters surfactants such as sucrose stearate, sucrose distearate, sucrose palmitate, sucrose oleate, and combinations thereof.

Some embodiments also encompass methods for making (as disclosed elsewhere herein) and for administering the disclosed compositions. Multiple techniques of administering the lipid-based particle compositions as disclosed herein exist including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections. In some embodiments, administration is performed through oral pathways, which administration includes administration in an emulsion, capsule, tablet, film, chewing gum, suppository, granule, pellet, spray, syrup, or other such forms. As further examples of such modes of administration and as further disclosure of modes of administration, disclosed herein are various methods for administration of the disclosed compositions including modes of administration through intraocular, intranasal, and intraauricular pathways. In some embodiments, where a topical is provided, topical permeation enhancers may be included and may be selected from, but not inclusive of, the following: dimethyl sulfoxide, dimethyl sulfone, ethanol, propylene glycol, dimethyl isosorbide, polyvinyl alcohol, Capryol™ 90, Labrafil M1944 CS, Labrasol, Labrasol ALF, Lauroglycol™90, Transcutol HP, Capmul S12L, Campul PG-23 EP/NF, Campul PG-8 NF. The topical may include one or more of Lipoid's Skin Lipid Matrix 2026 technology, lipid/oil based ingredients or oil soluble ingredients, and includes Captex 170 EP as a skin permeation enhancer, argan oil, menthol, arnica oil, camphor, grapefruit seed oil, For example, dimethyl sulfoxide, dimethyl isosorbide, topical analgesics such as lidocaine, wintergreen oil, and terpenes such as guaiacol. In some embodiments, any one or more of these ingredients is present in the topical composition at a dry wt % of equal to or less than about: 5%, 10%, 15%, 20%, 30%, 40%, 50%, 60%, or ranges including and/or spanning the aforementioned values. In some embodiments, any one or more of these ingredients is present in the topical at a wet wt % of equal to or at least about: 2.5%, 5%, 7.5%, 10%, 12.5%, 15%, 20%, 30%, or ranges including and/or spanning the aforementioned values.

In some embodiments, the lipid-based particle compositions disclosed herein can be in admixture with a suitable carrier, diluent, or excipient such as sterile water, physiological saline, glucose, or the like, and can contain auxiliary substances such as wetting or emulsifying agents, pH buffering agents, gelling or viscosity enhancing additives, preservatives, flavoring agents, colors, and the like, depending upon the route of administration and the preparation desired. See, e.g., "Remington: The Science and Practice of Pharmacy", Lippincott Williams & Wilkins; 20th edition (Jun. 1, 2003) and "Remington's Pharmaceutical Sciences," Mack Pub. Co.; $18^{th}$ and $19^{th}$ editions (December 1985, and June 1990, respectively). In some embodiments, these additional agents are not added. Such preparations can include liposomes, microemulsions, micelles, and/or unilamellar or multilamellar vesicles.

For oral administration, the pharmaceutical lipid-based particle compositions can be provided as a tablet, aqueous or oil suspension, dispersible powder or granule (as a food additive, drink additive, etc.), emulsion, hard or soft capsule, syrup or elixir. Compositions intended for oral use can include one or more of the following agents: sweeteners, flavoring agents, coloring agents and preservatives. Formulations for oral use can also be provided as gelatin capsules. In some embodiments, a powder composition as disclosed herein is added to the gelatin capsule. In some embodiments, the active ingredient(s) in the nanoparticle compositions disclosed herein are mixed with an inert solid diluent, such as calcium carbonate, calcium phosphate, or kaolin, or as soft gelatin capsules. In soft capsules, the active compounds can be dissolved or suspended in suitable liquids, such as water. Stabilizers and microspheres formulated for oral administration can also be used. Capsules can include push-fit capsules made of gelatin, as well as soft, sealed capsules made of gelatin and a plasticizer, such as glycerol or sorbitol.

In capsule formulations, trehalose can be added. In some embodiments, trehalose is present in the lipid-based particle composition at a dry wt % of equal to or less than about: 5%, 10%, 15%, 20%, 30%, 40%, 50%, 60%, or ranges including and/or spanning the aforementioned values. In some embodiments, the trehalose is present in the composition at a wet wt % of equal to or at least about: 2.5%, 5%, 7.5%, 10%, 12.5%, 15%, 20%, 30%, or ranges including and/or spanning the aforementioned values.

As noted elsewhere herein, in some embodiments, the lipid-based particle composition lacks terpenes (e.g., as impurities or additives). However, in other embodiments, one or more terpenes may be added to prepare the nanoparticle composition. In some embodiments, the one or more terpenes includes one or more of alpha fenchone, alpha terpinene, alpha terpineol, beta caryophyllene, alpha pinene, beta pinene, bisabolene, bisabolol, borneol, eucalyptol, gamma terpinene, guaiacol, humulene, linalool, myrcene, para cymene, phytol, and/or terpinolene. In some embodiments, the one or more terpenes, collectively or individually, are present in the aqueous composition at a concentration of less than or equal to about: 400 mg/ml, 300 mg/ml, 200 mg/ml, 150 mg/ml, 100 mg/ml, 75 mg/ml, 50 mg/ml, 25 mg/ml, or ranges including and/or spanning the aforementioned values. In some embodiments, the one or more terpenes (collectively or individually) are present in the composition at a dry wt % of equal to or less than about: 5%, 10%, 15%, 20%, 30%, 40%, 50%, 60%, or ranges including and/or spanning the aforementioned values. In some embodiments, the one or more terpenes (collectively or individually) are present in the composition at a wet wt % of equal to or less than about: 2.5%, 5%, 7.5%, 10%, 12.5%, 15%, 20%, 30%, 40%, or ranges including and/or spanning the aforementioned values.

Dry powder formulations or liquid embodiments may also be used in a variety of consumer products. For example, in some embodiments, dry powders can be added (e.g., scooped, from a packet, squirted from a dispenser, etc.) into any consumer product. In some embodiments, liquid formulations can be added measured and poured into any consumer product. In some embodiments, the consumer product can include one or more alcoholic beverages, milks (dairy, but also nuts "milks" such as almond juice, etc.), coffee, sodas, tea, fermented beverages, wines, nutritional supplements, smoothies, simple water, sports drinks, sparkling water, or the like. In some embodiments, the consumer product can include one or more eye drops, mouth wash, lotions/creams/serums, lip balms, hair care products, deodorant, nasal solutions, enema solutions, liquid soaps, solid soaps, or the like. In some embodiments, the consumer product can include one or more food products. In some embodiments, the consumer product can include desserts. In some embodiments, the consumer product can include single serving products of multi-serving products (e.g., family size). In some embodiments, the consumer product can include one or more dried products (e.g., flour, coffee creamer, protein shakes, nutritional supplements, etc.). In some embodiments, these dried products can be configured to be reconstituted for use. In some embodiments, the consumer product can include one or more the dried product can be added to other dietary supplements (e.g., multivitamins, gummies, etc.).

Several illustrative embodiments of compositions and methods have been disclosed. Although this disclosure has been described in terms of certain illustrative embodiments and uses, other embodiments and other uses, including embodiments and uses which do not provide all of the features and advantages set forth herein, are also within the scope of this disclosure. Components, elements, features, acts, or steps can be arranged or performed differently than described and components, elements, features, acts, or steps can be combined, merged, added, or left out in various embodiments. All possible combinations and subcombinations of elements and components described herein are intended to be included in this disclosure. No single feature or group of features is necessary or indispensable.

Certain features that are described in this disclosure in the context of separate implementations can also be implemented in combination in a single implementation. Conversely, various features that are described in the context of a single implementation also can be implemented in multiple implementations separately or in any suitable subcombination. Moreover, although features may be described above as acting in certain combinations, one or more features from a claimed combination can in some cases be excised from the combination, and the combination may be claimed as a subcombination or variation of a subcombination.

Any portion of any of the steps, processes, structures, and/or devices disclosed or illustrated in one embodiment, flowchart, or example in this disclosure can be combined or used with (or instead of) any other portion of any of the steps, processes, structures, and/or devices disclosed or illustrated in a different embodiment, flowchart, or example. The embodiments and examples described herein are not intended to be discrete and separate from each other. Combinations, variations, and other implementations of the disclosed features are within the scope of this disclosure.

The terms "approximately," "about," and "substantially" as used herein represent an amount close to the stated amount that still performs a desired function or achieves a desired result. For example, in some embodiments, as the context may dictate, the terms "approximately", "about", and "substantially" may refer to an amount that is within less than or equal to 10% of the stated amount. The term "generally" as used herein represents a value, amount, or characteristic that predominantly includes or tends toward a particular value, amount, or characteristic.

Conditional language used herein, such as, among others, "can," "could," "might," "may," "e.g.," and the like, unless specifically stated otherwise or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Further, while illustrative embodiments have been described, any embodiments having equivalent elements, modifications, omissions, and/or combinations are also within the scope of this disclosure. Moreover, although certain aspects, advantages, and novel features are described herein, not necessarily all such advantages may be achieved in accordance with any particular embodiment. For example, some embodiments within the scope of this disclosure achieve one advantage, or a group of advantages, as taught herein without necessarily achieving other advantages taught or suggested herein. Further, some embodiments may achieve different advantages than those taught or suggested herein.

Enumerated Embodiments

The following are provided for the illustration of certain embodiments of the invention.

1. A nanoparticle composition, comprising:
a nanoparticle comprising:
cannabidiol (CBD) that is of sufficient purity that it exists in a solid and/or powdered state prior to formulation in the nanoparticle composition;
a phospholipid comprising:
cholesterol; and
a medium chain triglyceride; and
water;
wherein the nanoparticles have an average size ranging from about 75 nm to about 500 nm; and
wherein, upon storage for a period of one month, the average size of the nanoparticles changes by less than about 20%.

2. The composition of embodiment 1, wherein the composition is in the form of liposomes and/or an oil-in-water nano-emulsion.

3. The composition of embodiment 1 or 2, wherein an appreciable amount of the nanoparticle composition does not settle and/or separate from the water upon standing for a period of at least about 12 hours.

4. The composition of any one of embodiments 1 to 3, wherein the composition is configured such that when concentrated to dryness to afford a powder formulation of nanoparticles, the nanoparticle powder can be reconstituted to provide the nanoparticle composition.

5. The composition of any one of embodiments 1 to 4, wherein the CBD is present in an amount of less than or equal to about 25 mg/ml.

6. The composition of any one of embodiments 1 to 5, wherein the phosphatidylcholine is present in an amount of less than or equal to about 100 mg/ml.

7. The composition of any one of embodiments 1 to 6, wherein the cholesterol is present in an amount of less than or equal to about 25 mg/ml.

8. The composition of any one of embodiments 1 to 7, wherein the lipid is present in an amount of less than or equal to about 100 mg/ml.

9. The composition of any one of embodiments 1 to 8, wherein the lipid comprises hemp oil.

10. The composition of any one of embodiments 1 to 9, further comprising a preservative.

11. The composition of embodiment 10, wherein the preservative comprises one or more of malic acid, citric acid, potassium sorbate, sodium benzoate, and Vitamin E.

12. The composition of embodiment 11, wherein the malic acid is present in an amount of less than or equal to about 0.85 mg/ml.

13. The composition of embodiment 11, wherein the citric acid is present in an amount of less than or equal to about 0.85 mg/ml.

14. The composition of embodiment 11, wherein the potassium sorbate is present in an amount of less than or equal to about 1 mg/ml.

15. The composition of embodiment 11, wherein the sodium benzoate is present in an amount of less than or equal to about 1 mg/ml.

16. The composition of any one of embodiment 1 to 15, further comprising a flavoring agent.

17. A nanoparticle composition, comprising:
a nanoparticle comprising:
a phospholipid;
a triglyceride;
a sterol; and
a phytocannabinoid; and
water;
wherein an appreciable amount of the nanoparticle composition does not settle and/or separate from the water upon standing for a period of at least about 12 hours.

18. The composition of embodiment 17, wherein the phospholipid is selected from the group consisting of phosphatidic acid, phosphatidylethanolamine, phosphatidylcholine, phosphatidylserine, phosphatidylinositol, phosphatidylinositol phosphate, phosphatidylinositol bisphosphate, and phosphatidylinositol trisphosphate.

19. The composition of embodiment 17 or 18, wherein the triglyceride is a medium chain triglyceride.

20. The composition of embodiment 19, wherein the medium chain triglyceride comprises one or more of caprioc acid, octanoic acid, capric acid, and/or lauric acid.

21. The composition of any one of embodiments 17 to 20, wherein the sterol is cholesterol.

22. The composition of any one of embodiments 17 to 21, wherein the phytocannabinoid is cannabidiol.

23. A method of treating a patient in need of treatment comprising administering an effective amount of the composition of any one of embodiments 1 to 22 to the patient.

24. A method of manufacturing a nanoparticle composition of a phytocannabinoid, comprising:
mixing the phytocannabinoid and one or more phospholipids to provide a solution; and
passing the solution through a microfluidizer.

25. The method of embodiment 24, further comprising adding one or more sterols to the solution.

26. The method of embodiment 24 or 25, further comprising adding one or more lipids to the solution.

27. A method of manufacturing a nanoparticle composition of a phytocannabinoid, comprising:
mixing the phytocannabinoid and one or more phospholipids to provide a solution;
drying the solution to provide a substantially solid product;
constituting the product in water to provide a reconstituted solution; and
passing the reconstituted solution through a microfluidizer.

28. The method of embodiment 27, further comprising adding one or more sterols to the solution.

29. The method of embodiment 27 or 28, further comprising adding one or more lipids to the solution.

30. A lipid-based particle composition, comprising:
a nanoparticle comprising:
cannabidiol (CBD) that is of sufficient purity that it exists in a solid and/or powdered state prior to formulation in the nanoparticle composition at a weight percent in the composition ranging from 1% to 10%;
a phosphatidylcholine at a weight percent in the composition ranging from 2.5% to 15%;
a sterol at a weight percent in the composition ranging from 0.5% to 5%; and
a medium chain triglyceride at a weight percent in the composition ranging from 2.5% to 15%; and
water at a weight percent in the composition ranging from 60% to about 80%;
wherein the nanoparticles have an average size ranging from about 75 nm to about 175 nm; and
wherein, upon storage for a period of one month, the average size of the nanoparticles changes by less than about 20%.

31. The lipid-based particle composition of embodiment 30, wherein the composition is in the form of liposomes and/or an oil-in-water nano-emulsion.

32. The lipid-based particle composition of embodiment 30 or 31, wherein an appreciable amount of the nanoparticle composition does not settle and/or separate from the water upon standing for a period of at least about 12 hours.

33. The lipid-based particle composition of any one of embodiments 30 to 32, wherein the composition is configured such that when concentrated to dryness to afford a powder formulation of nanoparticles, the nanoparticle powder can be reconstituted to provide the nanoparticle composition.

34. The lipid-based particle composition of any one of embodiments 30 to 33, wherein the composition has a Tmax for CBD of less than 4.5 hours.

35. The lipid-based particle composition of any one of embodiments 30 to 34, wherein, upon storage for a period of one month, the average size of the nanoparticles changes by less than about 20%.

36. The lipid-based particle composition of any one of embodiments 30 to 35, wherein the polydispersity of the nanoparticles in the composition is less than or equal to 0.15.

37. The lipid-based particle composition of any one of embodiments 30 to 36, wherein upon 90 days of storage at 25° C. and 60% relative humidity, the polydispersity of the nanoparticles changes by less than or equal to 10%.

38. The lipid-based particle composition of any one of embodiments 30 to 37, wherein upon 90 days of storage at 25° C. and 60% relative humidity, the polydispersity of the nanoparticles changes by less than or equal to 0.1.

39. The lipid-based particle composition of any one of embodiments 30 to 38, wherein composition has a shelf life of greater than 18 months at 25° C. and 60% relative humidity.

40. The lipid-based particle composition of any one of embodiments 30 to 39, upon 90 days of storage at 25° C. and 60% relative humidity, the D90 of the nanoparticles changes less than or equal to 10%.

41. The lipid-based particle composition of any one of embodiments 30 to 40, wherein the composition has a concentration max (Cmax) of 80 ng/ml after an oral dose of 15 mg/kg.

42. A lipid-based particle composition, comprising:
a nanoparticle comprising:
cannabidiol (CBD) that is of sufficient purity that it exists in a solid and/or powdered state prior to formulation in the nanoparticle composition at a weight percent in the composition ranging from 5% to 15%;
a phosphatidylcholine at a weight percent in the composition ranging from 35% to 60%;
a sterol at a weight percent in the composition ranging from 2.5% to 10%; and
a medium chain triglyceride at a weight percent in the composition ranging from 35% to 50%;
wherein the composition has a Cmax of 80 ng/ml after an oral dose of 15 mg/kg.

43. The lipid-based particle composition of embodiment 42, wherein the lipid-based particle composition is provided as a dry powder.

44. The lipid-based particle of embodiment 43, wherein the powder is configured to be reconstituted in water to provide an aqueous solution.

45. The lipid-based particle of embodiment 43 or 44, wherein, upon reconstitution, nanoparticles within the aqueous solution have an average size ranging from about 75 nm to about 175 nm.

46. The lipid-based particle composition of any one of embodiments 30 to 45, further comprising a preservative.

47. The lipid-based particle composition of embodiment 46, wherein the preservative comprises one or more of malic acid, citric acid, potassium sorbate, sodium benzoate, and Vitamin E.

48. The lipid-based particle composition of any one of embodiments 30 to 47, wherein the sterol is cholesterol.

49. The lipid-based particle composition of any one of embodiment 30 to 48, further comprising a flavoring agent.

50. A method of treating a patient in need of treatment comprising administering an effective amount of the lipid-based particle composition of any one of embodiments 30 to 49 to the patient.

51. A method of manufacturing a nanoparticle composition of a phytocannabinoid, comprising:
  providing the phytocannabinoid;
  providing phosphatidylcholine;
  providing a medium chain triglyceride;
  mixing the medium chain triglyceride, phosphatidylcholine, and phytocannabinoid to provide a solution; and
  passing the solution through a microfluidizer to provide a lipid-based particle composition.

52. The method of embodiment 51, further comprising adding one or more sterols to the solution.

53. The method of embodiment 51 or 52, further comprising adding water to the solution.

EXAMPLES

The following examples are given for the purpose of illustrating various embodiments of the disclosure and are not meant to limit the present disclosure in any fashion. One skilled in the art will appreciate readily that the present disclosure is well adapted to carry out the objects and obtain the ends and advantages mentioned, as well as those objects, ends and advantages inherent herein. Changes therein and other uses which are encompassed within the spirit of the disclosure as defined by the scope of the claims will occur to those skilled in the art. Formulations were prepared using ingredient profiles and techniques as disclosed herein. The impact of several quality attributes of the formulation on particle size, CBD concentration, and product stability were determined. Such product attributes included CBD to lipid ratio and the preservative system and overall impact of pH. The dissolution and stability of the product was measured in simulated gastric and intestinal fluids. Additionally, the oral pharmacokinetics of embodiments disclosed herein were measured in a mini-pig model and compared to two oil-based commercial products. The physical and chemical stability of embodiments disclosed herein were determined under several storage conditions.

Example 1: Preparation of an Embodiment of the Composition

Materials and Methods

Unless otherwise noted, the ingredients used herein were obtained from the following vendors: Sunflower derived phosphatidylcholine and medium chain triglycerides were purchased from American Lecithin Company (a Lipoid Company listed as "MCT"), potassium sorbate, peppermint oil, vitamin E, malic acid, and cholesterol were purchased from Spectrum Chemicals, CBD isolate was purchased from Botanical & Bioscience Laboratories, Luo Han Guo (monk fruit) extract was purchased from GLG Life Tech Corporation, water for injection was purchased from Rocky Mountain Biologicals, and citric acid monohydrate and sodium benzoate were purchased from JT Baker. The CBD isolate used comprised not more than 0.3% THC by weight per weight (w/w). The phosphatidylcholine was H 100-3 grade including over 96.3% or 99.9% phosphatidylcholine (hydrogenated). The phosphatidyl choline and less than 1.1% lysophosphatidylcholine and less than 2.0% triglycerides. This is a highly purity phosphatidylcholine (over 96% pure phosphatidylcholine (hydrogenated)) which is, to the inventor's knowledge, not used in current CBD products.

Particle size and zeta potential of liquid was measured on a Malvern ZS90 Zetasizer (Malvern, UK). The liquid product was diluted at least 50 times in purified water and the equivalent of 1 mg of CBD in a powder form was dissolved in 1 mL of purified water for measurements. Products were measured in low-volume, disposable cuvettes and zeta cassettes. Cannabinoids and terpenes concentrations, related substances and identity (retention time) were measure by high-pressure liquid chromatography (HPLC) at 374 Labs (Reno, Nev.). Residual solvents and pesticides were measured by gas chromatography (GC), and heavy metals by inductive coupled plasma-optical emission spectrometry (ICP-oES) at 374 Labs. Rapid preservative effectiveness testing was determined by a reduction in colony forming units (CFU) of test microorganisms at Microchem Laboratory (Round Rock, Tex.). Testing confirmed that the compositions were resistant to bacterial growth (by measuring colony forming units (CFUs) per volume in a given amount of time.

Manufacturing Process: CBD lipid nanoparticles in this example were prepared using a solvent-based method with high pressure homogenization. To prepare the nanoparticle composition lipophilic ingredients (solid CBD comprising not more than 0.3% THC, medium chain triglyceride, cholesterol, phosphatidylcholine, Vitamin E, oil soluble flavoring, etc.) were accurately weighed onto a weigh boat and then transferred to a 20 liter, glass, round-bottom flask. To the lipophilic ingredients, approximately 1.3 to 1.5 times the weight of the lipophilic ingredients was added of 100% (200 proof) ethanol. The lipophilic ingredients were dissolved in the ethanol before proceeding. The 20 liter round bottom flask was transferred to a Hei-VAP Industrial Rotary Evaporator (Heidolph Corporation) and the ethanol was removed by evaporation under reduced pressure, elevated temperature, and vessel rotation. When the ethanol was removed, a film of lipid remained on the glass vessel walls. The lipid film was blanketed with nitrogen glass and left at room temperature overnight.

All water-soluble formulation ingredients (water soluble flavoring, sodium benzoate, potassium sorbate, citric acid monohydrate, malic acid, etc.) were dissolved into water for injection at the specified concentrations (below). Aqueous solutions were heated and filtered prior to further use. An appropriate amount of aqueous solution was transferred to the glass vessel containing the dried lipid ingredients. The glass vessel was transferred to a heating mantel and warmed with constant stirring from an overhead mixer. Mixing was continued until a homogenous slurry of lipids in water was formed. The full volume of lipid slurry was processed through a microfluidizer (Microfluidics Corporation) 0 to 10 times at a processing pressure of 10,000-30,000 PSI. Alternatively, the volume of lipid slurry can be processed at a pressure of 10,000-30,000 PSI such that the material is recirculated back into the unprocessed volume for a period of time until the desired particle size characteristics are achieved. The resulting lipid nanoparticle solution was cooled with continuous stirring for 12-24 hours before characterizing and fill-finish. Flavoring in oil form was introduced into the dried lipid film prior to introduction of the aqueous solution. Water soluble flavoring is dissolved into the water for injection prior to introduction into the lipid film.

Four batches of approximately 10 liters of CBD isolate containing lipid nanoparticles each were prepared in a cGMP facility according to the Manufacturing Process described above. The ingredient composition of each batch is described in the table below.

TABLE 1

| Ingredient | Batches 1 and 3 | Batches 2 and 4 |
| --- | --- | --- |
| Oil Soluble Flavoring | 0.12% (w/w) | 0.00% (w/w) |
| Vitamin E Oil | 0.05% (w/w) | 0.05% (w/w) |
| Sodium Benzoate | 0.10% (w/w) | 0.10% (w/w) |
| Potassium Sorbate | 0.10% (w/w) | 0.10% (w/w) |
| Citric Acid Monohydrate | 0.10% (w/w) | 0.10% (w/w) |
| Malic Acid | 0.01% (w/w) | 0.01% (w/w) |
| Water Soluble Flavoring | 0.09% (w/w) | 0.09% (w/w) |
| Sunflower Phosphatidylcholine | 10.08% (w/w) | 10.08% (w/w) |
| Medium Chain Triglyceride | 9.67% (v/w) | 9.67% (v/w) |
| CBD Isolate | 2.01% (w/w) | 2.01% (w/w) |
| Cholesterol | 1.01% (w/w) | 1.01% (w/w) |
| Ethanol | <0.10% (w/w) | <0.10% (w/w) |
| Water for Injection | 76.65% (v/w) | 76.79% (v/w) |

Example 2: Stability Testing

This example discloses stability testing and shelf-life data for some embodiments as prepared in Example 1. Upon cooling, the batches prepared in Example 1 were filled into 20 mL amber vials with a child-proof cap affixed with a required removal torque of 7.0 to 9.0 pound force inch. Sealed bottles were stored at 2-8° C., 25° C./60% Relative Humidity, 40° C./75% relative humidity, or 50° C. and uncontrolled humidity. At a minimum, samples were pulled for characterization on months 0, 1, 2, 3, 6, and 11. Characterization included particle size analysis by dynamic light scattering and CBD concentration by UPLC. Results are show in FIGS. 3 and 4.

Figure 3:
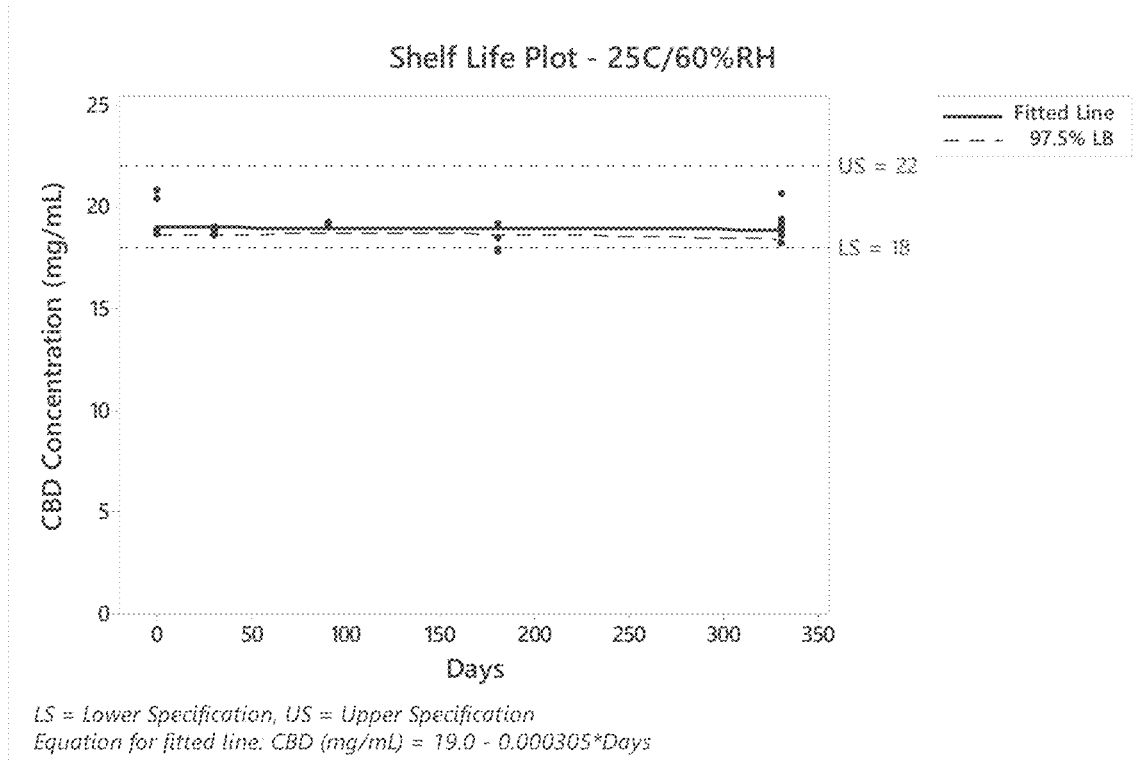
FIG. 3 depicts the CBD concentration in an embodiment of the disclosed lipid-based particle compositions over time when stored at 25° C./60% relative humidity.
Figure 4:
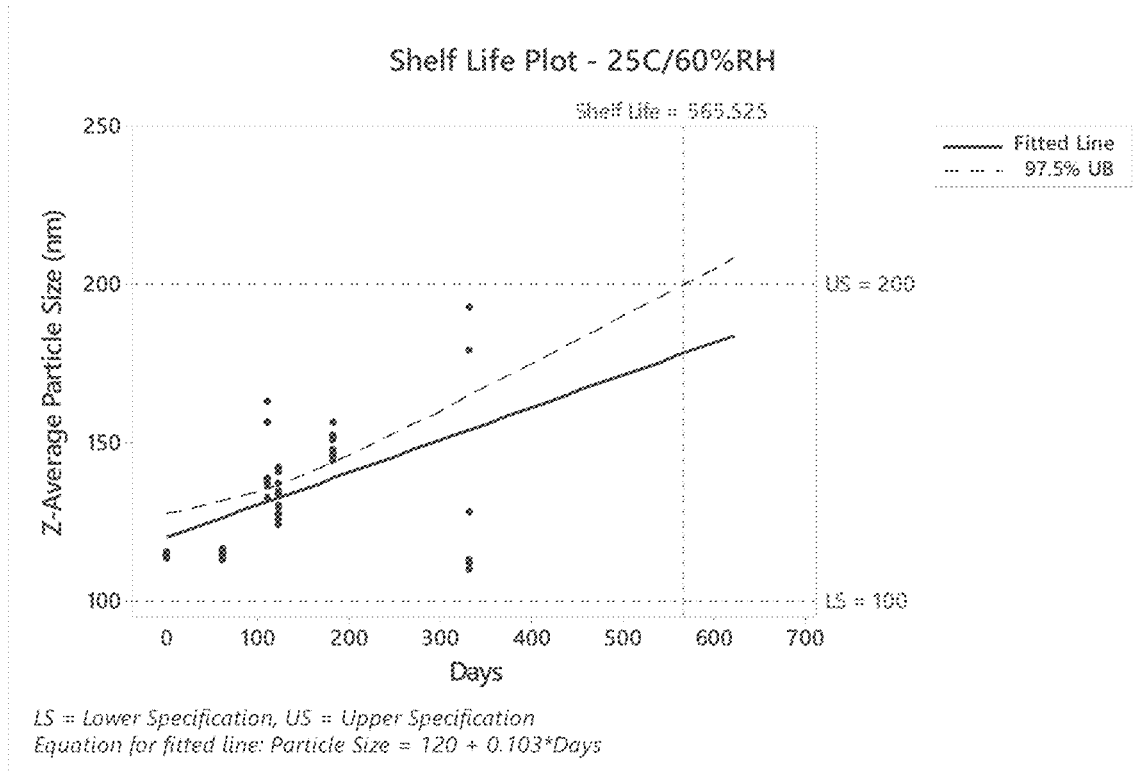
FIG. 4 depicts the particle size of an embodiment of the disclosed lipid-based particle compositions over time when stored at 25° C./60% relative humidity.

Shelf-life plots were created in MiniTab Version 17.0 using real-time data only (25° C./60% Relative Humidity). The shelf-life is the period of time in which there is 95% confidence that at least 50% of the response (CBD concentration or particle size) is within the specification limit. Shown in FIG. 3 is the shelf life plot of 4 batches of product as a function of CBD concentration. Over the 11 months where CBD concentration was determined, the response slope of the regression line is not significantly different from zero and no shelf-life can be predicted until a negative slope (ie degradation) appears in the data set. FIG. 4 shows the shelf life plot of 4 batches of product as a function of lipid nanoparticle Z-Average size in nanometers. An upper specification limit of 200 nm was chosen and shelf-life of 565.5 days or approximately 19 months is estimated. Taken together, formulation quality attributes of CBD concentration and particle size remain within the product specification for an estimated 19 months, indicating the product has a shelf-life of 19 months.

Example 3: Imaging of Nanoparticles

Figure 5:
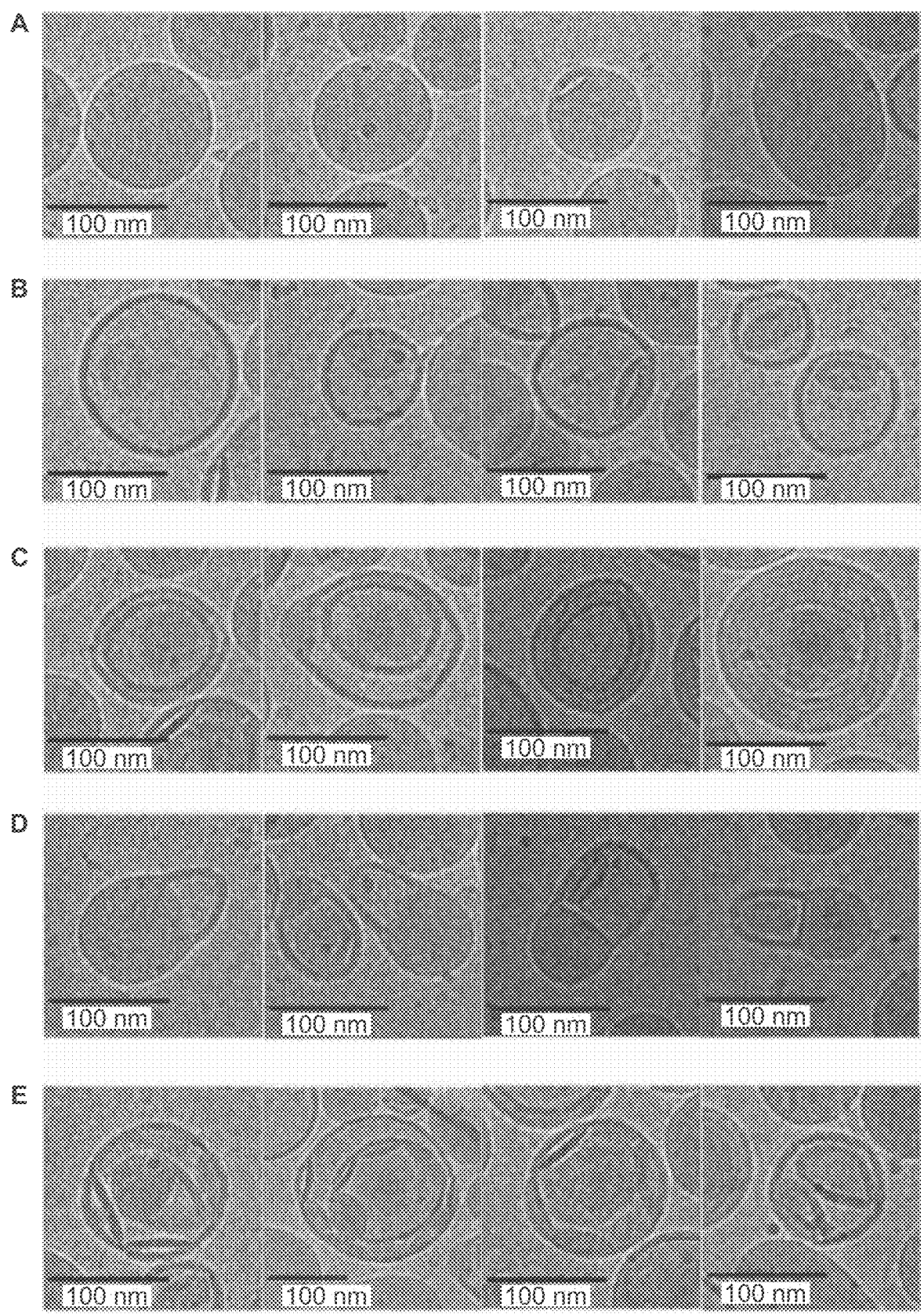
FIGS. 5A-5E depict representative images of some embodiments of lipid nanoparticles as disclosed herein.

This example discloses representative images of lipid nanoparticles prepared as previously described in Example 1. A sample consistent with the ingredient composition outlined in Batch 1 and 3 was diluted 10 times with water. Three microliters was placed on a thin copper grid (Cu-200CN, Pacific Grid-Tech) that was previously glow-discharged. For preparation of the grid, the sample was loaded into the freezing chamber at low temperature (0-5° C.) under humidity control (100%). After blotting for 2 seconds with filter paper, the specimen was rapidly frozen with cryogen, liquid ethane cooled by liquid nitrogen. The prepared dried was mounted on 200 kV FEI Talos C200C electron microscope. Microscope images were collected at 45K magnification. Example images are shown in FIG. 5.

Lipid nanoparticles prepared using the methods of Example 1 afforded several sub-types of particles. Shown in FIG. 5 Panel A are characteristic emulsion style particles, FIG. 5 Panel B shows lipid nanoparticles containing unilamellar vesicles, also known as small unilamellar vesicles, FIG. 5 Panel C shows particles with multilamellar vesicles, FIG. 5 Panel D shows combined emulsion and unilamellar vesicles, and FIG. 5 Panel D shows irregular particles with lamellar structures and bridges, as well as partial emulsion particles.

It is believed that these sub-types of particles can be controlled via changes in the ingredients and processing parameters, or combinations of both. As the concentration of MCT decreases to 0% the proportion of emulsion lipid nanoparticles will decrease and the vesicle sub-type of particles will increase. This is not only true in the case of MCT, but possibly includes other oils that are a liquid at room temperature or is a liquid at room temperature when mixed with other lipids. Replacing the liquid oil at room temperature with an oil that is both solid at room temperature and waxy makes a solid lipid nanoparticle product. This type of particle will appear similar to the emulsion lipid particle because both have a dense core. Decreasing the liquid oil and/or increasing the phosphatidylcholine will likely increase the proportion of particles that are mixed or irregular. Decreasing the liquid oil and decreasing the processing pressure will increase the propensity of forming multilamellar vesicles. Decreasing the liquid oil and processing with a larger bore interaction chamber, with or without a reduction in processing pressure will increase the proportion of multilamellar vesicles.

Example 4: Preparation of an Embodiment of the Composition

The following describes some embodiments of lipid nanoparticle powders prepared by spray drying and lyophilization. CBD isolate containing lipid nanoparticles were prepared according to the methods described in the Manufacturing Process of Example 1. In order to spray dry CBD containing lipid nanoparticles, the finished product was mixed with an additional excipient that serves as the lyoprotectant, such as 0%, 5%, 10%, 15%, or 20% of the following alone or in combination lactose, dextrose, trehalose, arginine, glycine, and/or histidine. Excipient was added to the finished product solution and mixed (200 RPM) until dissolved. Additional incubation at room temperature was allowed for material equilibration.

To spray dry the CBD lipid nanoparticles to a powder, a Buchi B290 mini benchtop spray dryer was used. The inlet temperature of the spray-dryer was set at 60-100° C. The aspirator was constant at 35 m³/hour and the feed pump varied up to 5 mL/min. Spray drying parameters were varied such that the outlet temperature was maintained at or below 65° C. and yielding a flowable powder.

To lyophilize the CBD lipid nanoparticles to a powder, a VirTis AdVantage Pro Freeze Dryer was used. Samples were placed in 20 mL glass vials with a stopper half seated. Vials were placed on the lyophilizer shelf and equilibrated at 4° C. for 6 hours before rapidly freezing at −50° C. for 12 hours. Samples were ramped to their lyophilization temperature at a rate of 0.5° C./min. After an additional 30 minutes of equilibration, primary drying commenced with the condenser set at −80° C. and chamber pressure set to 100-200 mTorr. The shelf temperature and duration of primary drying were dependent on which excipient was used, but generally were −20° C. and 24 to 36 hours, respectively. Secondary drying commenced for 6 additional hours at 25° C. and 100-200 mTorr. Following drying, vials were stoppered until further use. To produce a fine powder, samples were milled and passed successively through 75 to 34 micrometer sieves.

TABLE 2

| Sample | Z-Average | Polydispersity Index |
|---|---|---|
| CBD Lipid Nanoparticle Solution | 125.1 nm | 0.133 |
| Reconstituted CBD Lipid Nanoparticle Powder (5% trehalose) After 7 Months of Controlled Room Temperature Storage | 127.6 nm | 0.163 |
| P-Value | 0.115 | 0.285 |

CBD lipid nanoparticle powders were stored in clear glass vials at 25° C./60% relative humidity for 7 months. Powders were reconstituted and particle size analysis was conducted and compared to the original formulation. The original nanoparticle formulation had Z-Average particle size of 125.1 nm (average of three measurements) and the reconstituted powder have a Z-Average particle size of 127.6 nm. Statistical comparison between the two samples resulted in a p-value of 0.115. The polydispersity index of the CBD nanoparticle solution was 0.133 (average of three measurements) and the reconstituted powder had a polydispersity index of 0.163. Statistical comparison between the two samples resulted in a p-value 0.285. The results demonstrate that the CBD containing lipid nanoparticle can be reconstituted and the same particle size characteristics are preserved in the drying process. Further, since it was 7 months later, the particles are advantageously stable in powder form.

Example 5: Preparation of an Embodiment of the Composition

The following describes an embodiment of a solvent-free approach to manufacturing an embodiment of a CBD isolate lipid nanoparticle composition. CBD lipid nanoparticles were prepared using a solvent free method utilizing a high-shear in-line mixer, followed by high pressure homogenization. All water-soluble formulation ingredients, including water soluble flavoring agents, were dissolved into water for injection at the specified concentrations. Aqueous solutions were heated and filtered prior to further use. Warm aqueous solution was transferred to a mixing vessel with an outlet at the bottom of the container that feeds the inlet of a high-shear in-line mixer (Silverson Verso Mixer). The outlet of high-shear mixer utilizes a tube that returns liquid to the top of the mixing vessel. When the warm aqueous solution is transferred to the mixing vessel, the in-line mixer is activated, and the self-pumping action of the mixer moves the liquid through the system.

Method 1. Lipophilic ingredients were accurately weighed into a glass mixing vessel and well dispersed. The lipophilic ingredients were heated with mixing to assist in the dispersion of the materials to form a homogenous lipid slurry. The lipid slurry, including any oil-based flavoring agents, was transferred slowly to the in-line mixing vessel with the mixer activated and emulsified for up to 60 minutes (in a high shear mixer).

Method 2. Lipophilic ingredients were accurately weighed onto a weigh boat and then transferred one at a time to the high-shear mixing vessel with the mixer activated. As each ingredient was introduced, 5 to 10 minutes of mixing was allowed before subsequent additions to allow for homogenous dispersion. Once all lipophilic ingredients were added, the lipid slurry was emulsified for up to 60 minutes while maintaining the processing temperature (in a high shear mixer).

Figure 6:
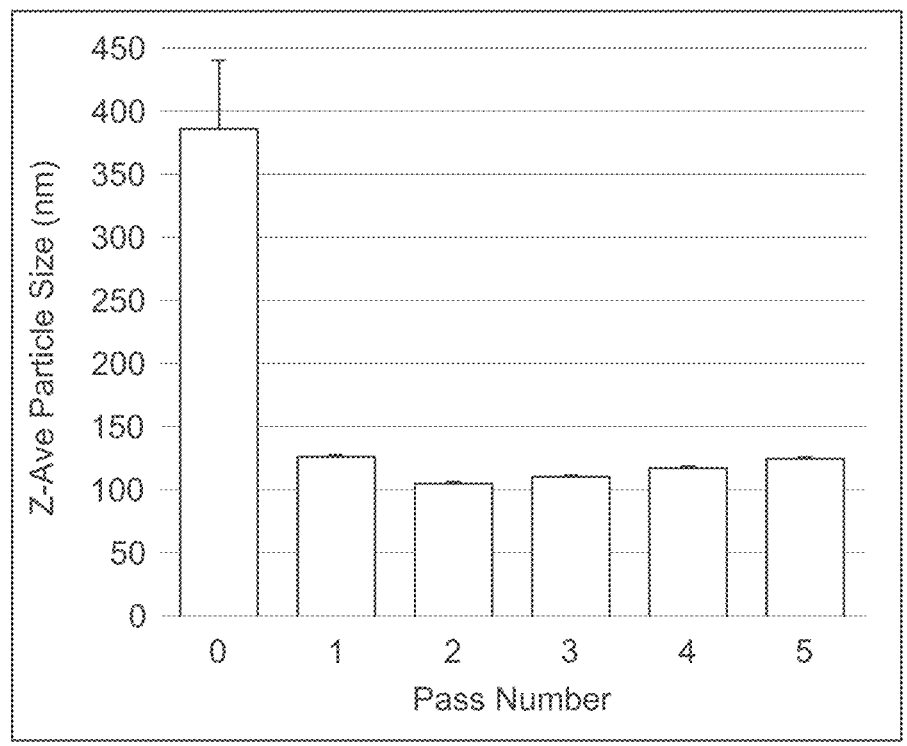
FIG. 6 depicts resulting Z-Average Particle Size of some embodiments after 5 microfluidization passes for embodiments prepared using solvent-free methods.
Figure 7:
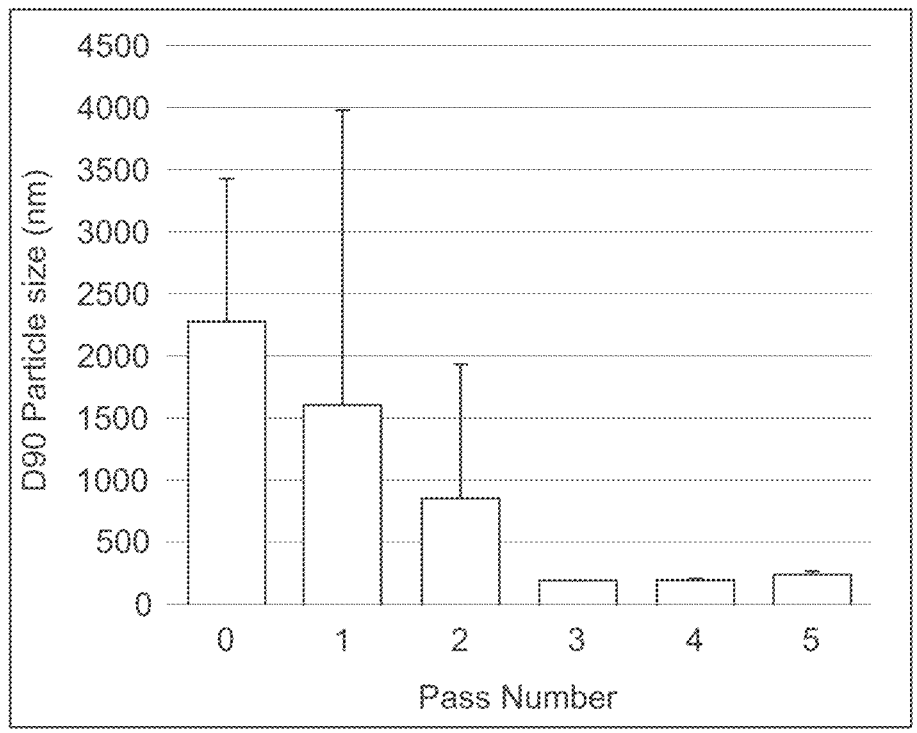
FIG. 7 depicts resulting D90 Particle Size of some embodiments after 5 microfluidization passes for embodiments prepared using solvent-free methods.
Figure 8:
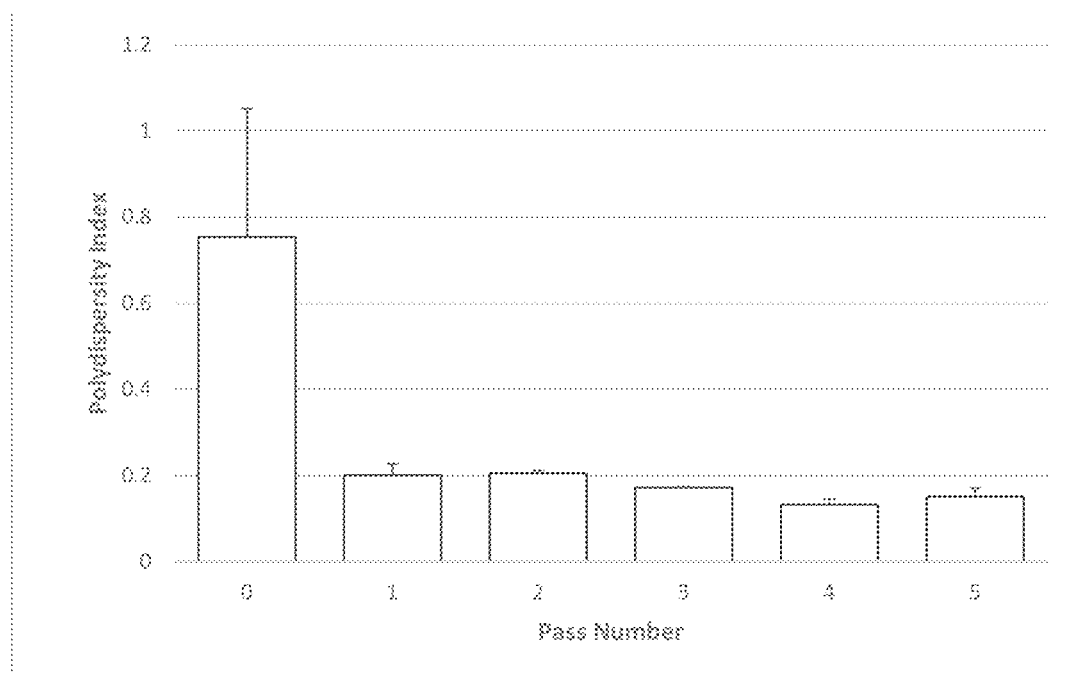
FIG. 8 depicts resulting polydispersity of some embodiments after 5 microfluidization passes for embodiments prepared using solvent-free methods.

The full volume of emulsified lipid solution (as prepared in Method 1 or Method 2) was processed through a microfluidizer (Microfluidics Corporation) for 0 to 10 times at a processing pressure of 10,000-30,000 PSI. The resulting lipid nanoparticle solution was cooled with continuous stirring for a period of 12 to 24 hours before characterization and fill-finish. The data in FIGS. 6 through 8 indicate that a CBD lipid nanoparticle of appropriate particle size distribution, as characterized by the Z-Average, D90 Particle Size, and the polydispersity Index (in FIGS. 6, 7, and 8, respectively), is achieved after 60 minutes of high shear mixing and 3 full passes through a high shear homogenizer.

After the lipid slurry was emulsified for 60 minutes, the dispersion was passed through the microfluidizer 5 times and the resulting Z-Average particle size was measure after each pass (3 measurements per pass). Pass number 0 represents the particle size after high-shear mixing only and had a particle size 385.8±53.1 nm. After 1 pass through the microfluidizer, the resulting particle size decreased to 127.2±1.1 nm (n=3). After 2 and 3 passes through the microfluidizer the resulting particle size was 106.2±1.0 nm and 109.7±1.0 nm. The particle size increased slightly after passes 4 and 5 to 118.0±0.3 nm and 126.2±0.5 nm, respectively.

After the lipid slurry was emulsified for 60 minutes, the dispersion was passed through the microfluidizer 5 times and the resulting D90 particle size was measure after each pass (3 measurements per pass). The D90 particle size describes the diameter where 90% of the distribution has a smaller particle size and 10% has a larger particle size. Pass number 0 represents the particle size after high-shear mixing only and had a particle size 2,266.7±1152.4 nm. After 1 pass through the microfluidizer, the resulting particle size decreased to 1,610.0±2,364.5 nm (n=3). After 2 passes through the microfluidizer, the resulting particle size decreased to 830.3±1.083.2 nm.

After 3, 4, and 5 passes through the microfluidizer the resulting particle size was 185.0±2.0 nm, 191.3±8.4 nm, and 238.7±28.0 nm, respectively.

After the lipid slurry was emulsified for 60 minutes, the dispersion was passed through the microfluidizer 5 times and the resulting polydispersity index was measure after each pass (3 measurements per pass). Pass number 0 represents the polydispersity index after high-shear mixing only was 0.754±0.297. After 1 pass through the microfluidizer, the resulting polydispersity index decreased to 0.201±0.026 (n=3). After 2 and 3 passes through the microfluidizer the resulting polydispersity index was 0.205±0.006 and 0.172±0.002. After passes 4 and 5 the polydispersity index was 0.132±0.013 and 0.151±0.022, respectively.

Example 6: Lipid and CBD Concentration Effect on Nanoparticle Size and Stability CBD containing lipid nanoparticles were prepared using the solvent based manufacturing process in 100 mL batches with varied lipid concentrations to determine their impact on nanoparticle size distribution and short-term stability. Nanoparticles were aliquoted into 20 mL or greater aliquots in clear glass vessels and stored 2-8° C., 25° C. with 60% relative humidity, and 40° C. with 75% relative humidity. At regular intervals the particle size distribution was determined and Z-Average, polydispersity index, and D90 particle size was recorded. The following table summarizes percent weight of ingredients in the formulations studied.

TABLE 3

| Ingredients | F1 | F2 | F3 | F4 | F5 | F6 | F7 | F8 | F9 | F10 |
|---|---|---|---|---|---|---|---|---|---|---|
| HSPC (g) | 10 | 10 | 10 | 10 | 6 | 6 | 6 | 3 | 3 | 1 |
| Cholesterol (g) | 1 | 1 | 1 | 1 | 0.6 | 0.6 | 0.6 | 0.3 | 0.3 | 0.1 |
| MCT (g) | 9.6 | 5.76 | 2.88 | 0.96 | 5.76 | 2.88 | 0.96 | 2.88 | 0.96 | 0.96 |
| CBD (g) | 2 | 2 | 2 | 2 | 2 | 2 | 2 | 2 | 2 | 2 |
| Vitamin E (g) | 0.05 | 0.05 | 0.05 | 0.05 | 0.05 | 0.05 | 0.05 | 0.05 | 0.05 | 0.05 |
| Sodium Benzoate (g) | 0.1 | 0.1 | 0.1 | 0.1 | 0.1 | 0.1 | 0.1 | 0.1 | 0.1 | 0.1 |
| Potassium Sorbate (g) | 0.1 | 0.1 | 0.1 | 0.1 | 0.1 | 0.1 | 0.1 | 0.1 | 0.1 | 0.1 |
| Citric Acid Monohydrate (g) | 0.1 | 0.1 | 0.1 | 0.1 | 0.1 | 0.1 | 0.1 | 0.1 | 0.1 | 0.1 |
| Malic Acid (g) | 0.01 | 0.01 | 0.01 | 0.01 | 0.01 | 0.01 | 0.01 | 0.01 | 0.01 | 0.01 |
| Water For Injection (g) | 77.04 | 80.88 | 83.76 | 85.68 | 85.28 | 88.16 | 90.08 | 91.46 | 93.38 | 95.58 |

HSPC is hydrogenated sunflower phosphatidylcholine, MCT is medium chain triglyceride, and CBD is cannabidiol. The following table summarizes the percent change of each particle size distribution parameter for each formulation after 90 days of storage at the state temperature. A negative number indicates the parameter was less than the starting measurement, where a positive number indicates the parameter was greater than the starting measurement. All numbers are the average of three measurements. NA indicates data was not available.

TABLE 4

| | 2-8° C. Storage Temperature | | | 25° C./60% RH Storage Temperature | | | 40° C./75% RH Storage Temperature | | |
|---|---|---|---|---|---|---|---|---|---|
| | Z-Ave | PDI | D90 | Z-Ave | PDI | D90 | Z-Ave | PDI | D90 |
| F1 | 5.05 | 16.11 | 14.06 | 3.03 | 4.63 | 4.45 | 27.96 | 151.01 | 159.66 |
| F2 | 8.70 | 17.74 | 32.17 | −0.18 | 30.3 | 48.6 | 41.73 | 292.44 | 124.38 |
| F3 | 30.05 | 36.95 | 185.78 | 68.18 | 85.04 | −55.47 | 416.33 | −18.46 | 75.07 |
| F4 | 228.86 | −13.88 | −32.97 | 153.56 | −29.03 | −84.06 | 104.38 | −32.79 | 3.35 |
| F5 | 14.05 | 35.40 | 915.88 | 12.98 | 40.68 | 901.81 | 24.10 | 352.55 | 102.26 |
| F6 | 172.53 | 54.75 | −71.26 | 25.38 | 96.39 | 30.88 | NA | NA | NA |
| F7 | 124.89 | 100.00 | −99.90 | 83.97 | 89.20 | −70.69 | 455.48 | 73.11 | −32.67 |
| F8 | 8.78 | 15.05 | 26.82 | 11.03 | 32.90 | 54.60 | 38.97 | 149.35 | 193.85 |
| F9 | 144.84 | 110.28 | −20.00 | 48.06 | 85.08 | −36.91 | 57.50 | 70.85 | −33.40 |
| F10 | 260.94 | 157.67 | −54.46 | −5.63 | 30.97 | 328.80 | 7.76 | 30.09 | 51.10 |

In general, CBD containing lipid nanoparticles were smaller with higher total lipid to CBD ratios, including a greater oil phase composition. A similar trend was observed with PDI, a higher total lipid to CBD ratio and higher oil content had a more homogenous particle size distribution. Following 90 days of storage at the specified storage conditions, formulations with high lipid and oil content experienced less percent change in particle size and PDI.

Example 7: Pharmacokinetics of CBD Lipid Nanoparticle Solutions and Powders

CBD containing lipid nanoparticles were prepared according to the solvent based manufacturing process using formulation ingredients outlined in batches 2 & 4 in Example 1. Powders of the CBD containing lipid nanoparticles were prepared according to the methods outlined in Example 4.

The pharmacokinetics of liquid and powder in capsule lipid formulations of CBD were determined in male Gottingen mini-pigs at a dose of 15 mg/kg. Mini-pigs (20-24 kg) were orally administered the product into the stomach by an oral gavage tube. Blood samples were collected via an accessible vein into blood tubes containing potassium EDTA. Blood samples were collected at 0 (pre-dose), 0.25, 0.5, 1, 1.5, 2, 2.5, 3, 4, 5, 6, 8, 10, 12, 14, and 16 or 24 hours. CBD concentration and metabolites were measured in blood plasma by HPLC. Pharmacokinetic parameters were determined from the plasma concentrations using PK Solver, a Microsoft Excel plug-in, or by hand using the linear trapezoid rule. For comparison, leading commercially available, oil-based CBD products were also evaluated after oral administration.

Figure 9A:
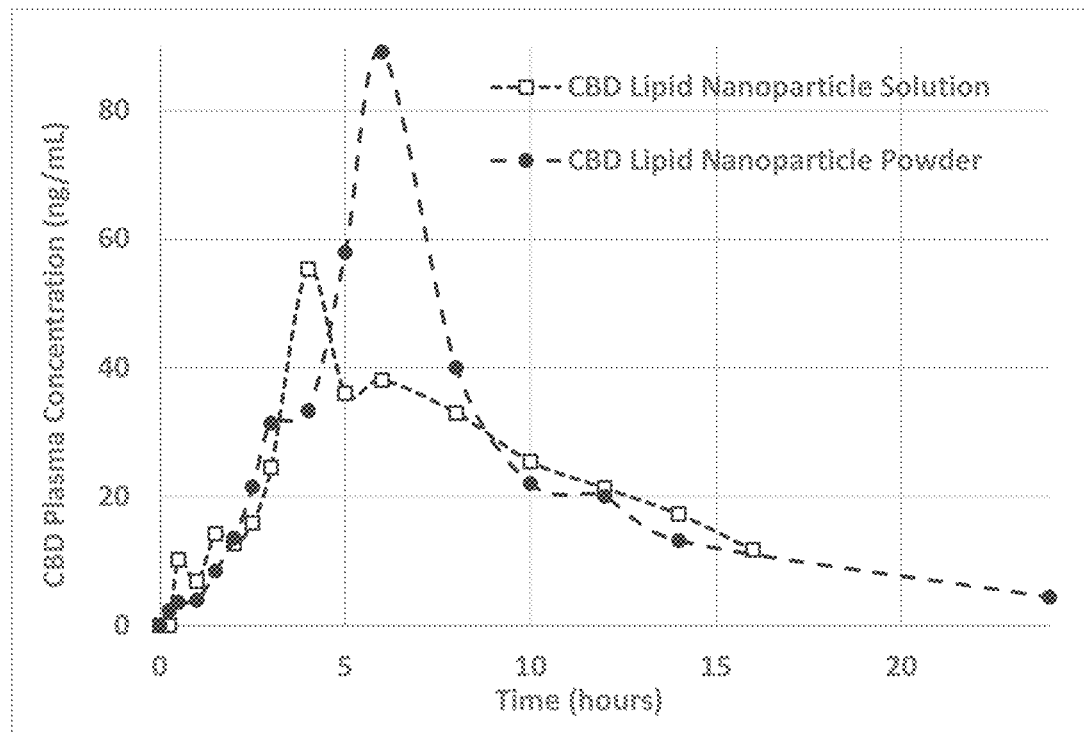
FIG. 9A-D depict the pharmacokinetic profiles of certain embodiments of CBD lipid nanoparticle solutions, CBD lipid nanoparticle powders and CBD oil-based commercial comparators.
Figure 9B:
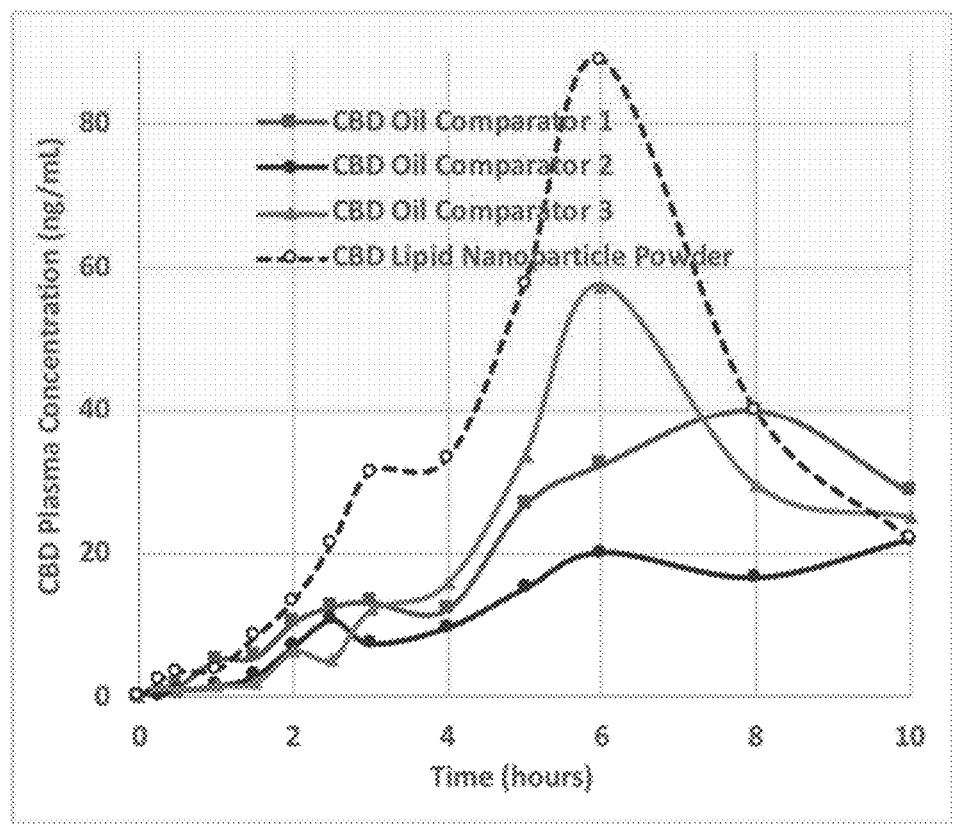
Figure 9C:
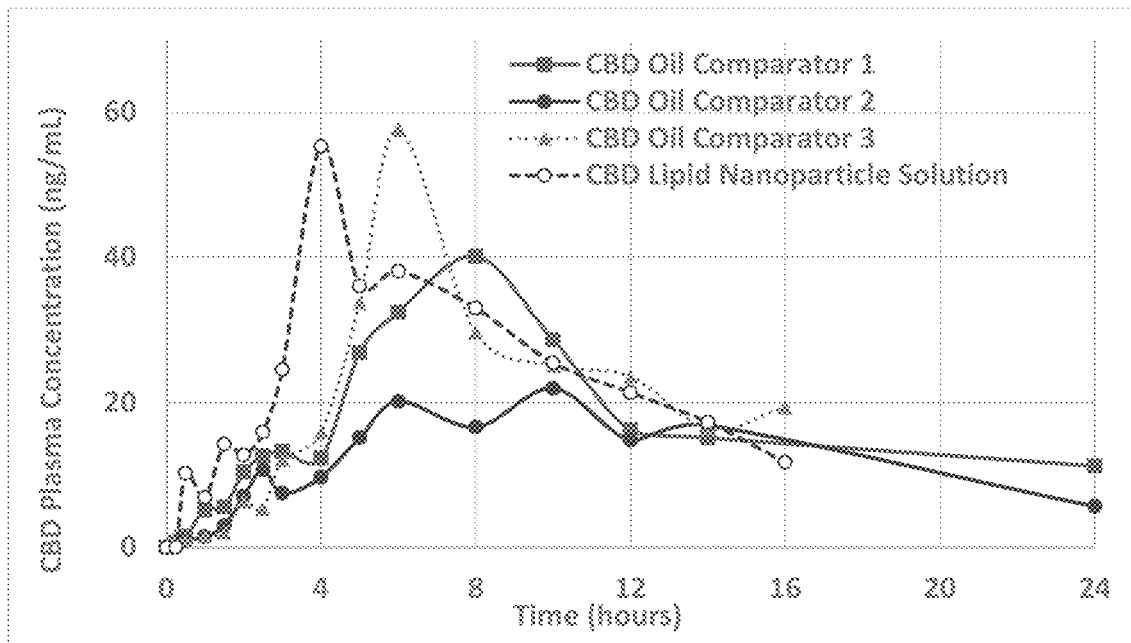
Figure 9D:
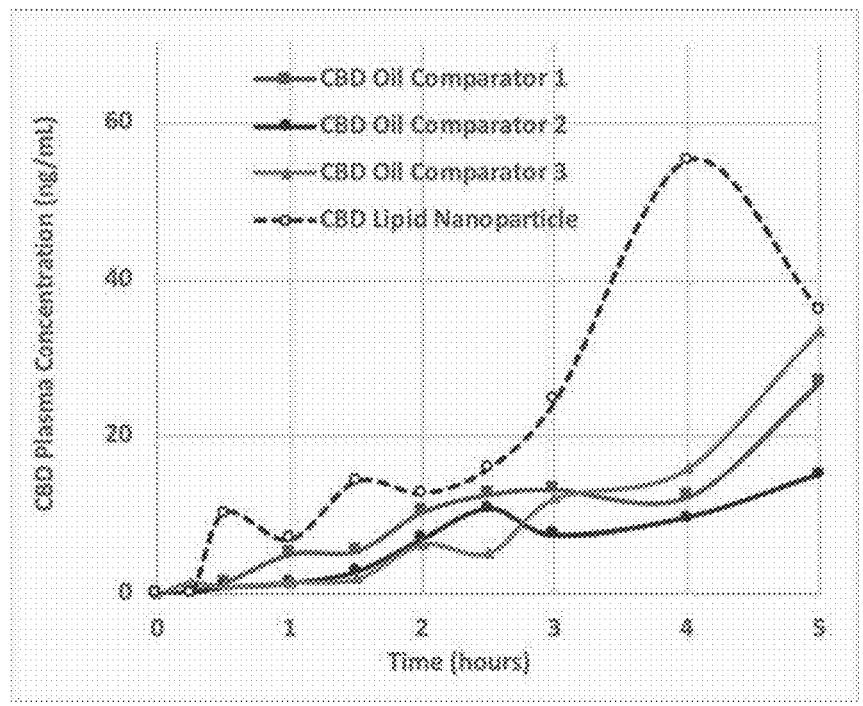

Shown in FIG. 9A-D are the pharmacokinetic profiles of CBD containing lipid nanoparticles in solution as well the powder formulation filled in gelatin capsules. FIG. 9A shows two embodiments as disclosed herein. As demonstrated, the nanoparticle powder had an increased Cmax and the solution had an increased Tmax. FIG. 9B shows that the powder formulation in gelatin capsules had a Cmax that was approximately 63% higher than the CBD-oil comparators. As shown in FIGS. 9C and 9D, the solution formulation had faster Tmax (~4 hours) compared to the CBD-oil comparators, which had a Tmax of greater than 6 hours and close to 8 hours in some samples. FIGS. 9C and 9D show the CBD lipid nanoparticle solution had detectable concentrations of CBD earlier than the oil-based comparators (within the first hour of the study), as well as reached an apparent Tmax approximately 2 hours earlier than oil-based comparator 3, 4 hours earlier than oil-based comparator 1, and 6 hours earlier than oil-based comparator 2. The CBD lipid nanoparticles reached a higher plasma concentration than comparators 1 and 2.

Figure 10:
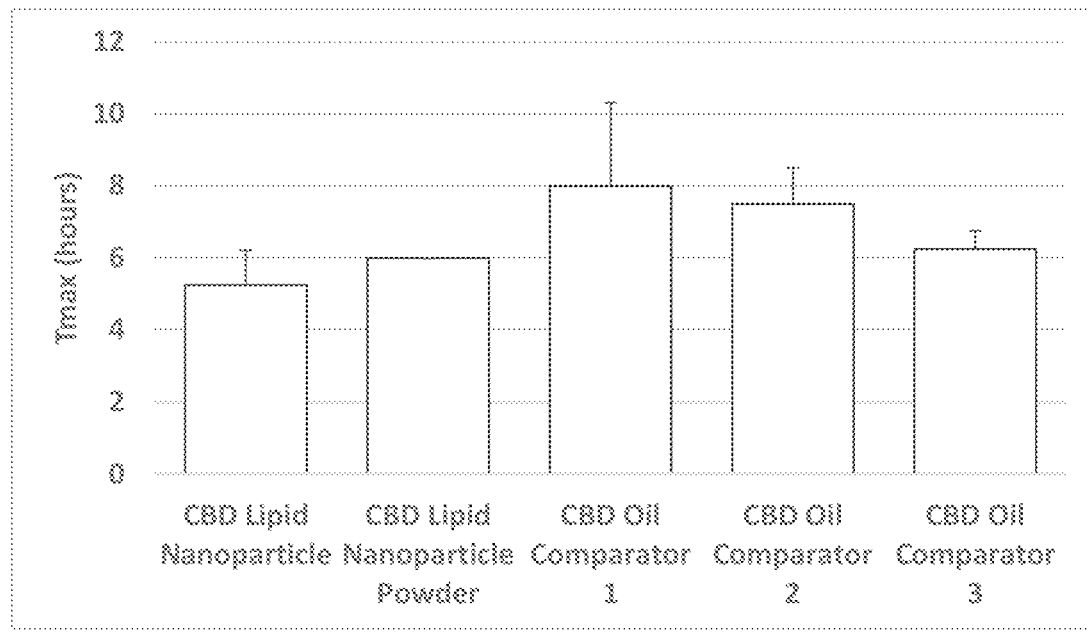
FIG. 10 depicts the Tmax for of CBD lipid nanoparticle as disclosed herein compared to and CBD oil-based commercial comparators.

Shown in FIG. 10 is the comparison of the absorption phase of the CBD lipid nanoparticle solutions over the first four hours of the study, and three leading oil-based CBD commercial comparators. For the CBD lipid nanoparticles, measurable levels of CBD were detected in plasma within 30 minutes. The rates of absorption were taken to be the slope of the regression equation. The rate of the absorption for the CBD lipid nanoparticle solution was statistically significant compared to the CBD oil-based comparators (ANOVA, p=0.0417).

Figure 11:
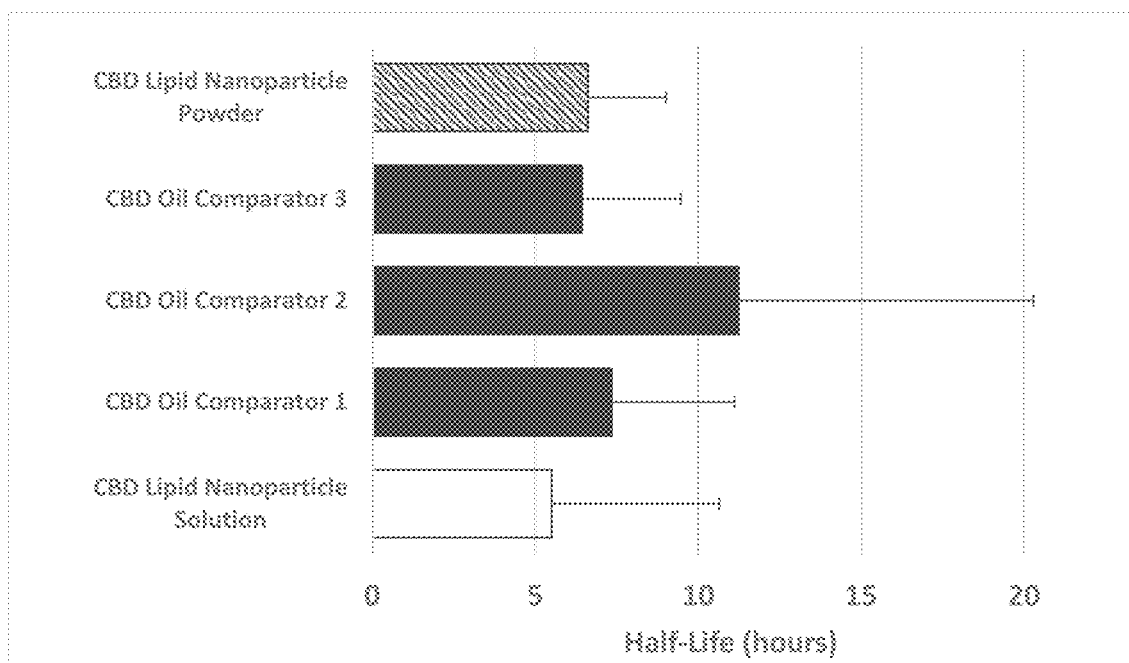
FIG. 11 depicts Half-Lives ($T_{1/2}$) of some embodiments of CBD lipid nanoparticle solutions, powders, and oil-based commercial comparators.

The CBD lipid nanoparticle solution formulation had the shortest half-life of 5.5±5.2 hours and the CBD lipid nanoparticle powder formulation having a half-life of 6.6±2.4 hours (FIG. 11). The CBD oil-based comparators had half-lives generally greater than the liquid formulation, of 6.4±3.0, 11.2±9.1, and 7.3±3.8 hours.

| Group | $AUC_{0-4}$ (ng/mL*hr)* | $AUC_{4-6}$ (ng/mL*hr)* | $AUC_{6-10}$ (ng/mL*hr)* | $AUC_{0-inf}$ (ng/mL*hr)** |
|---|---|---|---|---|
| CBD Lipid Nanoparticle | 98.4 ± 45.2 | 84.0 ± 64.3 | 129.4 ± 31.5 | 557.8 ± 297.5 |
| CBD Lipid Nanoparticle Powder | 65.8 ± 25.5 | 119.0 ± 12.9 | 191.0 ± 58.1 | 575.9 ± 211.5 |
| CBD Oil Comparator 1 | 21.9 ± 20.2 | 28.2 ± 20.9 | 70.7 ± 36.0 | 393.8 ± 133.0 |
| CBD Oil Comparator 2 | 33.7 ± 26.9 | 49.2 ± 21.2 | 141.2 ± 45.3 | 352.1 ± 216.9 |
| CBD Oil Comparator 3 | 24.7 ± 16.1 | 84.0 ± 64.3 | 141.9 ± 64.5 | 568.7 ± 311.1 |

Figure 12:
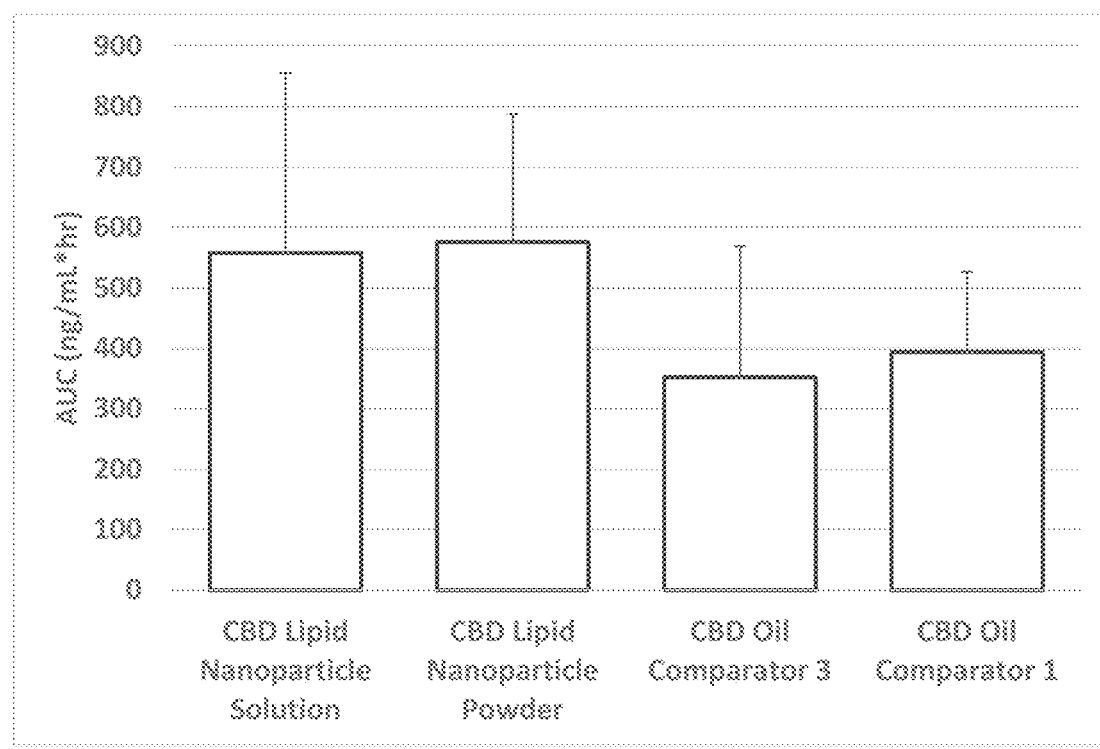
FIG. 12 depicts Area Under The Curve (AUC) of some embodiments of CBD lipid nanoparticle solutions, powders, and oil-based commercial comparators.

FIG. 12 shows AUC or Area Under the Curve information (0 to infinity). AUC is a pharmacokinetic parameter that reflects a molecule's total exposure. The CBD lipid nanoparticle solution had an AUC of 557.8±297.5 ng/mL*hr, where the CBD lipid nanoparticle powder had an AUC of 575.9±211.5 ng/mL*hr. Despite having a significantly greater Cmax (shown in FIG. 9), both liquid and powder formulations had comparable AUCs. Both oil-based CBD comparators had AUCs that were lower than the Lipid Nanoparticle formulation. Comparator 3 had an AUC of 352.1±216.9 and comparator 1 had an AUC of 393.8±133.0 ng/mL*hr. Indicating the oil-based CBD products had less total exposure than the lipid nanoparticle formulations.

Shown in Table 5 are the AUCs for 0-4 hr and 0—infinity hours (0—infinity calculated using PKSolver, the rest were calculated using the linear trapezoid equation). The $AUC_{0-4}$ for the CBD lipid nanoparticles and powder was 98.4±45.2 and 65.8±25.5 ng/mL*hr, respectively. The CBD oil comparators had AUCs for this same period of time were 21.9±20.2, 33.7±26.9, and 24.7±16.1 ng/mL*hr. The $AUC_{4-6}$ for the CBD lipid nanoparticles and powder was 84.0±64.3 and 119.0±12.9 ng/mL*hr, respectively. The AUCs for this same period of time were 28.2±20.9, 49.2±21.2, and 84.0±64.3 ng/mL*hr for the oil based comparators. The $AUC_{6-10}$ for the CBD lipid nanoparticles and powder was 129.4±31.5 ng/mL*hr and 191.0±58.1 ng/mL*hr. The AUCs for the CBD oil based comparators were 70.7±36.0, 141.2±45.3, and 141.9±64.5 ng/mL*hr over the same period of time. The higher AUCs during the first 4 hours of the study in the CBD lipid nanoparticle groups demonstrate the rapid absorption compared to the oil-based comparators.

TABLE 5

| Group | AUC0-4 (ng/mL*hr)* | AUC0-inf (ng/mL*hr)** |
|---|---|---|
| CBD Lipid Nanoparticle | 98.4 ± 45.2 | 557.8 ± 297.5 |
| CBD Lipid Nanoparticle Powder | 65.8 ± 25.5 | 575.9 ± 211.5 |
| CBD Oil Comparator 1 | 21.9 ± 20.2 | 393.8 ± 133.0 |
| CBD Oil Comparator 2 | 33.7 ± 26.9 | 352.1 ± 216.9 |
| CBD Oil Comparator 3 | 24.7 ± 16.1 | 568.7 ± 311.1 |

*Calculated by hand/Excel using the linear trapezoid rule
**Calculated by PKSolver for Excel

Example 8: Preservative Systems of CBD Containing Lipid Nanoparticles

CBD containing lipid nanoparticles were prepared using the solvent based manufacturing process, however, different concentrations of preservatives were dissolved in the aqueous solution prior to hydration of the lipid film and mixing. Citric acid monohydrate and malic acid was added to Formulation 1 at 6.10 and 5.73 mM, respectively. In Formulation 2, citric acid was added at 4.88 mM and no malic acid was added. In Formulation 3, citric acid was added 0.16 mM and no malic acid was added. In Formulation 4, no citric or malic acid was added. All formulations contained 8.53 mM of potassium sorbate and 8.90 mM of sodium benzoate. Formulations were characterized for pH, particle size distribution, zeta potential, CBD concentration and particle size after storage for 6 or 7 months at 2-8° C., 25° C. with 60% relative humidity, and 40° C. with 75% relative humidity, and a preservative effectiveness challenge. The table below summarizes Formulation initial characterization data.

TABLE 6

| Form. | Solution pH | Z-Average Particle Size | D90 Particle Size | Polydispersity Index | Zeta Potential |
|---|---|---|---|---|---|
| 1 | 4.072 | 102.3 ± 0.61 nm | 146.3 ± 3.61 nm | 0.164 ± 0.005 | +2.29 mV |
| 2 | 4.459 | 103.2 ± 0.94 nm | 149.0 ± 4.16 nm | 0.174 ± 0.019 | +3.25 mV |
| 3 | 5.093 | 103.3 ± 0.85 nm | 149.0 ± 3.21 nm | 0.166 ± 0.007 | +3.00 mV |
| 4 | 6.250 | 99.8 ± 1.35 nm | 135.7 ± 4.01 nm | 0.156 ± 0.025 | +1.82 mV |

Figure 13:
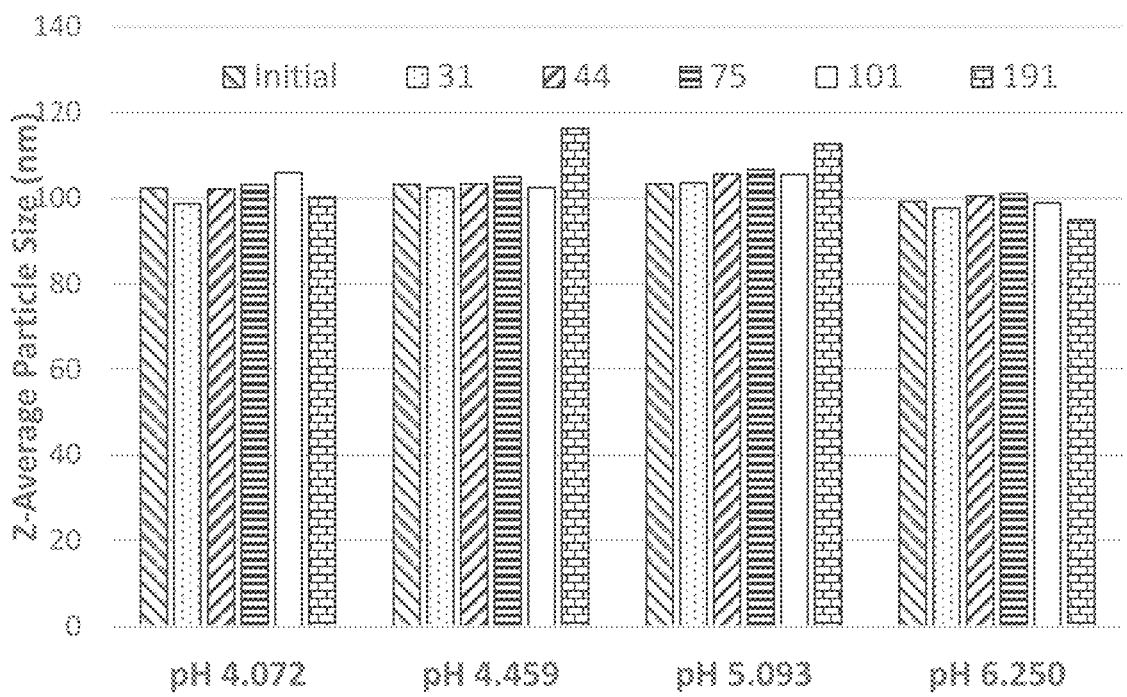
FIG. 13 shows data for the change in CBD lipid nanoparticle particle size in some embodiments over approximately 6 months at different solution pH.
Figure 14:
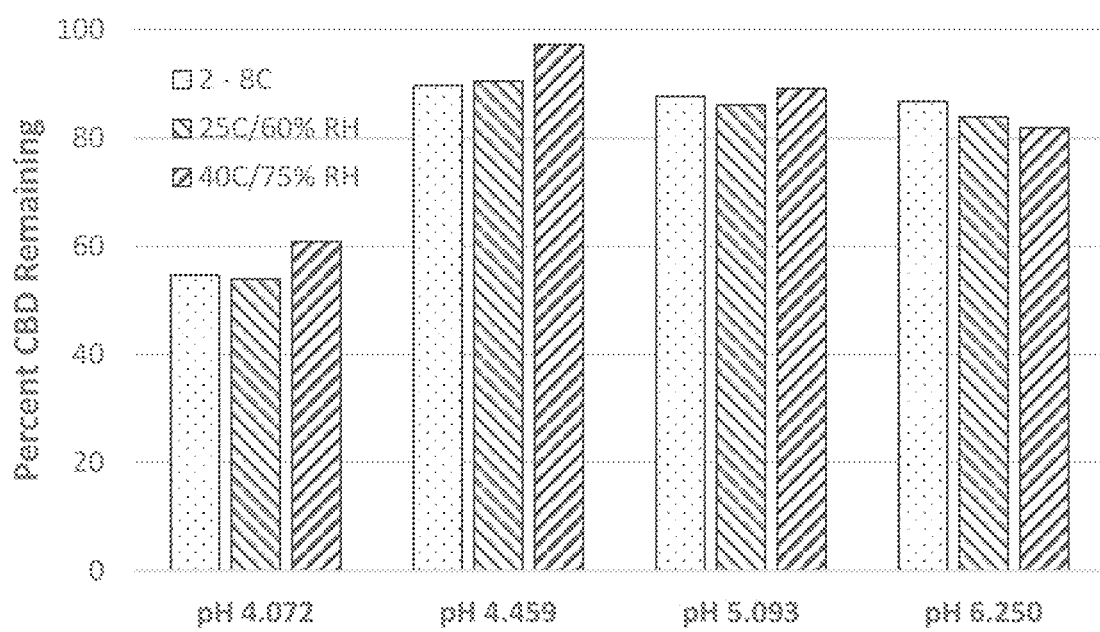
FIG. 14 shows data for the change in CBD concentration in certain embodiments of lipid nanoparticles after 7 months at different storage conditions.

FIG. 13 shows the change in CBD lipid nanoparticle size over approximately 6 months at differing solution pH values. FIG. 14 shows the change in CBD concentration in lipid nanoparticles over approximately 7 months at differing storing conditions. Solution pH did not impact the stability of the particle size (FIG. 13) when measure at regular intervals over approximately 6 months of storage at 25° C. with 60% relative humidity. After 7 months of storage at 2-8° C., 25° C. with 60% relative humidity, and 40° C. with 75% relative humidity, the percent CBD remaining was significantly less for pH 4.072 compared to the formulation groups.

To determine the effectiveness of the preservative system, the formulations were challenged with 5 microorganisms (*E. coli*, *P. aeruginosa*, *S. aureus*, *A. brasiliensis*, and *C. albicans*) at $10^7$ CFU/mL and the log reduction in colony forming units after incubation for 7 days was calculated.

TABLE 7

| Formulation pH | E. coli | P. aeruginosa | S. aureus | A. brasiliensis | C. albicans |
|---|---|---|---|---|---|
| Formulation 1 | >4.18 | >4.30 | >4.08 | >1.75 | >1.00 |
| Formulation 2 | >4.18 | >4.30 | >4.08 | 1.63 | 1.00 |
| Formulation 3 | 0.37 | >4.30 | >4.08 | 0.12 | None |
| Formulation 4 | 1.03 | None | 0.74 | None | 0.07 |

The minimum require for an effective preservative system is at least a 1.0 log reduction in colony forming units for each organism evaluated after 7 days of incubation. Preservative systems with a pH of 4.459 and 4.07 s met the minimum requirements of a preservative system, but solutions with a pH of 5.093 and 6.250 did not. The preservative systems evaluated in this study were more effective at preventing bacterial growth, especially at lower pH, than yeasts and molds.

Example 9: Higher Concentrations of CBD in the Lipid Nanoparticle Formulation

CBD containing lipid nanoparticles were prepared using the solvent based manufacturing process outlined above. In this example, the lipid ratios were fixed with respect to each other and the CBD concentration was varied. Formulation compositions are outlined in the table below. Formulations were stored at 2-8° C., 25° C. with 60% relative humidity, and 40° C. with 75% relative humidity for 100 days and the particle size distribution was determined. Results reported are the average percent change from the initial conditions recorded on day 0 (n=3 measurements per sample, per time point). A positive number indicates the particle size parameter increased with respect to day 0, while a negative number indicates the parameter decreased with respect to day 0.

TABLE 8

| | Percent CBD By Weight | Percent Lipid By Weight | Percent Water By Weight |
|---|---|---|---|
| Formulation No. 29 | 3.00 | 20.67 | 76.32 |
| Formulation No. 30 | 4.00 | 20.67 | 75.32 |
| Formulation No. 31 | 5.00 | 20.67 | 74.32 |
| Formulation No. 32 | 2.00 | 12.42 | 85.58 |
| Formulation No. 33 | 3.50 | 12.42 | 84.07 |
| Formulation No. 34 | 6.00 | 12.42 | 81.57 |
| Formulation No. 36 | 4.00 | 12.42 | 83.57 |

The table below summarizes the results of the study as percent change in Z-average particle size and polydispersity index after 100 days of storage at the stated storage temperature. Despite the percent change in particle size parameters at any storage temperature, all were within the product's specification, indicating that CBD can be incorporated into the formulation beyond 2%.

TABLE 9

| Formulation | 2-8° C. Storage Temperature | | 25° C./60% RH Storage Temperature | | 40° C./75% RH Storage Temperature | |
|---|---|---|---|---|---|---|
| | Z-Ave | PDI | Z-Ave | PDI | Z-Ave | PDI |
| Formulation No. 29 | 7.36 | 13.71 | 4.25 | 35.05 | 71.95 | 57.14 |
| Formulation No. 30 | 7.71 | 5.17 | 7.28 | 54.87 | 71.25 | 54.27 |
| Formulation No. 31 | 6.94 | −1.8 | 11.95 | 101.00 | 51.70 | 46.00 |

TABLE 9-continued

| Formulation | 2-8° C. Storage Temperature | | 25° C./60% RH Storage Temperature | | 40° C./75% RH Storage Temperature | |
|---|---|---|---|---|---|---|
| | Z-Ave | PDI | Z-Ave | PDI | Z-Ave | PDI |
| Formulation No. 32 | 7.02 | 2.46 | 7.60 | 49.08 | 80.36 | 44.36 |
| Formulation No. 33 | 14.49 | 23.23 | −1.23 | 38.38 | 70.79 | 96.21 |
| Formulation No. 34 | 6.26 | 8.64 | 8.32 | 120.74 | 64.6 | 90.37 |
| Formulation No. 36 | NA | NA | 10.63 | 90.78 | 57.13 | 40.67 |

Example 10: CBD Containing Lipid Nanoparticles can be Filtered

CBD containing lipid nanoparticles were prepared using the solvent based method at a 10 liter batch size. Prior to further study, the nanoparticles were characterized for particle size distribution and CBD concentration. To filter the material, the nanoparticle solution was transferred to a pressurized vessel containing a stainless-steel side arm. To the side arm, Pharmed BPT tubing was used to connect the pressurized vessel to a receiving vessel, with a 3M betafine filter in-line. To filter the nanoparticle solution, nitrogen gas was filled into the pressurized vessel to displace the solution forcing it through the filter and into the receiving vessel. Two 3M betafine filters were evaluated in this study, a 0.2 micron and 0.65 micron polypropylene filter. After filtration, the particle size distribution and CBD concentration was measured again and compared to the starting measurements. All measurements were performed in triplicate.

TABLE 10

| Parameter | Starting Measurements | After 3M Betafine 0.20 Micron Filter | After 3M Betafine 0.65 Micron Filter |
|---|---|---|---|
| Z-Average Particle Size | 103.5 nm | 101.5 nm | 101.2 nm |
| Polydispersity Index | 0.184 | 0.123 | 0.154 |
| D90 Particle Size | 179.0 nm | 151 nm | 155.7 nm |
| CBD Concentration | 20.0 mg/mL | 20.0 mg/mL | 20.0 mg/mL |

No change in the particle size parameters and CBD concentration before and after filtration indicates the product can be filtered at a 0.2 micron cutoff without any loss of material. Further indicating the product may be sterile-filtered through a 0.22 micron sterile filter.

Figure 15:
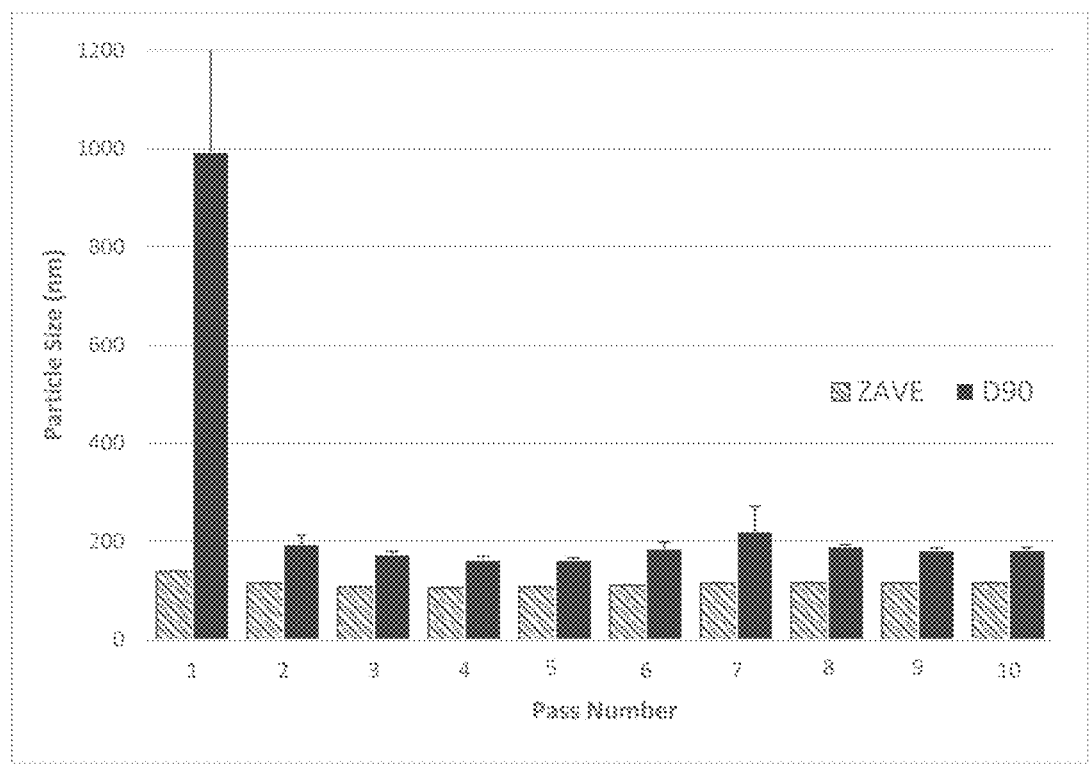
FIG. 15 shows data for various passes through a microfluidizer, including an initial particle size measurements after 1 pass through 10 passes.
Figure 16:
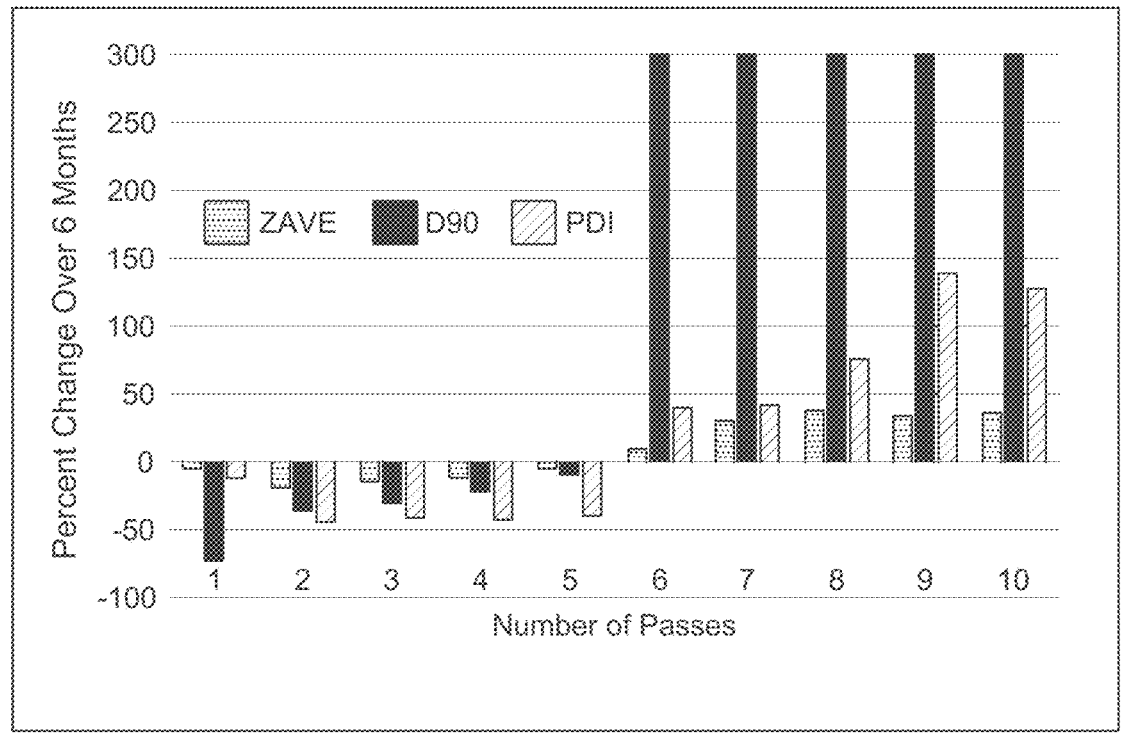
FIG. 16 shows data for different particles after various passes through a microfluidizer, including particles after 1 pass through 10 passes after storage for 6 months at 25° C. with 60% relative humidity.

Example 11: Resulting Particle Size Distribution by Operating Pressure and Pass Number CBD containing lipid nanoparticles were prepared by the solvent based manufacturing process in batch sizes of 100 mL. The purpose of the first part of the study was to determine the impact of pass number on the initial particle size distribution and any changes after 6 months of storage at 25° C. with 60% relative humidity. The full volume of lipid slurry was microfluidized 10 times with a sample collection after each volume for analysis. Shown below in FIG. 15 is the Z-Average and D90 particle sizes. After 1 pass through the microfluidizer, the Z-Average was below 200 nm but the D90 particle size was 1.0 micron. After 2 passes through the microfluidizer both the Z-Average and D90 were below 200 nm. The difference between the particle sizes decreased with subsequent passes up to pass 5. Starting with and after pass 6, the two particle sizes increased in difference. Interestingly, the percent change in particle size parameters decreased slightly after 6 months of storage at 25° C. with 60% relative humidity for passes 1 through 5 (FIG. 16). However, significant increases in the D90 and PDI were observed for passes 6 through 10 during the same storage conditions and time. The D90 particle size increased by at least 300% for passes 6 through 10.

Figure 17A:
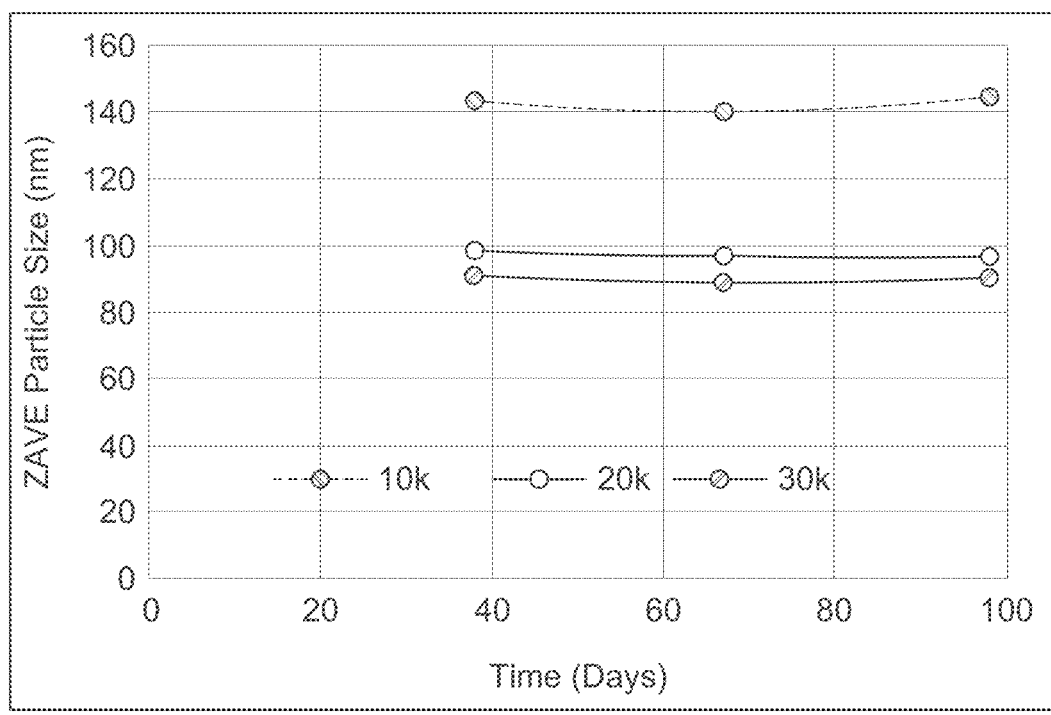
FIG. 17A-C shows change in particle size distribution by operating pressure measured using Z average, D90 particle sizing, and polydispersity index, respectively.
Figure 17B:
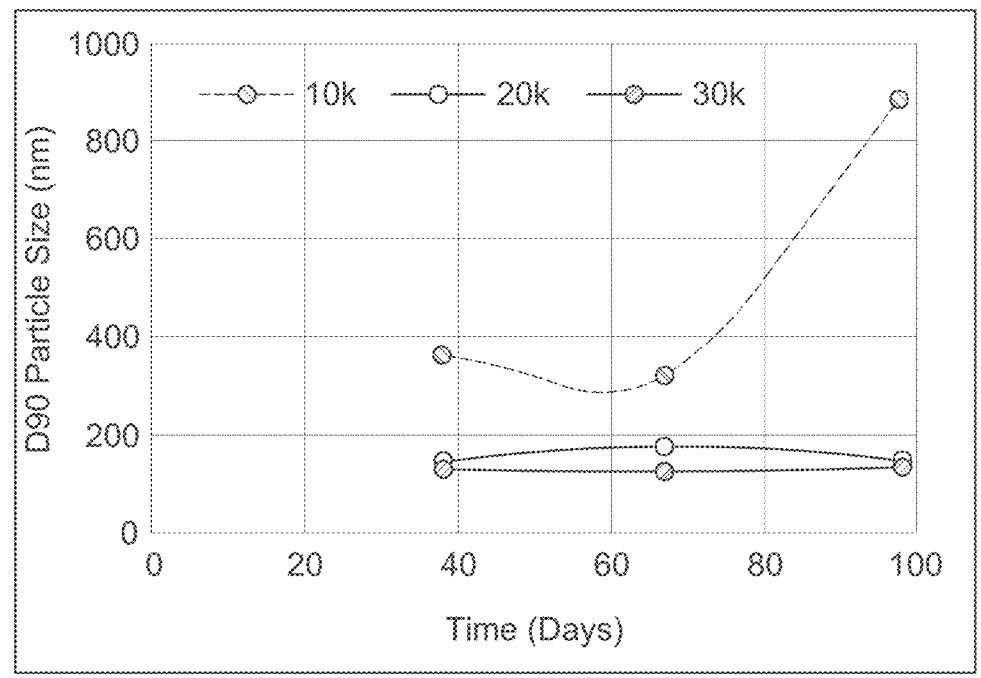
Figure 17C:
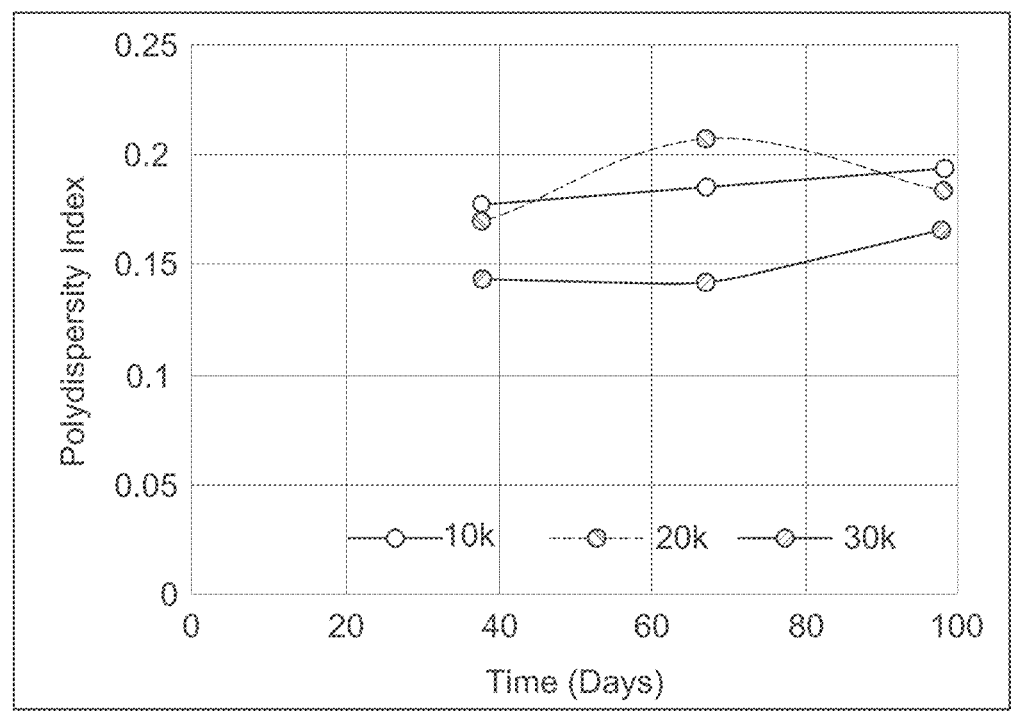

In the second part of this study, batches of CBD containing lipid nanoparticles were prepared at different microfluidizer operating pressures and the impact on the particle size distribution was measure over 90 days of storage at 25° C. with 60% relative humidity. Shown below in FIG. 17A-C is the Z-Ave, D90 particle sizes, and polydispersity index, respectively, by operating pressure. The Z-Ave particle size decreased with increasing operating pressure, with the most dramatic difference being between 10,000 and 20,000 PSI. During the 90-day storage period the Z-Ave particle size did not significantly change with any operating pressure. A similar trend was observed with the D90 particle size. However, the batch prepared at 10,000 PSI showed a significant increase in particle size at day 90 compared to the 20,000 and 30,000 PSI operating pressures. The difference in polydispersity index wasn't as dramatic as particle size and didn't change over 90 days (the ~70 day measurement at 20,000 PSI being an exception).

Example 12: CBD Containing Lipid Nanoparticles Prepared with Several CBD Isolates CBD containing lipid nanoparticles were prepared using the solvent based manufacturing process or the solvent free, high shear mixing process in 100 mL batches. Lipid nanoparticles were prepared with CBD isolate from different manufacturers, all of which had greater than 99% CBD purity and no detectable THC. Nanoparticles were prepared at 20 mg/mL and the final concentration was verified by UHPLC. All preparations had a Z-average particle size between 85.4 nm and 105.6 nm, a D90 particle size of 113.0 nm to 153.2 nm, and a polydispersity index of 0.105 to 0.169. Lipid nanoparticles prepared with Gen Canna, Global Cannabinoids, and Mile High Labs CBD isolate was not significantly different from that prepared with Boulder Botanicals CBD isolate, indicating similar nanoparticle attributes are attainable regardless of the CBD isolate origin. The results of this example are summarized in the table below.

TABLE 11

| Manufacturer | Percent CBD Composition | Percent THC Composition | Z-Ave Particle Size | D90 Particle Size | Polydispersity Index |
|---|---|---|---|---|---|
| Boulder Botanicals | 99.97% | Not Detected | 104.4 nm | 151.0 nm | 0.158 |
| Gen Canna | >99% | Not Detected | 105.6 nm | 153.2 nm | 0.169 |
| Global Cannabinoids | 99.93% | Not Detected | 85.4 nm | 113.0 nm | 0.105 |
| Mile High Labs | 99.30% | Not Detected | 94.84 nm | 131.0 nm | 0.129 |

Example 13: CBD Containing Lipid Nanoparticles Prepared with Full or Broad Spectrum CBD Material CBD containing lipid nanoparticles were prepared by the solvent based and/or solvent free manufacturing process in 0.1 liter batches. In this example, the CBD origin was from a full spectrum or broad spectrum hemp extract where the CBD content varied from 44.25% to 86.6%. The THC content was below 0.3% or not detectable. All formulations were prepared to a final concentration of 20 mg/mL CBD and confirmed by UHPLC. Modifications to the remaining lipids in the formulations were made to accommodate the lower concentration of CBD in the full/broad spectrum hemp extracts. All formulations had a Z-average particle size between 94.88 nm and 178.0 nm, a D90 particle size between 132.0 nm and 265.0 nm, and a polydispersity index of 0.100 to 0.221. The resulting particle size attributes were not different from those prepared with CBD isolate, indicating the broad or full spectrum CBD can be exchanged with CBD isolate in the lipid nanoparticle formulation. The results of this study are summarized in the table below.

TABLE 12

| Manufacturer | Percent CBD Composition | Percent THC Composition | Z-Ave Particle Size | D90 Particle Size | Polydispersity Index |
|---|---|---|---|---|---|
| Boulder Botanicals Full Spectrum CBD Extract | | | 94.88 nm | 132.0 nm | 0.152 |
| Klersun NDT Broad Spectrum Hemp Extract | 83.16% | <0.3% | 98.15 nm | 138.0 nm | 0.138 |
| Mile High Labs Broad Spectrum THC Free Distillate | 86.6% | Not Detected | 98.87 nm | 193.0 nm | 0.221 |
| Charlotte's Web Hemp Oil Concentrate | 44.25% | <0.3% | 178.0 nm | 265.0 nm | 0.100 |

Example 14: Lipid Nanoparticles Prepared with CBG Isolate, CBN Distillate, and CBDa Oil Lipid nanoparticles were prepared with other commercially available cannabinoids using the solvent based manufacturing process and characterized for particle size distribution. Global cannabinoids CBG isolate had 93.34% CBG by weight, with no other cannabinoids detected (based on Manufacturer's COA). The Z-average particle size was 105.6 nm, the D90 particle size was 241.0 nm, and the polydispersity index was 0.206. Lipid nanoparticles were prepared with CBN distillate from global cannabinoids. The CBN distillate was 80.5% CBN by weight, contained 3.1% CBC by weight, but no other cannabinoids were detectable (based on Manufacturer's COA). The Z-average particle size was 99.59 nm, the D90 particle size was 139.0 nm, and the polydispersity index was 0.138. Lipid nanoparticles were also prepared using a dilute CBDa oil (Myriam's Hope, Nev.) with not modification to the formulation lipid ratios (results not shown). The results of the CBG and CBN nanoparticles are summarized in the table below.

TABLE 13

| Cannabinoid | Cannabinoid Composition | Z-Ave Particle Size | D90 Particle Size | Polydispersity Index |
|---|---|---|---|---|
| Global Cannabinoids CBG Isolate | CBG: 93.34% CBD: Not detected THC: Not detected | 105.6 nm | 241.0 nm | 0.206 |
| Global Cannabinoids | CBN: 80.5% CBC: 3.1% | 99.59 nm | 139.0 nm | 0.138 |

TABLE 13-continued

| Cannabinoid | Cannabinoid Composition | Z-Ave Particle Size | D90 Particle Size | Polydispersity Index |
|---|---|---|---|---|
| CBN Distillate | CBD: Not detected THC: Not detected | | | |

Example 15: Phytosterol Alternatives to Cholesterol Used to Prepare CBD Containing Lipid Nanoparticles CBD lipid nanoparticle formulations were prepared using the solvent based manufacturing process in 0.1 liter batches. In this example, formulations were prepared with different phytosterols as alternatives to cholesterol. The physterosterols were purchased from BASF corporation and named Vegapure 867 GN, Vegapure FS, and Vegapure 95DS. The phytosterol replaced cholesterol in the formulation at the same weight percent, no additional modifications were made to the formulation, no cholesterol was added. The table below summarizes the initial particle size measurements using the three phytosterol alternatives to cholesterol. The Vegapure 867 GN had a Z-average particle size of 85.1 nm and PDI of 0.152, the Vegapure FS had a Z-average particle size of 87.6 nm and PDI of 0.168, the Vegapure 95 DS had a particle size of 130.7 nm and PDI of 0.400.

TABLE 14

| BASF Vegapure 867 GN | | BASF Vegapure FS | | BASF Vegapure 95 DS | |
| --- | --- | --- | --- | --- | --- |
| Z-Ave | PDI | Z-Ave | PDI | Z-Ave | PDI |
| 85.1 ± 0.3 nm | 0.152 ± 0.008 | 87.6 ± 0.5 nm | 0.168 ± 0.004 | 130.7 ± 3.4 nm | 0.400 ± 0.042 |

Figure 18:
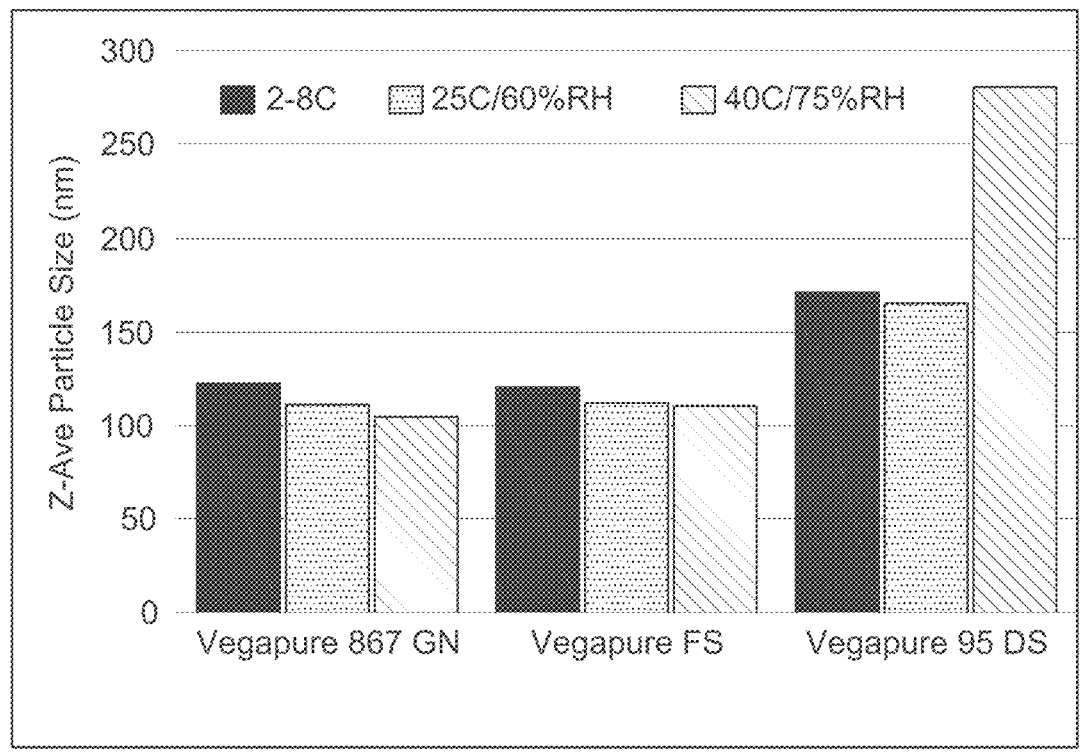
FIG. 18 shows short-term stability data for various embodiments of CBD lipid nanoparticles prepared with cholesterol alternative phytosterols.

In a preliminary, short-term stability study, formulations prepared with BASF Vegapure phytosterol were placed at 2-8° C., 25° C. with 60% relative humidity, and 40° C. with 75% relative humidity for 14 days. Formulations prepared with Vegapure 867 GN and Vegapure FS had Z-average particle sizes at or below 130.0 nm for all storage temperatures. The formulation prepared with Vegapure 95 DS had particle sizes above 150.0 nm when stored at 2-8° C. and 25° C. with 60% relative humidity, but the particle size increased to above 250 nm when stored at 40° C. with 75% relative humidity. The results are shown in FIG. 18.

Example 16: Preparing CBD Lipid Nanoparticles with Alternatives to Medium Chain Triglycerides Part 1: CBD lipid nanoparticles were prepared using the solvent based manufacturing process at 0.1-liter batches. The medium chain triglycerides (MCT) were replaced with alternatives available from ABITEC Corporation. Captex 8000 NF is triglyceride of caprylic acid, Captex GTO is a triglyceride of oleic acid, and Captex 1000 is a triglyceride of capric acid. The Captex triglycerides replaced the MCT in the weight percents stated in the table below. The table also summarizes the initial particle size and polydispersity index.

TABLE 15a

| Formulation | Initial Z-Average Particle Size | Initial Polydispersity Index |
| --- | --- | --- |
| 5% of ABITEC Captex 8000 NF | 111.3 ± 0.61 nm | 0.216 ± 0.005 |
| 10% of ABITEC Captex 8000 NF | 102.8 ± 2.05 nm | 0.194 ± 0.011 |
| 10% of ABITEC Captex GTO | 92.0 ± 0.98 nm | 0.117 ± 0.016 |
| 5% of ABITEC Captex GTO | 110.4 ± 0.51 nm | 0.280 ± 0.018 |
| 5% of ABITEC Captex 1000 | 105.3 nm | 0.180 |

CBD lipid nanoparticles were prepared using the solvent based manufacturing process at 0.1 liter batches. The medium chain triglycerides (MCT) were replaced with alternative non-aqueous liquids including omega-3 fatty acids (Tonalin and Pronova Pure® 46:38), glyceryl monooleate, conjugated linoleic acid, and alpha glycerylphosphorylcholine (alpha-GPC). The ingredients replaced MCT with an equivalent weight (10%) as presented in the original formulation. The table below summarizes the formulations and the initial particle size measurements.

TABLE 15b

| Formulation | Initial Z-Average Particle Size | Initial Polydispersity Index | Initial D90 Particle Size |
| --- | --- | --- | --- |
| Tonalin | 89.8 nm | 0.097 | 120.0 nm |
| Pronova Pure 46:38 | 81.8 nm | 0.084 | 106.0 nm |
| Glyceryl Monooleate | 104.8 nm | 0.114 | 152.0 nm |
| Conjugated Linoleic Acid | 244.2 nm | 0.159 | 410.0 nm |
| Alpha-GPC | 85.6 nm | 0.08 | 117.0 nm |

The table below shows the percent change in Z-average and polydispersity index when stored at 40° C. with 75% relative humidity for 30 days. A negative number indicates the particle size or PDI measurement decreased with respect to the initial measurements shown in the table above.

TABLE 16

| Formulation | Percent Change in Z-Ave Particle Size After 30 Days Storage At 40° C./75% RH | Percent Change in Polydispersity Index After 30 Days Storage At 40° C./75% RH |
| --- | --- | --- |
| 5% of ABITEC Captex 8000 NF | −13.92% | −25.93% |
| 10% of ABITEC Captex 8000 NF | −15.61% | −46.39% |
| 10% of ABITEC Captex GTO | −5.80% | −13.07% |
| 5% of ABITEC Captex GTO | −12.35% | −21.69% |
| 5% of ABITEC Captex 1000 | −13.06% | −18.90% |

Example 17: Preparation of an Embodiment of the Composition

A composition for the delivery of CBD was prepared using the following method. To prepare the composition, CBD (2.0 g) was dissolved in medium chain triglyceride (9.3 g) with mixing. To this solution was added, cholesterol (1.0 g) and phosphatidylcholine (10.0 g). Vitamin E was added (0.05 g) with stirring and to act as an antioxidant in the oil phase. At that time, malic acid (0.085 g), citric acid (0.085 mg), potassium sorbate (0.1 g), sodium benzoate (0.1 g), and Monk Fruit Extract (0.09 g) was added to water (76.07 g) with mixing. The aqueous phase was added to the oil phase with mixing.

Next, the oil-in-water emulsion was processed to a nanoparticle (about 20-500 nm) by successively passing the solution through microfluidizer (5 times at 30,000 PSI) at a temperature of at least 65° C. The microfluidizer contained an interaction chamber consisting of 50 to 70 um pore sizes.

Example 18: Preparation of an Embodiment of the Composition

A composition for the delivery of CBD was prepared using the following method. To 100 ml of ethanol was added CBD isolate (2.0 g) comprising not more than 0.3% THC by weight per weight (w/w). At that time, medium chain triglyceride (9.3 g) was added with mixing. To this solution was added, cholesterol (1.0 g), phosphatidylcholine (10.0 g), and Vitamin E (0.05 g).

Next, the solvent was removed to prepare a dried composition. An oil-in-water emulsion was prepared by suspending the dried composition with 76.07 g of warm water containing malic acid (0.085 g), citric acid (0.085 mg), potassium sorbate (0.1 g), sodium benzoate (0.1 g), and Monk Fruit extract (0.09 g). The oil-in-water emulsion was processed to a nanoparticle (20-500 nm) by successively passing the solution through microfluidizer 5 times at 30,000 PSI at a temperature of at least 75° C. The microfluidizer contained an interaction chamber consisting of 50 to 70 um pore sizes.

Example 19: Testing of an Embodiment of the Composition

A 5 Liter manufacturing batch was analyzed by high pressure liquid chromatography (HPLC) to measure cannabinoids present in the sample. The results were as shown in the following table:

TABLE 17

| Cannabinoid | LOQ (%) | Mass (%) | Mass (mg/g) |
|---|---|---|---|
| THCa | 0.01 | ND | ND |
| Δ9-THC | 0.01 | ND | ND |
| Δ8-THC | 0.01 | ND | ND |
| CBD | 0.01 | 2.12 | 21.2 |
| CBDa | 0.01 | ND | ND |
| CBC | 0.01 | ND | ND |
| CBG | 0.01 | ND | ND |
| CBN | 0.01 | ND | ND |
| THCV | 0.01 | ND | ND |
| CBGa | 0.01 | ND | ND |
| TOTAL | | 2.12 | 21.2 |

A 5 Liter manufacturing batch was analyzed by high pressure liquid chromatography (HPLC) to measure Terpenes present in the sample. The results were as shown in the following table:

TABLE 18

| Analyte | LOQ (%) | Mass %) | Mass (mg/g) |
|---|---|---|---|
| α-Bisabolol | 0.05 | ND | ND |
| α-Humulene | 0.05 | ND | ND |
| α-Pinene | 0.05 | ND | ND |
| β-Caryophyllene | 0.05 | ND | ND |
| β-Pinene | 0.05 | ND | ND |
| Caryophyllene Oxide | 0.05 | ND | ND |
| δ-Limonene | 0.05 | ND | ND |
| Linalool | 0.05 | ND | ND |
| Ocimene | 0.05 | ND | ND |
| Terpinolene | 0.05 | ND | ND |
| Trans-Nerolidol | 0.05 | ND | ND |

ND is not detected, below LOQ

Example 20. Noopept and CBD Lipid Nanoparticle Formulations

The solvent based lipid nanoparticle manufacturing process was used to create formulations of Noopept (N-phenylacetyl-L-prolyglygice ethyl ester). Noopept and lipids were dissolved in ethanol at elevated temperature and dried to form a film. Films were backed filled with dry nitrogen gas and stored at 4° C. for 12-24 hours before proceeding. Films were hydrated with warm water and mixed for 30 minutes before microfluidization, the final formulation volume was 100 mL. Formulations studied in this example are summarized in the table below.

TABLE 19

| Ingredient | Formulation 1 | Formulation 2 | Formulation 3 | Formulation 4 | Formulation 5 |
|---|---|---|---|---|---|
| H100-3 PC | 5 grams | 5 grams | 5 grams | 5 grams | 5 grams |
| Cholesterol | 0.5 grams | 0.5 grams | 0.5 grams | 0.5 grams | 0.5 grams |
| MCT | 4.8 grams | 4.8 grams | 0.28 grams | 4.8 grams | 0.28 grams |
| Noopept | 0 grams | 1 gram | 1 gram | 2 grams | 2 grams |
| Vitamin E | 0.05 grams | 0.05 grams | 0.05 grams | 0.05 grams | 0.05 grams |
| Purified Water | QS 100 mL | QS 100 mL | QS 100 mL | QS 100 mL | QS 100 mL |

Formulations 1-5 were placed on a 90 day stability study at 2-8° C., 25° C. with 60% relative humidity, and 40° C. with 75% relative humidity. The initial particle size measurements and measurements after 90 days at each stability temperature are shown in the table below.

TABLE 20

| | | Initial Measurement | 90 Days at 2-8° C. | 90 Days At 25° C./60% RH | 90 Days At 40° C./75% RH |
|---|---|---|---|---|---|
| Formulation 1 | Z-Average | 95.2 nm | 104.8 nm | 95.7 nm | 109.2 nm |
| | PDI | 0.153 | 0.162 | 0.153 | 0.249 |
| | D90 | 133.3 nm | 164.7 nm | 135.7 | 277.5 nm |

TABLE 20-continued

|  |  | Initial Measurement | 90 Days at 2-8° C. | 90 Days At 25° C./60% RH | 90 Days At 40° C./75% RH |
|---|---|---|---|---|---|
| Formulation 2 | Z-Average | 104.0 nm | 108.0 nm | 104.9 nm | 195.2 nm |
|  | PDI | 0.187 | 0.150 | 0.197 | 0.438 |
|  | D90 | 187.5 nm | 166.7 nm | 210.3 nm | 774.3 nm |
| Formulation 3 | Z-Average | 141.3 nm | 137.8 nm | 136.6 nm | 756.9 nm |
|  | PDI | 0.222 | 0.176 | 0.169 | 0.227 |
|  | D90 | 396.0 nm | 291.0 nm | 274.3 nm | 1973.3 nm |
| Formulation 4 | Z-Average | 108.4 nm | 111.6 nm | 116.8 nm | 140.8 nm |
|  | PDI | 0.177 | 0.165 | 0.278 | 0.513 |
|  | D90 | 188.7 nm | 199.3 nm | 189.7 nm | 3840.0 nm |
| Formulation 5 | Z-Average | 146.9 nm | 146.7 nm | 150.0 nm | 582.5 nm |
|  | PDI | 0.172 | 0.148 | 0.171 | 0.297 |
|  | D90 | 315.3 nm | 297.3 nm | 336.5 nm | 8090.0 nm |

Long-term stability of the formulation at room temperature and during temperature excursions (i.e. at 40° C. or higher) was improved by drying the Noopept lipid formulation to a powder. This was accomplished by dissolving 5% (w/v) of trehalose into the formulation and lyophilization to a dried cake as outline in Example 4. Fried formulations were broken up with a spatula, milled, followed by sieving through 75 to 34 micrometer sieves to achieve a fine powder. Powders were weighed into vials, back-filled with nitrogen and capped for long-term storage.

The Noopept lipid nanoparticle formulations may be modified further by co-incorporating a cannabinoid, such as CBD, CBG, CBN, or CBDa into the formulation. The formulation may be stored as a liquid or dried to a powder as outlined in Example 4.

Example 21. Melatonin and CBD Lipid Nanoparticle Formulations

Lipid nanoparticle formulations containing melatonin alone and melatonin and CBD were prepared using the solvent based manufacturing process. Melatonin alone or melatonin and CBD were, along with the other lipid ingredients, partially to completely dissolved in ethanol prior to drying to a film. The film was blanketed in nitrogen gas and stored for a period of 12 to 24 hours at 4° C. prior to processing. Solid lipid films were hydrated with warm water and mixed for 30 minutes to form a lipid slurry before being microfluidized. All formulations were prepared in 100 mL batches. The table below summarizes the formulations made in this example.

TABLE 21

| Formulations | H100-3 PC (g) | MCT (g) | CBD (g) | Melatonin (g) | Vitamin E (g) | Cholesterol (g) | Purified Water (mL) |
|---|---|---|---|---|---|---|---|
| 1 | 10 | 9.5 | 0 | 0 | 0.05 | 1 | QS 100 |
| 2 | 10 | 9.5 | 0 | 0.1 | 0.05 | 1 | QS 100 |
| 3 | 10 | 9.5 | 0 | 1 | 0.05 | 1 | QS 100 |
| 4 | 10 | 9.5 | 0 | 2.5 | 0.05 | 1 | QS 100 |
| 5 | 10 | 9.5 | 0 | 0.5 | 0.05 | 1 | QS 100 |
| 6 | 10 | 9.5 | 2 | 0 | 0.05 | 1 | QS 100 |
| 7 | 10 | 9.5 | 2 | 0.1 | 0.05 | 1 | QS 100 |
| 8 | 10 | 9.5 | 2 | 1 | 0.05 | 1 | QS 100 |
| 9 | 10 | 9.5 | 2 | 2.5 | 0.05 | 1 | QS 100 |
| 10 | 10 | 9.5 | 2 | 0.5 | 0.05 | 1 | QS 100 |

CBD and melatonin lipid nanoparticles were spray dried to a powder after the addition of trehalose to the liquid feed solution. Formulations were spray dried as outlined in Example 4. Prior to forming a powder, the initial particle size distribution was measured for Formulations 1-5 (melatonin only) and summarized in the table below. Powder formulations were sieved successively through 75 to 34 microns. Residual moisture for the powders was measured to be less than 6% for all formulations.

TABLE 22

|  | Z-Average Particle Size | Polydispersity Index | D90 Particle Size |
|---|---|---|---|
| Formulation 1 | 100.6 nm | 0.166 | 166.7 nm |
| Formulation 2 | 108.3 nm | 0.186 | 197.3 nm |
| Formulation 3 | 201.8 nm | 0.351 | Not Available |
| Formulation 4 | 156.2 nm | 0.325 | 731.3 nm |
| Formulation 5 | 137.9 nm | 0.235 | 310 nm |

Example 22. Lipid Nanoparticle Powder Formulations of CBD, Melatonin, and GABA The following lipid nanoparticle formulations are designed to promote sleep. The formulations were prepared using the solvent based manufacturing process in 200 mL batches. All lipids, CBD, and melatonin was dissolved in ethanol and dried to a film. The film was hydrated with a warm media containing up to 1.052 mg/mL each of sodium benzoate and potassium sorbate, and up to 0.622 mg/mL each of citric acid monohydrate and malic acid. After processing, GABA (gamma-aminobutyric acid) was dissolved into the lipid nanoparticle suspension and allowed to mix for 2 hours before characterization and spray drying (as outlined above).

TABLE 23

| Ingredient | Formulation 1 | Formulation 2 | Formulation 3 | Formulation 4 |
|---|---|---|---|---|
| H100-3 PC | 20 grams | 20 grams | 20 grams | 20 grams |
| Cholesterol | 2.0 grams | 2.0 grams | 2.0 grams | 2.0 grams |
| MCT | 19.0 grams | 19.0 grams | 19.0 grams | 19.0 grams |
| CBD | 4.0 grams | 4.0 grams | 4.0 grams | 4.0 grams |
| Melatonin | 400 mg | 400 mg | 200 mg | 200 mg |
| Vitamin E | 0.1 grams | 0.1 grams | 0.1 grams | 0.1 grams |
| GABA | 0 grams | 10 grams | 0 grams | 10 grams |
| Hydration Media | QS 200 mL | QS 200 mL | QS 200 mL | QS 200 mL |

Initial particle size measurements of the four formulations in liquid form are summarized in the table below. Data shown are the average±standard deviation of three independent measurements.

TABLE 24

| Parameter | Formulation 1 | Formulation 2 | Formulation 3 | Formulation 4 |
|---|---|---|---|---|
| Z-Average Particle Size | 113.9 ± 1.74 nm | 110.5 ± 1.02 nm | 103.2 ± 4.68 nm | 111.5 ± 1.12 nm |
| Polydispersity Index | 0.254 ± 0.004 | 0.186 ± 0.009 | 0.203 ± 0.021 | 0.191 ± 0.020 |

Example 23. Stability of CBD Lipid Nanoparticles in Simulated Gastric and Intestinal Fluids The stability of CBD Lipid Nanoparticles through the digestive process was simulated by measuring the particle size distribution in simulated gastric fluid after 2 hours, followed by dilution and incubation in simulated intestinal fluid after 4 hours. The CBD lipid nanoparticles were prepared using the solvent based manufacturing process at the 100 mL scale. Simulated gastric fluid was prepared by dissolving/dispersing 1 gram of sodium chloride (CAS 7647-14-5), 21.5 mg of sodium taurocholate (CAS 345909-26-4), 6.5 mg of lecithin (CAS 8002-43-5), and sufficient hydrochloric acid (CAS 7647-01-0) into purified water (QS 500 mL) to achieve a final pH of 1.6. Simulated intestinal fluid was prepared by dissolving/dispersing 1 gram of sodium chloride (CAS 7647-14-5), 806.5 mg of sodium taurocholate (CAS 345909-26-4), 64.4 mg of lecithin (CAS 8002-43-5), 1.1 grams of maleic acid (CAS 110-16-7), and 696 mg of sodium hydroxide (CAS 1310-73-2) in purified water (QS 500 mL). The pH was adjusted to 6.5 as needed. Simulated solutions were used immediately or stored at 4° C. for no longer than 1 month.

Prior to starting the study, simulated gastric and intestinal fluids were equilibrated to 37° C. Spectrum Laboratories Float-A-Lyzer G2 Dialysis devices (50 kD MWCO, 1 mL, Catalog #G235034) were equilibrated in 37° C. water prior to use. The initial particle size distribution was measured before starting the experiment. One mL of CBD lipid nanoparticles was placed on the interior of the Float-A-Lyzer, the cap was affixed, and the Float-A-Lyzer was placed into 20 mL of simulated gastric fluid inside a 50 mL conical tube. The conical tube containing the simulate fluid and sample was placed inside a 37° C. shaker incubator for 2 hours. At the end of the first incubation a sample was taken for particle size analysis. Immediately, the Float-A-Lyzer is placed in a new conical tube containing 20 mL of simulated intestinal fluid and returned to the 37° C. shaker incubator for 4 hours. At the end of the second incubation a sample was taken for particle size analysis. The total time of the experiment was 6 hours. Three commercially available, oil-based CBD products were analyzed similarly. All samples were measured in triplicate.

Figure 19A:
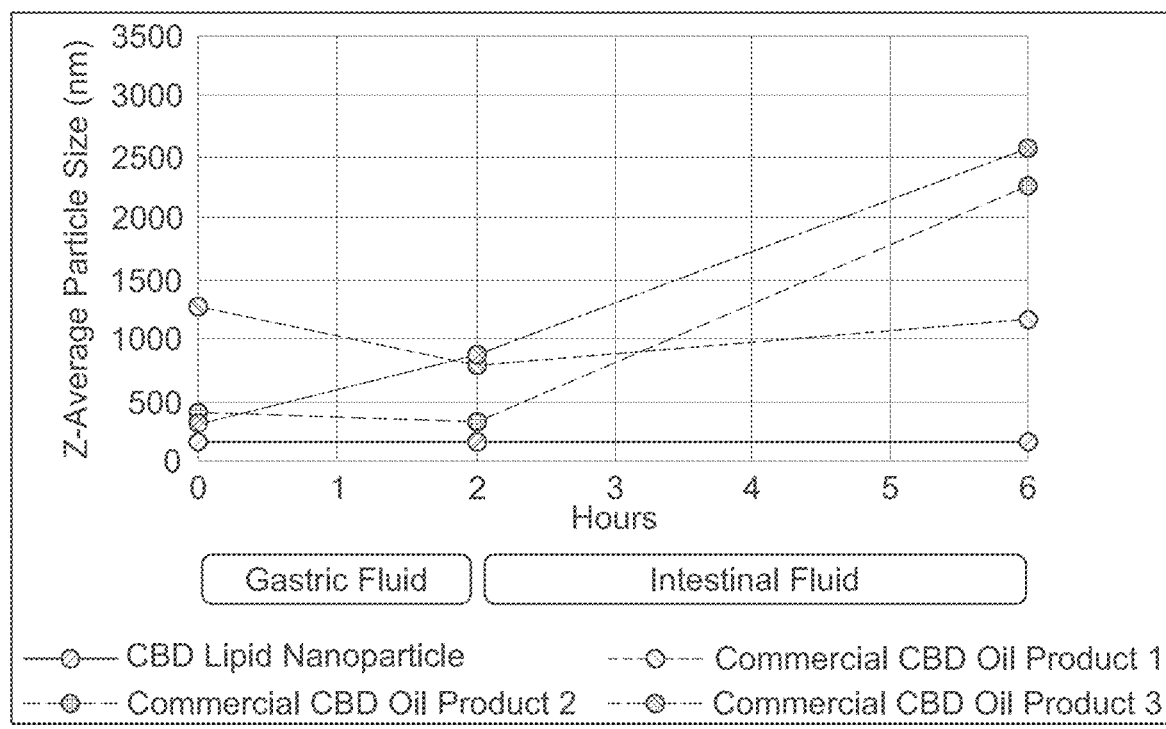
FIGS. 19A and 19B show stability data for various embodiments of CBD lipid nanoparticles in simulated gastric and intestinal fluids.
Figure 19B:
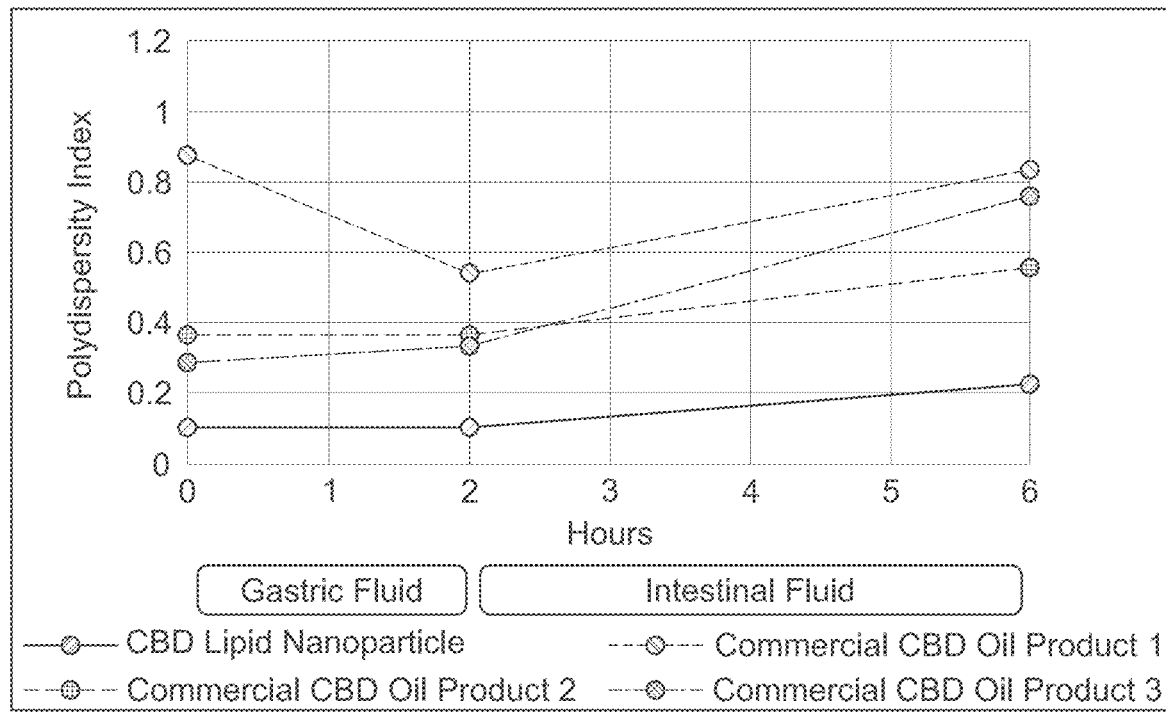

Shown in FIGS. 19A and 19B show the change in particle size and polydispersity index over the incubation period in simulated gastric and intestinal fluid. The CBD lipid nanoparticles experienced no change in particle size and a modest increase of PDI during the full incubation period. All the commercial oil-based CBD products experienced fluctuations in particle size and PDI during the incubation in simulated gastric and/or intestinal fluids, indicating an instability in the formulation during the digestive process.

Example 24. Preparation of CBD Lipid Nanoparticles With Oil Based, Less Pure Phospholipids CBD containing lipid nanoparticles were prepared using the solvent based manufacturing process in 0.1 liter batches. Lipid nanoparticles were prepared with oil based phospholipids and compared to the 99.0% pure phosphatidylcholine (H100-3). The compositions of the oil based phospholipids are provided in the table below under composition (information taken from manufacturer's COA), along with the initial particle size distribution measurements.

All formulations were prepared with 10% w/w phospholipid (Ingredient shown in the table below), 2% w/w CBD, 9.5% w/w medium chain triglycerides, 0.1% w/w vitamin E, and between 77.4 and 78.4% w/w purified water. The sample prepared with H100-3 phospholipid also had 1% w/w of cholesterol added.

TABLE 25

| Ingredient | Composition | Initial Z-Ave Particle Size | Initial PDI | Initial D90 Particle Size |
|---|---|---|---|---|
| Alcolec E 20 O (American Lecithin Company) | Saturated fatty acids: ~35% Monounsaturated fatty acids: ~36% Polyunsaturated fatty acids (C18:2, C18:3): ~19% Arachidonic acid (C20:4): ~2.5% Docosahexaenoic acid (C22:6): ~2% Cholesterol: Trace | 187.1 ± 1.31 nm | 0.090 ± 0.011 | 326.3 ± 7.64 nm |
| Alcolec E 80 O (American Lecithin Company) | Saturated fatty acids: 26-32% Monounsaturated fatty acids 17-19% Polyunsaturated fatty acids (C18:2, C18:3): 8-12% Arachidonic acid (C20:4): 3-5% Docosahexaenoic acid (C22:6): 1.5-2.5% Cholesterol: 1.9-6.6% | 213.9 ± 1.76 nm | 0.100 ± 0.016 | 396.3 ± 17.90 nm |
| H100-3 (American Lecithin Company) | Saturated fatty acids: 99.0% Monounsaturated and polyunsaturated fatty acids: 0.4% Cholesterol: not detected | 91.9 ± 0.61 nm | 0.119 ± 0.018 | 143.3 ± 11.85 nm |

Figure 20:
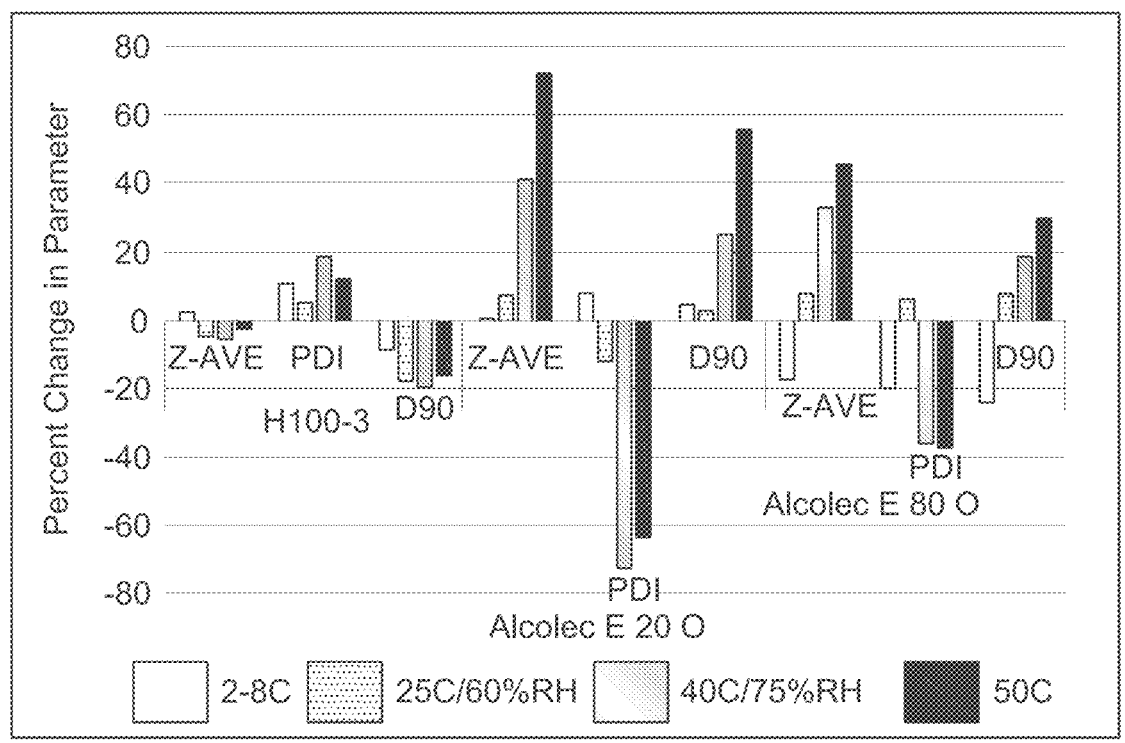
FIG. 20 shows stability data for various embodiments of CBD lipid nanoparticles.

Samples were placed at four storage conditions for a preliminary, short-term 2-week stability experiment. At the end of the incubation period, samples were measure for particle size distribution and percent changes were examined. For the sample prepared with H100-3 phospholipid, no parameter changed more than 20% from its initial measurement at any storage condition, indicating a stable product. Samples prepared with the less pure, oil-based phospholipids experienced significant changes in particle size parameters over the 2 week incubation period in one or more of the storage conditions, indicating a less stable product compared to lipid nanoparticles prepared with H100-3 phospholipid. Results are shown in FIG. 20.

Example 21. Examples of Sweeteners

CBD lipid nanoparticles were prepared using the solvent based manufacturing process at the 100 mL batch size. Dried lipid films were hydrated with a hydration media containing up to 1.052 mg/mL each of sodium benzoate and potassium sorbate, and up to 0.622 mg/mL each of citric acid monohydrate and malic acid as preservatives. A sweetener (0.09% w/w) was dissolved in the hydration media prior to adding to the dried film based on the formulations table below, no additional flavoring agent was added to the formulation. A day after processing the formulations were screened for initial particle size distribution (shown in the table below). Initial particle size measurements indicate that all sweeteners evaluated from Monkfruit Corporation, GLG Corporation, and Tate and Lyle are compatible with the CBD lipid nanoparticle formulation.

TABLE 26

| Formulation | Sweetener | Initial Z-Average Particle Size | Initial Polydispersity Index |
| --- | --- | --- | --- |
| Formulation 1 | Monk Fruit Corporation Catalog: MFC-J3.5 3.5% Mogrosides | 106.0 nm | 0.209 |
| Formulation 2 | Monk Fruit Corporation Catalog: MFC-E3OP 30% Mogrosides, de-proteined | 99.0 nm | 0.158 |
| Formulation 3 | Monk Fruit Corporation Catalog: MFC-E50 50% Mogrosides | 106.0 nm | 0208 |
| Formulation 4 | Monk Fruit Corporation Catalog: MFC-E55 | 108.0 nm | 0.197 |
| Formulation 5 | Monk Fruit Corporation Catalog: MFC-E80 80% Mogrosides | 106.0 nm | 0.186 |
| Formulation 6 | GLG Life Tech Corporation Catalog: GLG-MV55 55% Mogrosides | 107.0 nm | 0.214 |
| Formulation 7 | GLG Life Tech Corporation Catalog: GLG-RA97 97% Rebaudioside A | 97.0 nm | 0.191 |
| Formulation 8 | Tate and Lyle Catalog: TL-Stevia 3.05 95% Steviol Glycosides | 94.0 nm | 0.183 |
| Formulation 9 | Tate and Lyle Catalog: TL-Stevia 3.10 95% Steviol Glycosides | 100.0 nm | 0.218 |
| Formulation 10 | No Sweetener | 98.0 nm | 0.148 |

Example 22: Comparator Products

CBD comparator products with a common ingredient or label were purchased from the original manufacturer's website for particle size comparison to the embodiments described within. A key ingredient used in this search was phosphatidylcholine, phospholipids, lecithin, or MCT. Key words found on the label include nano, liposomal, and water soluble. Products were diluted into filtered, ultra-pure water to an optical density that yielded a suitable count for particle size measurement. The table below summarizes the particle sizes measured from the comparator products. All products measured had a particle size and polydispersity index that exceeds the formulations described herein, further supporting that the choice of ingredients and manufacturing process are key to producing a stable, nanoparticle.

TABLE 27

| Comp. | Label Ingredients | Label Claim | Z-Average Particle Size | Polydispersity Index | D90 Particle Size |
| --- | --- | --- | --- | --- | --- |
| 1 | Full Hemp Extract, Phospholipids with 50% phosphatidylcholine (organic lecithin), CBD Water, Xylitol, Glycerol, Sorbic Acid, Vitamin E, Pineapple Flavoring | Liposomal | 1,050.0 nm | 0.350 | Not Available |
| 2 | Purified Water, Olive Oil, Sunflower Lecithin, Anhydrous Hemp Oil, Potassium Sorbate, Vitamin E, Citric Acid | NanoCBD Suspended in Water | 790.0 nm | 0.310 | Not Available |
| 3 | Ultra-pure Nano Water, MCT Oil, Natural Gums, Vegetable Glycerin, Citric Acid, Potassium Sorbate, Sodium Benzoate | CBD Water Soluble Liquid 25 nm Particle Size | 7,493.0 nm | 1.000 | >10,000.0 nm |

TABLE 27-continued

| Comp. | Label Ingredients | Label Claim | Z-Average Particle Size | Polydispersity Index | D90 Particle Size |
|---|---|---|---|---|---|
| 4 | Purified Water, Hemp Extract, Saponin Extract, Ascorbic Acid | Nano CBD | 243.4 nm | 0.428 | 4970.0 nm |
| 5 | Vegetable Glycerin, CBD Extract, Hydrosome Electrolyte Blend, Polysorbate 80 | Water Soluble Rapid Release | 929.7 nm | 0.583 | 8,970.0 nm |
| 6 | Organic Vegetable Glycerin, Water, Quillaja Extract, CBD Hemp Oil, Moringa, Acerola Cherry, Vitamin C+ | Fast Acting Water Soluble | 7,140.0 nm | 1.000 | >10,000.0 nm |
| 7 | Hemp Seed Oil, CBD Extract | Tincture with BioPrime Nanoparticle Delivery Technology | 2,408.0 nm | 1.000 | 9,930.0 nm |
| 8 | Hemp-Derived CBD, Sunflower Lecithin, Cellulose, Calcium Phosphate | Nanoliposomal CBD Powder | 884.5 nm | 0.714 | >10,000 nm |

Example 23 CBD Lipid Nanoparticle Topical Lotion

Shown in the table below is a topical formulation utilizing the CBD lipid nanoparticle system as a carrier for CBD in a lotion/cream for surface pain relief. The base of the formulation (Phase A) utilizes Lipoid's Skin Lipid Matrix 2026 technology and is present in the final formulation at 50%. The CBD (50 mg/mL) lipid nanoparticle (Phase B) composition is described in other embodiments, but here without preservatives and flavoring, and is present in the final formulation at 20% (1% CBD). Phase C of the composition consists of lipid/oil based ingredients or oil soluble ingredients, and includes Captex 170 EP as a skin permeation enhancer, argan oil, menthol, arnica oil, camphor, and grapefruit seed oil present in total at 19% in the final formulation. Where menthol, arnica oil, camphor, and grapefruit seed oil are present for their topical analgesic properties. Lastly, Phase D of the composition is water and is present at 11%.

The lotion ingredients were combined through cold mixing. First, all ingredients in Phase C were combined and mixed until dissolved. Phase B was manufactured according to solvent based method described in previous embodiments. Phase A was combined with Phase A and mixed with a planetary mixer for 2 minutes at 2000 RPM. Phase C was added 5 mL at a time, followed by hand mixing with a spatula. When all of Phase C was added, the composition was further mixed for 2 minutes at 2000 RPM in a planetary mixer. Phase B was added 5 mL at a time, followed by hand mixing with a spatula. When all of Phase B was added, the composition was mixed a final time for 2 minutes at 2000 RPM in a planetary mixer. The batch of lotion was 100 mL and contained 1% of CBD.

Additional lotions were prepared with other permeation enhancers. For example, 5% of Captex 170 EP was replaced with 5% of dimethyl sulfoxide or 5% of dimethyl isosorbide. Additional lotions were prepared with additional topical analgesics such as lidocaine, wintergreen oil, or terpenes such as guaiacol.

TABLE 28

| Phase | Ingredient | INCI | Function | Supplier | % w/w |
|---|---|---|---|---|---|
| A | SLM2026 | Water, Caprylic/Capric Triglyceride, Hydrogenated Phosphatidylcholine, Pentylene Glycol, Glycerin, Butyrospermum Parkil Butter, Squalene, Ceramide NP | Base Formulation | Lipoid | 50% |
| B | CBD Lipid Nanoparticles | CBD (50 mg/mL), phosphatidylcholine, medium chain triglycerides, cholesterol, vitamin E | CBD carrier | | 20% |
| C | Captex 170 EP | Caprylic/Capric Acid Ester of Saturated Fatty Alcohol C12-C18 | Permeation Enhancer | ABITEC | 5% |
| | Argan Oil | Argania Spinosa Kernel Oil | Topical Analgesics | Varies | 5% |
| | Menthol | Menthol | | | 5% |
| | Arnica Oil | Arnica Montana Extract | | | 3% |

TABLE 28-continued

| Phase | Ingredient | INCI | Function | Supplier | % w/w |
|---|---|---|---|---|---|
| | Camphor | Camphor | | | 0.5% |
| | Grapefruit Oil | Citrus Paradisi Seed Oil | | | 0.5% |
| D | Deionized Water | Water | Diluent | | 11% |

Figure 21:
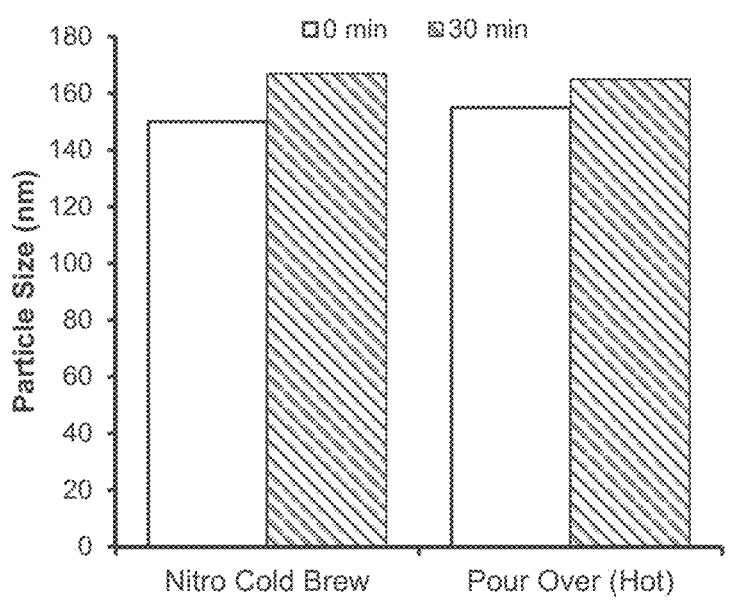
FIG. 21 shows embodiments of CBD nanoparticles in beverages and the nanoparticle size at two time points.

Example 24: Stability of CBD Lipid Nanoparticles in Hot and Cold Coffee Products CBD lipid nanoparticles was dispersed in coffee beverages at a concentration of 10 mg CBD per 8 ounce coffee beverage. A hot coffee beverage was prepared using the pour over technique, the resulting liquid was 130° F. at the time the CBD lipid nanoparticles were introduced. CBD nanoparticles were also dispersed in a nitro cold brew coffee (Parks Coffee), the coffee beverage was at 2-8° C. at the time the nanoparticles were introduced. After 30 minutes of storage in the beverage, the coffee was diluted for particle size measurement. The initial particle size measurement in each solution was compared to the particle size after 30 minutes of storage in two coffee beverages. As shown in the FIG. 21, the particle size only increased by 11.3% and 6.5% in cold and hot coffee beverages over 30 minutes, respectively, indicating the CBD lipid nanoparticles are stable in coffee beverages.

Example 25: Viscosity Measurement of an Embodiment

The viscosity of the CBD lipid nanoparticles (as prepared above in Example 1) was measured using a low volume adapter attached to a LV-DV-II+ Brookfield viscometer (Brookfield, Middleboro, Mass.). The viscosity was determined using 16 mL of solution at 26° C. and a spindle speed of 60 RPM, measured over 3 minutes. The viscosity of the CBD lipid nanoparticle solution was determined to be 5.096 Cp.

Example 26: Method of Treating

Based on the inventor's experience, the following prophetic results are projected using controlled studies.

Three groups of patients of age between 45 and 55 are admitted to treatment after having had been diagnosed with anxiety. The first group is treated with a CBD containing lipid-based particle composition as disclosed herein orally. The second group of patients is treated orally with a CBD oil based composition orally. The third group of patients is treated with a placebo orally. The first group of patients experiences recovery from each of the symptoms of anxiety faster than the second group and to a higher degree as measured by a self-evaluation. The patients in the first group report less feelings of nervousness, less feelings of restlessness, less feelings of impending danger, panic or doom, less trouble concentrating, less trouble sleeping. After oral ingestion, the patients in the first group have lower heart rates and less trembling than those in the second group. The results show statistically significant improvements in the first group relative to either the second group or the third group.

The patients in the second group show statistically significant improvement over the placebo, but not to the degree achieved reported by the first group. The patients in the second group have statistically higher reports of side effects associated with treatment than either the first or the second group.

Example 27: Method of Treating

Based on the inventor's experience, the following prophetic results are projected using controlled studies.

Three groups of female and male patients of age between 25 and 40 are admitted to treatment after having had been diagnosed with pain due to exercise related injuries. The first group is treated with a CBD containing lipid-based particle composition as disclosed herein topically. The second group of patients is treated topically with a competitor liposomal CBD based composition made with CBD oil. The third group of patients is treated with a placebo topically. The first group of patients experiences recovery from pain faster than the second group and to a higher degree as measured by a self-evaluation. The results show statistically significant improvements in the first group relative to either the second group or the third group.

The patients in the second group show statistically significant improvement over the placebo, but not to the degree achieved reported by the first group. The patients in the second group have statistically higher reports of side effects associated with treatment than either the first or the second group.

Example 28: Method of Treating

Based on the inventor's experience, the following prophetic results are projected using controlled studies.

Three groups of women patients of age between 35 and 40 are admitted to treatment after having had been diagnosed with premenstrual syndrome (PMS). The first group is treated with a GABA containing lipid-based particle composition as disclosed herein orally. The second group of patients is treated orally with a competitor liposomal GABA based composition. The third group of patients is treated with a placebo orally. The first group of patients experiences recovery from each of the symptoms of PMS faster than the second group and to a higher degree as measured by a self-evaluation. The patients in the first group report less cramping and less severity of cramping. After oral ingestion, the patients in the first group report having an improved moods. The results show statistically significant improvements in the first group relative to either the second group or the third group.

The patients in the second group show statistically significant improvement over the placebo, but not to the degree achieved reported by the first group. The patients in the second group have statistically higher reports of side effects associated with treatment than either the first or the second group.

Example 29: Method of Treating

Based on the inventor's experience, the following prophetic results are projected using controlled studies.

Three groups of patients of age between 35 and 40 are treated for insomnia. The first group is treated with a GABA/CBD containing lipid-based particle composition as disclosed herein orally. The second group of patients is treated orally with a competitor liposomal GABA/CBD oil based composition. The third group of patients is treated with a placebo orally. The first group of patients experiences faster sleep time than the second group that is statistically significant. The patients in the second group show statistically significant improvement over the placebo, but not to the degree achieved reported by the first group. The patients in the second group have statistically higher reports of side effects associated with treatment than either the first or the second group.

What is claimed is:

1. A lipid-based nanoparticle composition, comprising:
   cannabidiol (CBD) at a weight percent in the composition ranging from 1% to 10%;
   a phosphatidylcholine at a weight percent in the composition ranging from 2.5% to 15%;
   a sterol at a weight percent in the composition ranging from 0.5% to 5%; and
   a medium chain triglyceride at a weight percent in the composition ranging from 2.5% to 15%; and
   water at a weight percent in the composition ranging from 60% to about 80%;
   wherein nanoparticles of the composition have an average size ranging from about 75 nm to about 200 nm;
   wherein, when exposed to simulated gastric fluid at a pH of 1.6 and a temperature of 37° C. for a period of at least 1 hour, the average size of the nanoparticles changes less than or equal to 10%; and
   wherein, when exposed to simulated intestinal fluid at a pH of 6.5 and a temperature of 37° C. for a period of at least 1 hour, the average size of the nanoparticles changes less than or equal to 10%,
   wherein the lipid-based nanoparticle composition is free of surfactants and is free of emulsifiers other than phosphatidylcholine, and
   wherein the lipid-based nanoparticle composition is an oil in water nanoemulsion.

2. The lipid-based nanoparticle composition of claim 1, wherein an appreciable amount of the composition does not settle and/or separate from the water upon standing for a period of at least about one month at room temperature.

3. The lipid-based nanoparticle composition of claim 1, wherein the composition has a Tmax for CBD by oral administration of less than 4.5 hours.

4. The lipid-based nanoparticle composition of claim 1, wherein, upon storage for a period of one month at room temperature, the average size of the nanoparticles changes by less than 20%.

5. The lipid-based nanoparticle composition of claim 1, wherein the polydispersity of the nanoparticles in the composition is less than or equal to 0.20.

6. The lipid-based nanoparticle composition of claim 1, wherein upon 90 days of storage at 25° C. and 60% relative humidity, the polydispersity of the nanoparticles changes by less than or equal to 100%.

7. The lipid-based nanoparticle composition of claim 1, wherein upon 90 days of storage at 25° C. and 60% relative humidity, the polydispersity of the nanoparticles changes by less than or equal to 0.1.

8. The lipid-based nanoparticle composition of claim 1, upon 90 days of storage at 25° C. and 60% relative humidity, the D90 of the nanoparticles changes less than or equal to 10%.

9. The lipid-based nanoparticle composition of claim 1, wherein the composition comprises the CBD at a weight percent in the composition ranging from 0.5% to 4%.

10. The lipid-based nanoparticle composition of claim 1, wherein the composition comprises the phosphatidylcholine at a weight percent in the composition ranging from 7.5% to 12.5%.

11. The lipid-based nanoparticle composition of claim 1, wherein the sterol is cholesterol or a phytosterol; and the composition comprises the sterol at a weight percent in the composition ranging from 0.5% to 2%.

12. The lipid-based nanoparticle composition of claim 1, wherein the composition comprises the medium chain triglyceride at a weight percent in the composition ranging from 7.5% to 12.5%.

13. The lipid-based nanoparticle composition of claim 1, wherein the composition has a concentration max (Cmax) of at least 80 ng/ml after oral administration of 15 mg/kg.

14. A method comprising administering an amount of the composition of claim 1 to a patient.

15. A method of manufacturing the lipid-based nanoparticle composition of claim 1, the method comprising:
   providing cannabidiol;
   providing a phosphatidylcholine;
   providing a sterol;
   providing a medium chain triglyceride;
   providing water;
   mixing the water with the medium chain triglyceride, phosphatidylcholine, sterol, and cannabidiol to provide a mixture; and
   passing the solution through a high pressure or high shear homogenizer to provide a lipid-based particle composition.

* * * * *